(12) United States Patent
Yang et al.

(10) Patent No.: US 11,555,009 B2
(45) Date of Patent: Jan. 17, 2023

(54) 2-(SUBSTITUTED BENZENE MATRIX) AROMATIC FORMATE FTO INHIBITOR, PREPARATION METHOD THEREFOR, AND APPLICATIONS THEREOF

(71) Applicant: SHANGHAI INSTITUTE OF MATERIA MEDICA, CHINESE ACADEMY OF SCIENCES, Shanghai (CN)

(72) Inventors: Caiguang Yang, Shanghai (CN); Yue Huang, Shanghai (CN); Ze Dong, Shanghai (CN); Tao Zhang, Shanghai (CN); Hongjiao Xu, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/490,186

(22) PCT Filed: Mar. 1, 2018

(86) PCT No.: PCT/CN2018/077795
§ 371 (c)(1),
(2) Date: Nov. 25, 2019

(87) PCT Pub. No.: WO2018/157843
PCT Pub. Date: Sep. 7, 2018

(65) Prior Publication Data
US 2020/0079727 A1 Mar. 12, 2020

(30) Foreign Application Priority Data
Mar. 2, 2017 (CN) .......................... 201710121318.9

(51) Int. Cl.
*C07C 229/58* (2006.01)
*A61P 35/00* (2006.01)
(Continued)

(52) U.S. Cl.
CPC .......... *C07C 229/58* (2013.01); *A61K 31/196* (2013.01); *A61K 31/381* (2013.01);
(Continued)

(58) Field of Classification Search
CPC ... C07C 229/58; C07C 227/16; C07C 237/34; A61P 35/00; A61P 3/00; A61P 3/04; A61P 3/10; A61P 9/00; A61P 25/28; A61P 35/02; A61K 31/196; A61K 31/381; A61K 31/404; A61K 31/41; A61K 31/415; A61K 31/4164; A61K 31/42; A61K 31/422; A61K 31/4245; A61K 31/4418; A61K 31/4439; A61K 31/505; A61K 31/5355; A61K 45/06; A61K 31/198; A61K 31/4409;
(Continued)

(56) References Cited

U.S. PATENT DOCUMENTS 5,739,169 A 4/1998 Ocain et al.
2008/0293776 A1 11/2008 Barnes et al.
(Continued)

FOREIGN PATENT DOCUMENTS

CN 101312957 A 11/2008
CN 101466693 A 6/2009
(Continued)

OTHER PUBLICATIONS

Abdolali Alizadeh, Hadi Sedighian, Seyed Yasub Hosseini, and Long-Guan Zhu, Synthesis of Polysubstituted Benzenes via the Vinylogous Michael Addition of Alkylidenemalononitriles to 2-(1,3-Dioxo-1H-inden-2(3H)-ylidene)-malononitrile, HelveticaChimica Acta—vol. 98 (2015), 569 (Year: 2015).*
(Continued)

*Primary Examiner* — Kortney L. Klinkel
*Assistant Examiner* — Jason Deck
(74) *Attorney, Agent, or Firm* — Panitch Schwarze Belisario & Nadel LLP

(57) ABSTRACT

The invention provides 2-(substituted phenylhetero) aromatic formate FTO inhibitors, a preparation method thereof, and applications thereof. Specifically, disclosed in the present invention are a 2-(substituted phenylhetero) aromatic formate compound represented by the following formula (I), and a pharmaceutically acceptable salt, a hydrate or a solvate thereof, which can be used as an FTO targeting inhibitor for treating diseases associated with FTO targets, including obesity, metabolic syndrome (MS), type 2 diabetes (T2D), Alzheimer's diseases, and cancers such as breast cancers, small-cell lung cancers, human bone marrow rhabdomyosarcoma, pancreatic cancer, malignant glioblastoma and the like.

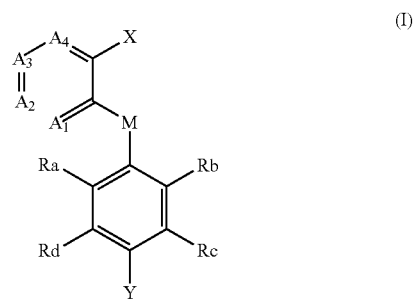

(I)

16 Claims, No Drawings

(51) Int. Cl.

| | | |
|---|---|---|
| *C07D 261/08* | (2006.01) | |
| *A61K 31/42* | (2006.01) | |
| *A61K 31/196* | (2006.01) | |
| *C07D 231/12* | (2006.01) | |
| *A61K 31/415* | (2006.01) | |
| *C07D 213/38* | (2006.01) | |
| *A61K 31/4418* | (2006.01) | |
| *C07D 333/20* | (2006.01) | |
| *A61K 31/381* | (2006.01) | |
| *C07D 239/26* | (2006.01) | |
| *A61K 31/505* | (2006.01) | |
| *C07D 333/40* | (2006.01) | |
| *C07D 239/42* | (2006.01) | |
| *C07D 211/70* | (2006.01) | |
| *C07D 209/14* | (2006.01) | |
| *A61K 31/404* | (2006.01) | |
| *C07D 233/64* | (2006.01) | |
| *A61K 31/4164* | (2006.01) | |
| *C07D 257/04* | (2006.01) | |
| *A61K 31/41* | (2006.01) | |
| *C07D 407/12* | (2006.01) | |
| *A61K 31/422* | (2006.01) | |
| *A61K 31/4245* | (2006.01) | |
| *C07D 401/12* | (2006.01) | |
| *A61K 31/4439* | (2006.01) | |
| *A61K 31/5355* | (2006.01) | |
| *C07C 227/16* | (2006.01) | |

(52) U.S. Cl.
CPC ............ *A61K 31/404* (2013.01); *A61K 31/41* (2013.01); *A61K 31/415* (2013.01); *A61K 31/4164* (2013.01); *A61K 31/42* (2013.01); *A61K 31/422* (2013.01); *A61K 31/4245* (2013.01); *A61K 31/4418* (2013.01); *A61K 31/4439* (2013.01); *A61K 31/505* (2013.01); *A61K 31/5355* (2013.01); *A61P 35/00* (2018.01); *C07C 227/16* (2013.01); *C07D 209/14* (2013.01); *C07D 211/70* (2013.01); *C07D 213/38* (2013.01); *C07D 231/12* (2013.01); *C07D 233/64* (2013.01); *C07D 239/26* (2013.01); *C07D 239/42* (2013.01); *C07D 257/04* (2013.01); *C07D 261/08* (2013.01); *C07D 333/20* (2013.01); *C07D 333/40* (2013.01); *C07D 401/12* (2013.01); *C07D 407/12* (2013.01)

(58) Field of Classification Search
CPC .............. A61K 31/4465; C07D 209/14; C07D 211/70; C07D 213/38; C07D 231/12; C07D 233/64; C07D 239/26; C07D 239/42; C07D 257/04; C07D 261/08; C07D 333/20; C07D 333/40; C07D 401/12; C07D 407/12; C07D 209/08; C07D 211/26; C07D 213/80; C07D 213/803; C07D 213/82; C07D 231/38; C07D 233/34; C07D 295/135; C07D 333/38; C07D 403/12; C07D 405/12; C07D 413/12

See application file for complete search history.

(56) References Cited

U.S. PATENT DOCUMENTS

| | | |
|---|---|---|
| 2009/0209586 A1 | 8/2009 | Blumenfeld et al. |
| 2009/0239829 A1 | 9/2009 | Rossello et al. |
| 2011/0129445 A1 | 6/2011 | Godessart Marina et al. |

FOREIGN PATENT DOCUMENTS

| | | | | |
|---|---|---|---|---|
| CN | 101568521 A | 10/2009 | | |
| CN | 102065866 A | 5/2011 | | |
| CN | 104069092 A | 10/2014 | | |
| CN | 105324376 A | 2/2016 | | |
| EP | 1860098 A1 | 11/2007 | | |
| JP | 2009545556 A | 12/2009 | | |
| JP | 5110198 B1 | 12/2012 | | |
| JP | 2013118288 A | 6/2013 | | |
| WO | 0041505 A2 | 7/2000 | | |
| WO | WO-0076489 A2 * | 12/2000 | ........... | C07C 229/58 |
| WO | WO-0105393 A2 * | 1/2001 | .............. | A61P 25/04 |
| WO | 2006098308 A1 | 9/2006 | | |
| WO | 2007005668 A2 | 1/2007 | | |
| WO | 2007009911 A1 | 1/2007 | | |
| WO | 2007067613 A1 | 6/2007 | | |
| WO | 2007135106 A1 | 11/2007 | | |
| WO | 2009065893 A1 | 5/2009 | | |
| WO | 2014165127 A1 | 10/2014 | | |
| WO | 2014207601 A1 | 12/2014 | | |

OTHER PUBLICATIONS

FDA approved solvents (Year: 2003).*
Int'l Search Report dated Jun. 4, 2018 in Int'l Application No. PCT/CN2018/077795.

* cited by examiner

2-(SUBSTITUTED BENZENE MATRIX) AROMATIC FORMATE FTO INHIBITOR, PREPARATION METHOD THEREFOR, AND APPLICATIONS THEREOF

CROSS-REFERENCE TO RELATED APPLICATION

This application is a Section 371 of International Application No. PCT/CN2018/077795, filed Mar. 1, 2018, which was published in the Chinese language on Sep. 7, 2018, under International Publication No. WO 2018/157843 A1, which claims priority under 35 U.S.C. § 119(b) to Chinese Application No. 2017101213189.9, filed Mar. 2, 2017, the disclosures of which are incorporated herein by reference in their entirety.

FIELD OF THE INVENTION

The present invention relates to the field of pharmaceutical compounds, and in particular, the present invention discloses a 2-(substituted phenylhetero) aromatic formate compound represented by the following formula (I), and a pharmaceutically acceptable salt or pharmaceutically acceptable solvate thereof that acts as an FTO-targeting inhibitor to treat FTO-targeted diseases such as obesity, metabolic syndrome (MS), type 2 diabetes (T2D), Alzheimer's Disease, and cancers such as breast cancer.

BACKGROUND OF THE INVENTION

Fat mass and obesity associated protein (FTO) was the first protein which was found to have both $m^6A$ ($N^6$-methyl adenosine) RNA demethylase activity and in vivo metabolism regulating activity. The knockout of Fto gene can cause severe growth retardation and multiple malformations. In addition to direct relation to obesity, FTO is also closely related to diseases such as metabolic syndrome (MS), type 2 diabetes, and Alzheimer's disease. Latest studies have shown that Fto is an important oncogene in the pathogenesis of solid tumors such as breast cancer and malignant glioblastoma, and knocking down Fto gene or reducing the expression of FTO protein can effectively inhibit proliferation of tumor cells such as breast cancer, malignant glioma cell brain tumor.

In summary, there is an urgent need in the art to develop small molecule inhibitors that specifically target FTO, and their use in the treatment of related diseases.

SUMMARY OF THE INVENTION

The object of the present invention is to design and synthesize a series of inhibitors specifically targeting FTO, and to achieve treatment of cancer such as small cell lung cancer, human bone marrow rhabdomyosarcoma, pancreatic cancer and malignant glioblastoma by inhibiting FTO enzymatic function or FTO protein-mediated signal transduction process.

In the first aspect of the invention, a compound of formula (I), and a pharmaceutically acceptable salt, hydrate, solvate or prodrug thereof is provided,

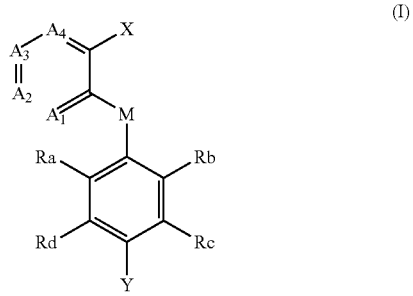

(I)

wherein, each of $A_1$, $A_2$, $A_3$ and $A_4$ is independently CR' or N;

M is selected from the group consisting of CR'$_2$, NH, O and S; R' is selected from the group consisting of H, halogen atom, carbonyl (=O), carboxyl, hydroxy, amino, nitro, cyano, $C_1$-$C_6$ alkoxy, $C_1$-$C_6$ alkylamino, $C_1$-$C_6$ alkoxycarbonyl, substituted or unsubstituted $C_1$-$C_6$ amido, $C_2$-$C_{12}$ ester group, and substituted or unsubstituted $C_1$-$C_{10}$ alkyl;

X has a structure selected from the group consisting of: carboxyl, hydroxamic acid group, substituted or unsubstituted $C_2$-$C_{12}$ ester group, substituted or unsubstituted amide group, and substituted or unsubstituted 3-12 membered heterocyclic group;

Y is selected from the group consisting of substituted or unsubstituted $C_6$-$C_{12}$ aryl, and substituted or unsubstituted 3-12 membered heterocyclic group;

each of $R_a$, $R_b$, $R_c$, and $R_d$ is independently selected from the group consisting of H, halogen, —OH, CN, $NO_2$, $NH_2$, substituted or unsubstituted $C_1$-$C_6$ alkyl, and substituted or unsubstituted $C_1$-$C_6$ alkoxy;

the term "substituted" means that one or more hydrogen atoms on the group are substituted with a substituent selected from the group consisting of halogen atom, carbonyl (=O), carboxyl, hydroxy, amino, nitro, cyano, $C_1$-$C_6$ alkoxy, $C_1$-$C_6$ alkylamino, $C_1$-$C_6$ alkoxycarbonyl, $C_1$-$C_6$ amido, $C_2$-$C_{12}$ ester group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{10}$ aryl, or substituted or unsubstituted five-membered or six-membered heteroaryl, 3-12 membered heterocyclyl, 3-12 membered cycloalkyl; preferably $C_1$-$C_6$ alkyl, halo $C_1$-$C_6$ alkyl, $C_1$-$C_6$ alkoxy or $C_1$-$C_6$ alkylamino; wherein the substituent of the substituted or unsubstituted $C_1$-$C_{10}$ alkyl, substituted or unsubstituted $C_6$-$C_{10}$ aryl or five-membered or six-membered heteroaryl is selected from the group consisting of halogen atom, carbonyl (=O), hydroxy, carboxy, $C_1$-$C_6$ alkoxycarbonyl, amino, $C_1$-$C_6$ acylamino, nitro, cyano, $C_1$-$C_6$ alkyl, halo$C_1$-$C_6$ alkyl, $C_1$-$C_6$ alkoxy, $C_1$-$C_6$ alkylamino, $C_6$-$C_{10}$ aryl, or 5- or 6-membered heteroaryl, 3-12 membered heterocyclyl, 3-12 membered cycloalkyl; preferably halogen atom, $C_1$-$C_6$ alkoxycarbonyl, $C_1$-$C_6$ alkyl, halo $C_1$-$C_6$ alkyl, $C_1$-$C_6$ alkoxy or phenyl, and 5-6 membered heterocyclic group.

In the second aspect of the invention, a compound of formula (I), and a pharmaceutically acceptable salt, hydrate, solvate or prodrug thereof is provided,

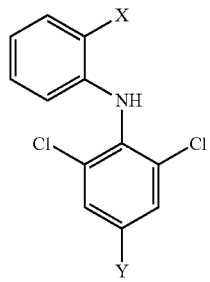

(I)

wherein,

X has a structure selected from the group consisting of: carboxyl, substituted or unsubstituted $C_2$-$C_{12}$ ester group, substituted or unsubstituted amide group, and substituted or unsubstituted 5-9 membered heterocyclic group;

Y is selected from the group consisting of: substituted or unsubstituted $C_6$-$C_{12}$ aryl, and substituted or unsubstituted 3-12 membered heterocyclic group;

the term "substituted" means that one or more hydrogen atoms on the group are substituted with a substituent selected from the group consisting of halogen atom, carbonyl (=O), carboxyl, hydroxy, amino, nitro, cyano, $C_1$-$C_6$ alkoxy, $C_1$-$C_6$ alkylamino, $C_1$-$C_6$ alkoxycarbonyl, $C_1$-$C_6$ amido, substituted or unsubstituted $C_1$-$C_{10}$ alkyl, and substituted or unsubstituted $C_6$-$C_{10}$ aryl and five-membered or six-membered heteroaryl; preferably $C_1$-$C_6$ alkyl, halo $C_1$-$C_6$ alkyl, $C_1$-$C_6$ alkoxy or $C_1$-$C_6$ alkylamino; wherein the substituent of the substituted or unsubstituted $C_1$-$C_{10}$ alkyl, substituted or unsubstituted $C_6$-$C_{10}$ aryl or five or six-membered heteroaryl is selected from the group consisting of halogen atom, carbonyl group (=O), hydroxy, carboxy, $C_1$-$C_6$ alkoxycarbonyl, amino, $C_1$-$C_6$ acylamino, nitro, cyano, $C_1$-$C_6$ alkyl, halo $C_1$-$C_6$ alkyl, $C_1$-$C_6$ alkoxy, $C_1$-$C_6$ alkylamino, $C_6$-$C_{10}$ aryl, and 5- or 6-membered heteroaryl; preferably halogen atom, $C_1$-$C_6$ alkoxycarbonyl, $C_1$-$C_6$ alkyl, halo $C_1$-$C_6$ alkyl, $C_1$-$C_6$ alkoxy or phenyl.

In another preferred embodiment, Y is not an unsubstituted phenyl.

In another preferred embodiment, X has a structure as shown in the following formula:

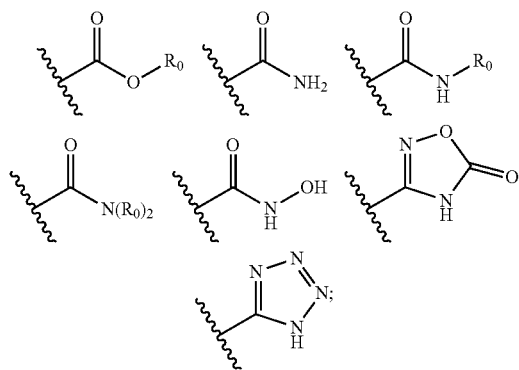

wherein each $R_0$ is independently selected from the group consisting of hydrogen, substituted or unsubstituted $C_1$-$C_6$ alkyl, substituted or unsubstituted $C_6$-$C_{10}$ aryl, substituted or unsubstituted $C_3$-$C_{10}$ cycloalkyl (including monocyclic, polycyclic, bridged ring structures), substituted or unsubstituted $C_2$-$C_6$ alkenyl, substituted or unsubstituted $C_2$-$C_6$ alkynyl, —OR", R" is selected from the group consisting of halogen atom, carboxy, hydroxy, amino, nitro, cyano, $C_1$-$C_6$ alkyl, $C_1$-$C_6$ alkoxy, $C_1$-$C_6$ alkylamino, $C_1$-$C_6$ alkoxycarbonyl, $C_1$-$C_6$ acylamino, $C_2$-$C_{12}$ ester group, substituted or unsubstituted $C_1$-$C_4$ alkyl-($C_6$-$C_{10}$ aryl), substituted or unsubstituted $C_1$-$C_4$ alkyl-(5-9 membered heterocyclyl), and substituted or unsubstituted five-membered or six-membered heteroaryl;

Y is substituted or unsubstituted benzene, substituted or unsubstituted pyridine, substituted or unsubstituted pyrimidine, substituted or unsubstituted pyridazine, substituted or unsubstituted tetrazine, substituted or unsubstituted triazine, substituted or unsubstituted pyrrole, substituted or unsubstituted thiophene, substituted or unsubstituted furan, substituted or unsubstituted tetrazole, substituted or unsubstituted triazole, substituted or unsubstituted imidazole, substituted or unsubstituted thiazole, substituted or unsubstituted oxazole, substituted or unsubstituted pyrazole, substituted or unsubstituted isothiazole, substituted or unsubstituted isoxazole, substituted or unsubstituted oxadiazole, substituted or unsubstituted thiadiazole, substituted or unsubstituted naphthalene, substituted or unsubstituted indole, substituted or unsubstituted indazole, substituted or unsubstituted quinoline, substituted or unsubstituted isoquinoline, substituted or unsubstituted benzofuran, substituted or unsubstituted benzothiophene, substituted or unsubstituted benzoimidazole, substituted or unsubstituted benzoxazole, substituted or unsubstituted benzothiazole, substituted or unsubstituted benzisothiazole, substituted or unsubstituted benzoisoxazole, substituted or unsubstituted benzotriazole, substituted or unsubstituted morpholine, substituted or unsubstituted dihydropiperidine, substituted or unsubstituted thiomorpholine, substituted or unsubstituted piperidine, substituted or unsubstituted piperazine, substituted or unsubstituted tetrahydropyran, substituted or unsubstituted dihydropyran, substituted or unsubstituted pyrroline, substituted or unsubstituted tetrahydrothiophene, substituted or unsubstituted tetrahydrofuran, substituted or unsubstituted oxetane, substituted or unsubstituted thietane, or substituted or unsubstituted azetidine.

In another preferred embodiment, the substituents are selected from the group consisting of halogen atom, hydroxyl, carboxyl, $C_1$-$C_6$ alkoxycarbonyl, amino, $C_1$-$C_6$ acylamino, nitro, cyano, $C_1$-$C_6$ alkyl, halogenated $C_1$-$C_6$ alkyl, $C_1$-$C_6$ alkoxy, $C_1$-$C_6$ alkylamino, $C_6$-$C_{10}$ aryl and five or six membered heteroaryl group; preferably are halogen atom, $C_1$-$C_6$ alkoxycarbonyl, $C_1$-$C_6$ alkyl, halogenated $C_1$-$C_6$ alkyl, $C_1$-$C_6$ alkoxy or phenyl.

In another preferred embodiment, the Y is selected from the group consisting of:

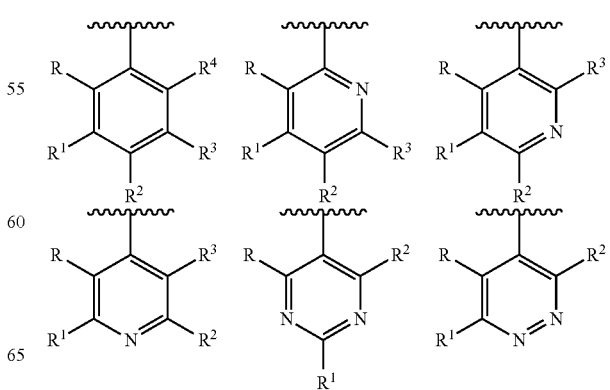

-continued
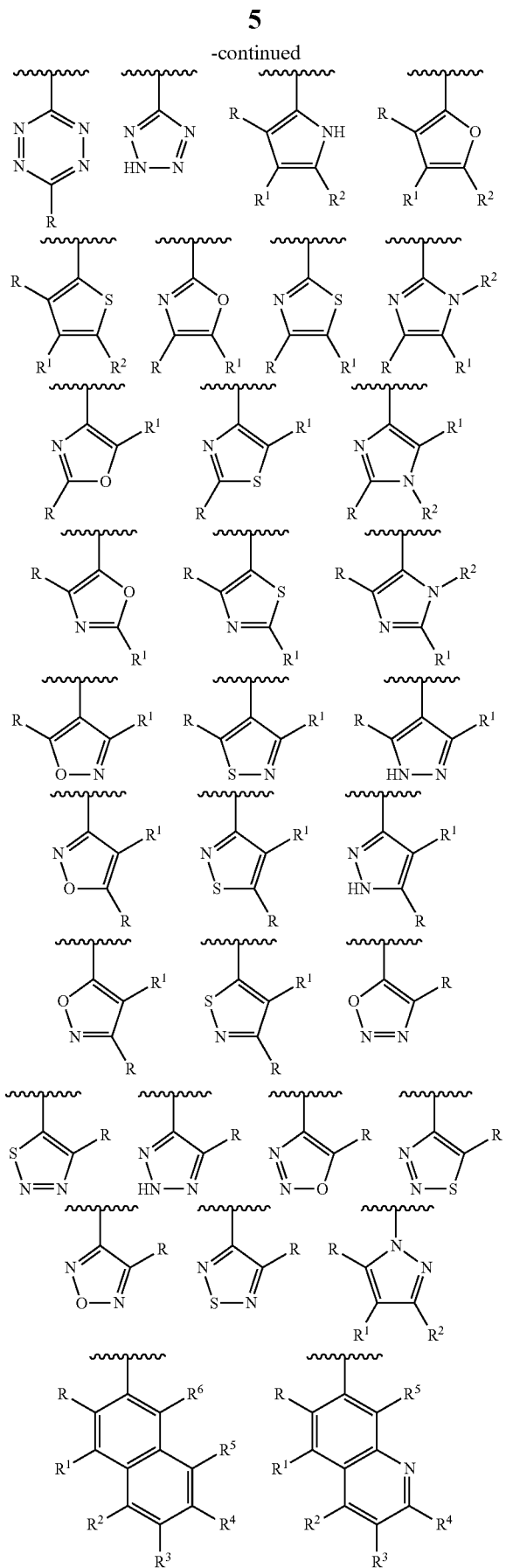
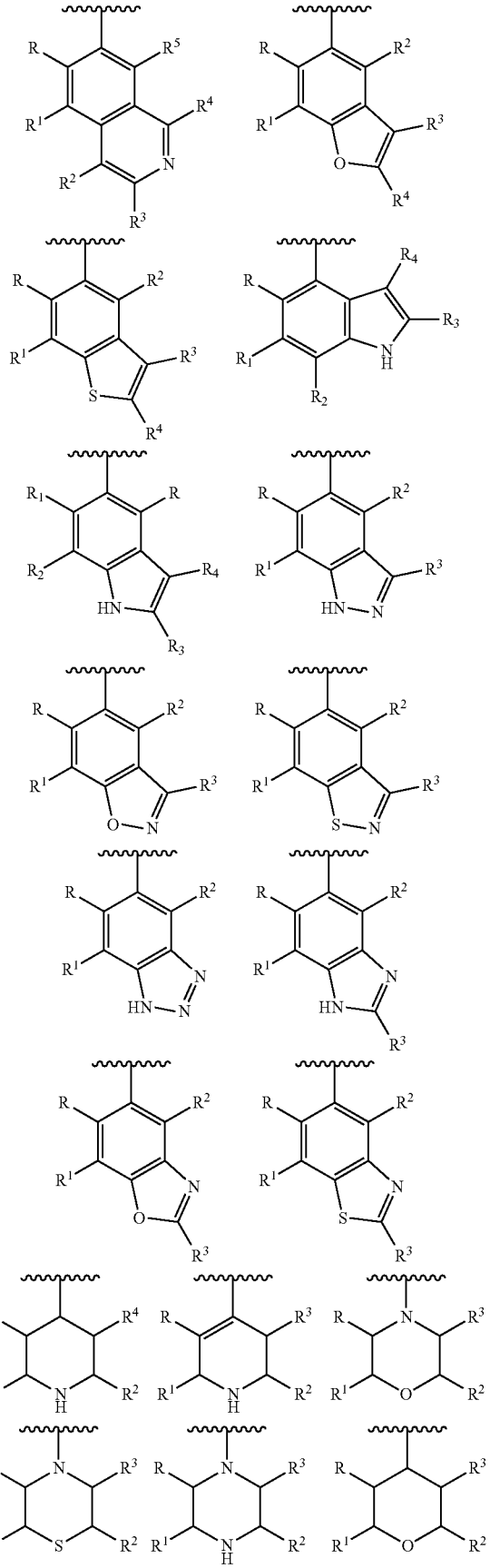

-continued

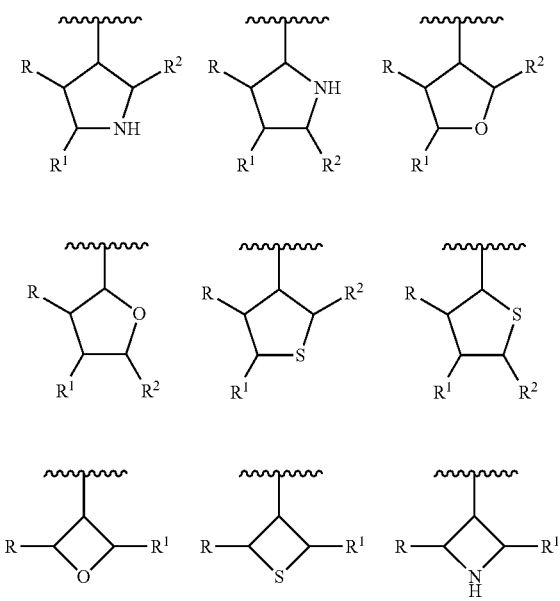

wherein each of R, $R^1$, $R^2$, $R^3$, $R^4$, $R^5$ and $R^6$ is independently hydrogen, carbonyl (=O), $C_1$-$C_6$ alkoxy, $C_1$-$C_6$ alkylamino, $C_1$-$C_6$ alkoxycarbonyl, $C_1$-$C_6$ acylamino, substituted or unsubstituted $C_1$-$C_{10}$ alkyl, substituted or unsubstituted $C_6$-$C_{10}$ aryl or five- or six-membered heteroaryl; preferably H, $C_1$-$C_6$ alkyl, halogenated $C_1$-$C_6$ alkyl, $C_1$-$C_6$ alkoxy or $C_1$-$C_6$ alkylamino;

wherein the substituent is selected from the group consisting of halogen atom, carbonyl (=O), carboxyl, hydroxyl, amino, nitro, cyano, $C_1$-$C_6$ alkoxycarbonyl, $C_1$-$C_6$ acylamino, $C_1$-$C_6$ alkyl, halo$C_1$-$C_6$ alkyl, $C_1$-$C_6$ alkoxy, $C_1$-$C_6$ alkylamino, $C_6$-$C_{10}$ aryl and five-membered or six membered heteroaryl; preferably is halogen atom, $C_1$-$C_6$ alkoxycarbonyl, $C_1$-$C_6$ alkyl, halo $C_1$-$C_6$ alkyl, $C_1$-$C_6$ alkoxy or phenyl.

In another preferred embodiment, each of $R_a$, $R_b$, $R_c$ and $R_d$ is independently selected from the group consisting of H, F, Cl, OH, methyl, and methoxy.

In another preferred embodiment, $R_a$ and $R_b$ are each independently H, or $R_c$ and $R_d$ are each independently H.

In another preferred embodiment, $R_a$ and $R_b$ are the same.

In another preferred embodiment, $R_c$ and $R_d$ are the same.

In another preferred embodiment, each of $A_2$ and $A_3$ is independently CR'.

In another preferred embodiment, the X group and the Y group are the groups corresponding to the compounds in the specific examples.

In another preferred embodiment, the R, $R^1$, $R^2$, $R^3$, $R^4$, $R^5$ and $R^6$ are the groups corresponding to the compounds in the specific examples.

In another preferred embodiment, the compound of formula I is selected from the group consisting of compounds 1-88.

In another preferred embodiment, the pharmaceutically acceptable salt is selected from the group consisting of inorganic acid salts, organic acid salts, inorganic alkali salts, and organic base salts.

In another preferred embodiment, the pharmaceutically acceptable salt is alkali metal salts, preferably lithium salts, sodium salts or potassium salts.

In another preferred embodiment, the inorganic acid salt is selected from the group consisting of hydrochloride, hydrobromide, hydroiodide, sulfate, disulfate, nitrate, phosphate, and acid phosphate; the organic acid salt is selected from the group consisting of formate, acetate, trifluoroacetate, propionate, pyruvate, glycolate, oxalate, malonate, fumarate, maleate, lactate, malate, citrate, tartrate, methanesulfonate, ethanesulfonate, besylate, salicylate, picrate, glutamate, salicylate, ascorbate, camphorate, and camphor sulfonate.

In the second aspect of the present invention, a use of compound of formula (I) is provided according to the first aspect of the invention, and the pharmaceutically acceptable salts, hydrates, solvates or prodrugs thereof in any of the following uses:

(a) preparation of a medicine for treating diseases associated with FTO protein activity or expression amount;

(b) preparation of a FTO protein activity targeting inhibitor;

(c) in vitro non-therapeutic inhibition of FTO protein activity; and/or (d) treatment of diseases associated with FTO activity or expression amount.

In another preferred embodiment, the inhibition comprises inhibition of the activity of the $m^6A$ demethylase FTO on DNA substrate and/or the activity of FTO on RNA substrate.

In another preferred embodiment, the disease is selected from the group consisting of obesity, metabolic syndrome (MS), type 2 diabetes (T2D), Alzheimer's disease, and cancers such as breast cancer, small cell lung cancer, human bone marrow rhabdomyosarcoma, pancreatic cancer, malignant glioblastoma.

In another preferred embodiment, the compound of formula I is administered in combination with a second therapeutic agent when the compound is used in the treatment of a disease associated with FTO activity or expression amount.

In the third aspect of the present invention, a pharmaceutical composition is provided which comprises: (i) a therapeutically effective amount of a compound of formula I, or a pharmaceutically acceptable salt, hydrate, solvate or prodrug thereof, and (ii) a pharmaceutically acceptable carrier.

In another preferred embodiment, the carrier is a liquid, and the concentration of the compound of formula (I) in the composition is ≤300 μM; preferably ≤200 μM; more preferably ≤100 μM; and most preferably ≤30 μM.

In another preferred embodiment, the pharmaceutical composition further comprises a second therapeutic agent.

In the fourth aspect of the present invention, a method of inhibiting FTO protein activity is provided which comprises a step of administering an inhibitory effective amount of a compound of formula I in the first aspect of the invention or a pharmaceutically acceptable salt thereof to a subject in which the FTO protein activity is to be inhibited, or administering an inhibitory effective amount of a pharmaceutical composition in the third aspect of the invention to the subject.

In the fifth aspect of the present invention, a method for preparation of a compound of formula I is provided which comprises:

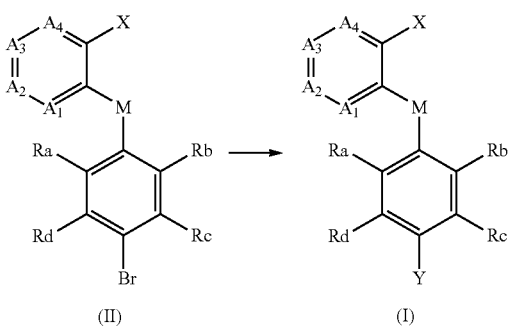

(II) → (I)

in an inert solvent, reacting a compound of formula II with a coupling reagent, thereby obtaining the compound of formula (I).

In another preferred embodiment, the coupling reagent is Y—B(OH)$_2$.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

After long-term and intensive studies, the inventors have found that a class of compounds represented by formula (I) can inhibit the activity of FTO protein with high efficiency and high selectivity, and the activity thereof is remarkably improved over the existing FTO inhibitors. The present invention is completed on this basis.

Terms

Unless specifically indicated, in the present invention, the term "substituted" means one or more hydrogen atoms on the group are substituted by a substituent selected from group consisting of: $C_1$-$C_{10}$ alkyl, $C_3$-$C_{10}$ cycloalkyl, $C_1$-$C_{10}$ alkoxy, halogen, hydroxy, carboxy (—COOH), $C_1$-$C_{10}$ aldehyde, $C_2$-$C_{10}$ acyl group, $C_2$-$C_{10}$ ester group, amino group, phenyl group; wherein the phenyl includes unsubstituted phenyl or phenyl substituted by one or more substitutents, wherein the substituent is selected from the group consisting of halogen, $C_1$-$C_{10}$ alkyl, cyano, OH, nitro, $C_3$-$C_{10}$ cycloalkyl, $C_1$-$C_{10}$ alkoxy, and amino.

As used herein, the term "$C_1$-$C_6$ alkyl" refers to linear or branched alkyl with 1 to 6 carbon atoms, such as methyl, ethyl, propyl, isopropyl, butyl, isobutyl, sec-butyl, tert-butyl, or the like.

The term "$C_1$-$C_6$ alkoxy" refers to a straight or branched chain alkoxy group having 1 to 6 carbon atoms, such as methoxy, ethoxy, propoxy, isopropoxy, butoxy, iso-butoxy, sec-butoxy, tert-butoxy, or the like.

The term "carbonyl $C_1$-$C_6$ alkyl" refers to a group having structure like "—CO-(straight or branched alkyl group of 1 to 6 carbon atoms)", such as carbonyl-methyl, carbonyl-ethyl, carbonyl-propyl, carbonyl-isopropyl, carbonyl-butyl, carbonyl-isobutyl, carbonyl-sec-butyl, carbonyl-tert-butyl, or the like.

The term "$C_6$-$C_{12}$ aryl" refers to an aryl having 6 to 12 carbon atoms, including monocyclic or bicyclic aryl, such as phenyl, naphthyl, or the like.

The term "3-12 membered heterocyclyl" refers to a saturated or unsaturated (including aromatic) 3-12 membered ring system having one or more heteroatoms selected from O, S, N or P, such as pyridyl, thienyl, piperidinyl, or the like, and preferably is a 4-9 membered heterocyclic groups.

The term "halogen" refers to F, Cl, Br and I.

In the present invention, the term "comprising", "comprise(s)" or "including" means that the various components can be used together in the mixture or composition of the present invention. Therefore, terms "essentially consist of . . . " and "consist of . . . " are within the term "comprising".

In the present invention, the term "pharmaceutically acceptable" component refers to substances which are suitable for administering to humans and/or animals without undue harmful side reactions (such as toxicity, stimulation or allergy), that is to say, substances of reasonable benefit/risk ratio.

In the present invention, the term "effective amount" refers to an amount in which the therapeutic agents can treat, relieve or prevent the targeted disease, or exhibit detectable treatment or prevention effects. The exact effective amount for a subject will depend on the size and health condition of the subject, the nature and extent of the disorder, and the therapeutic agent and/or therapeutic agent combination selected for administration. Therefore, it is useless to specify an accurate effective amount in advance. However, for a given situation, the effective amount may be determined by routine experimentation, which can be determined by clinicians.

In the present invention, unless otherwise indicated, the term "substituted" means that one or more hydrogen atoms on the group are substituted with a substituent selected from the group consisting of halogen, unsubstituted or halogenated $C_1$-$C_6$ alkyl, unsubstituted or halogenated $C_2$-$C_6$ acyl, and unsubstituted or halogenated $C_1$-$C_6$ alkyl-hydroxy.

Unless otherwise indicated, all compounds in the invention are intended to include all possible optical isomers, such as single chiral compounds, or mixtures of various chiral compounds (i.e., racemates). In compounds of the present invention, each chiral carbon atom may optionally be in R configuration or S configuration, or the mixture of R configuration and S configuration.

As used herein, the term "compound of the invention" refers to a compound of formula I. The term also comprises various crystal forms, pharmaceutically acceptable salts, hydrates or solvates of compound of formula I.

Compound of Formula I

The present invention provides a compound represented by the following formula (I), and pharmaceutically acceptable salts and prodrugs thereof,

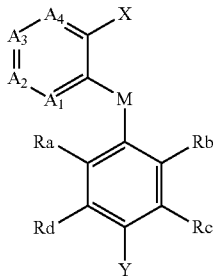

(I)

wherein, each of $A_1$, $A_2$, $A_3$ and $A_4$ is independently CR' or N;

M is selected from the group consisting of CR'$_2$, NH, O and S; R' is selected from the group consisting of H, halogen atom, carbonyl (=O), carboxyl, hydroxy, amino, nitro, cyano, $C_1$-$C_6$ alkoxy, $C_1$-$C_6$ alkylamino, $C_1$-$C_6$ alkoxycarbonyl, substituted or unsubstituted $C_1$-$C_6$ amido, $C_2$-$C_{12}$ ester group, and substituted or unsubstituted $C_1$-$C_{10}$ alkyl;

X has a structure selected from the group consisting of: carboxyl and a bioisostere thereof, hydroxamic acid group, substituted or unsubstituted $C_2$-$C_{12}$ ester group, substituted or unsubstituted amide group, and substituted or unsubstituted 3-12 membered heterocyclic group;

Y is selected from the group consisting of substituted or unsubstituted C6-C12 aryl, and substituted or unsubstituted 3-12 membered heterocyclic group;

each of $R_a$, $R_b$, $R_c$ and $R_d$ is independently selected from the group consisting of H, halogen, —OH, CN, NO$_2$, NH$_2$, substituted or unsubstituted $C_1$-$C_6$ alkyl, and substituted or unsubstituted $C_1$-$C_6$ alkoxy;

the term "substituted" means that one or more hydrogen atoms on the group are substituted with a substituent selected from the group consisting of: halogen atom, carbonyl (=O), carboxyl, hydroxy, amino, nitro, cyano, $C_1$-$C_6$ alkoxy, $C_1$-$C_6$ alkylamino, $C_1$-$C_6$ alkoxycarbonyl, $C_1$-$C_6$ amido, $C_2$-$C_{12}$ ester group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{10}$ aryl, or substituted or unsubstituted five-membered or six-membered heteroaryl, 3-12 membered heterocyclyl, 3-12 membered cycloalkyl; preferably $C_1$-$C_6$ alkyl, halo $C_1$-$C_6$ alkyl, $C_1$-$C_6$ alkoxy or $C_1$-$C_6$ alkylamino; wherein the substituent of the substituted or unsubstituted $C_1$-$C_{10}$ alkyl, substituted or unsubstituted $C_6$-$C_{10}$ aryl or five-membered or six-membered heteroaryl is selected from the group consisting of halogen atom, carbonyl (=O), hydroxy, carboxy, $C_1$-$C_6$ alkoxycarbonyl, amino, $C_1$-$C_6$ acylamino, nitro, cyano, $C_1$-$C_6$ alkyl, halogenated $C_1$-$C_6$ alkyl, $C_1$-$C_6$ alkoxy, $C_1$-$C_6$ alkylamino, $C_6$-$C_{10}$ aryl, or 5- or 6-membered heteroaryl, 3-12 membered heterocyclyl, 3-12 membered cycloalkyl; preferably halogen atom, $C_1$-$C_6$ alkoxycarbonyl, $C_1$-$C_6$ alkyl, halo $C_1$-$C_6$ alkyl, $C_1$-$C_6$ alkoxy or phenyl, 5-6 membered heterocyclic group.

In the present invention, the preferred compound of Formula I is selected from the group consisting of:

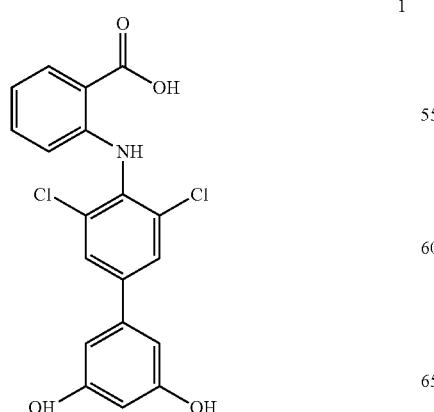

1

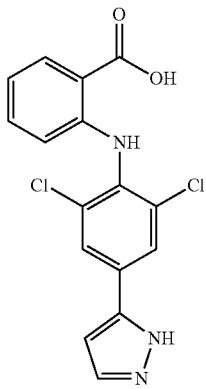

2

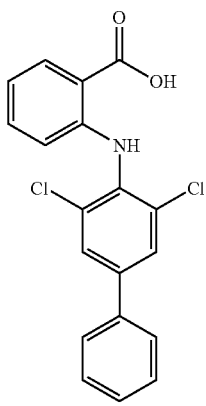

3

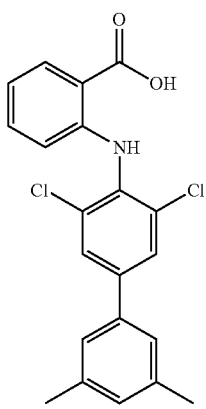

4

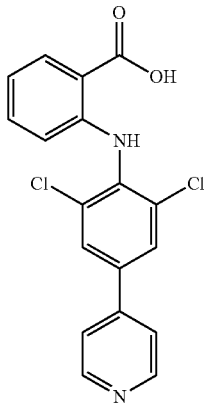

5

-continued
6
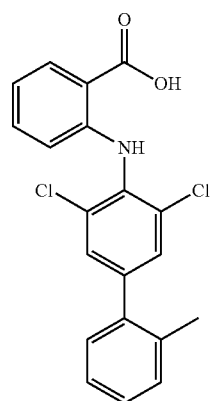
7
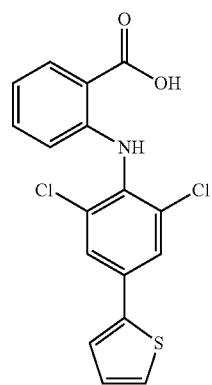
8
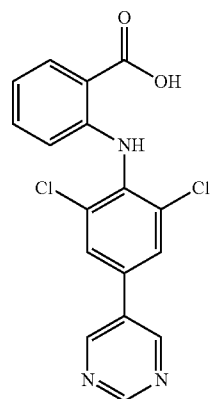
9
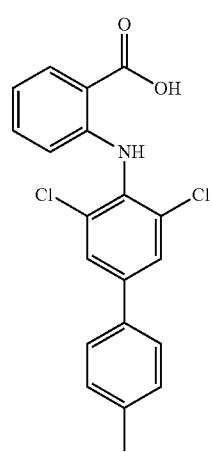
-continued
10
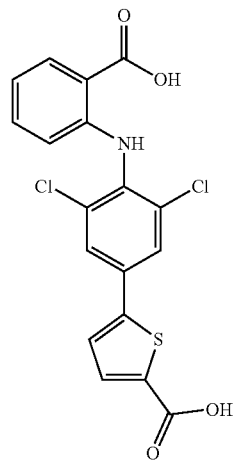
11
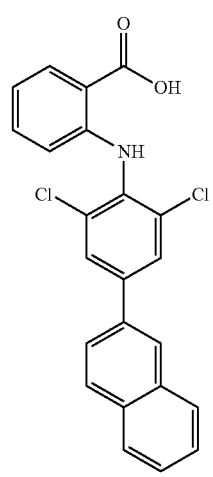
12
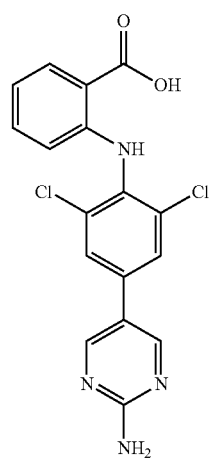

13
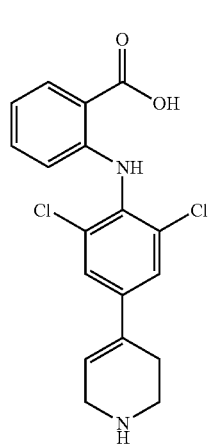
14
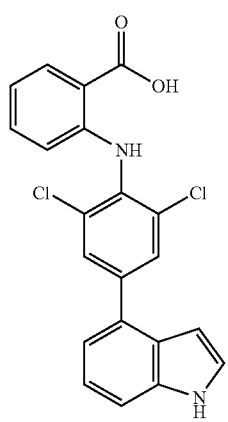
15
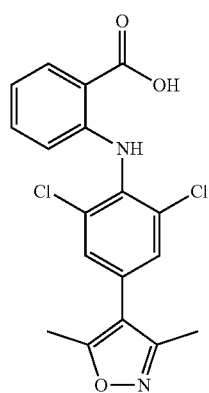
16
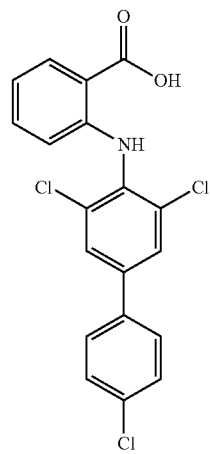
17
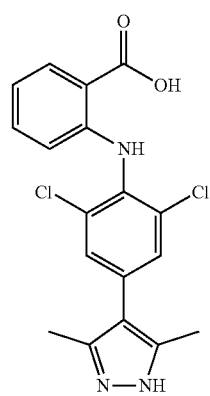
18
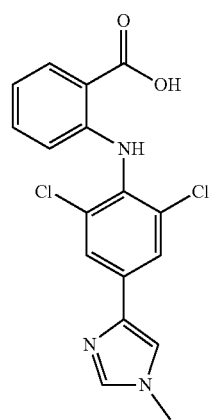

19
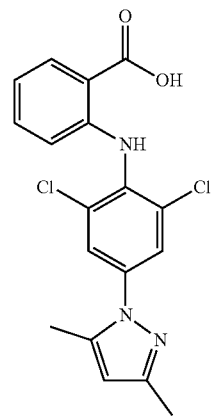
20
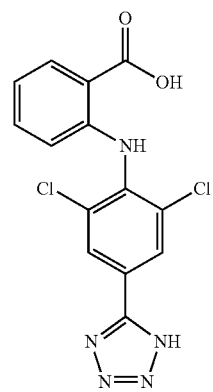
21
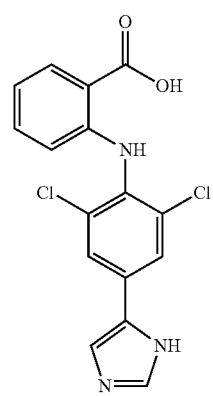
22
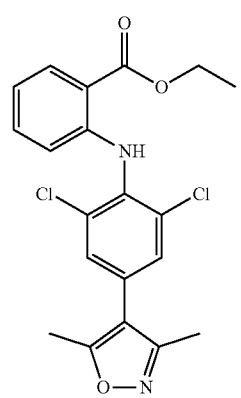
23
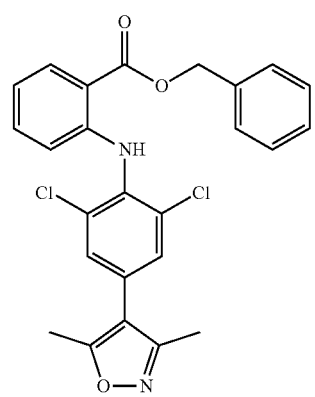
24
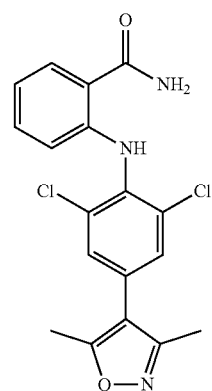
25
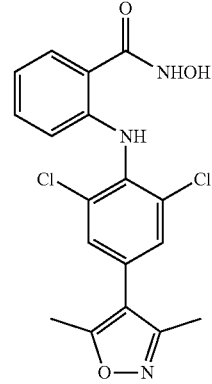
26
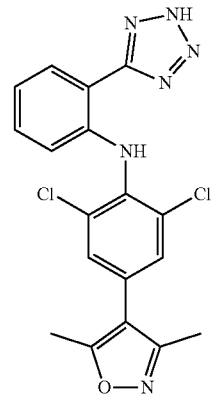

27
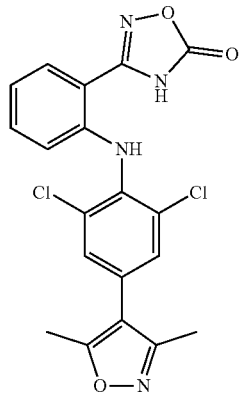
28
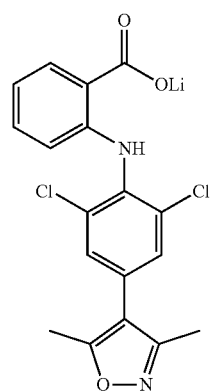
29
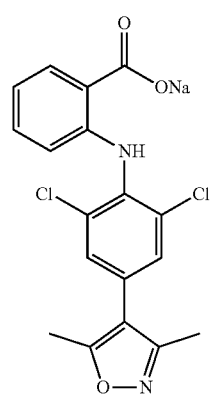
30
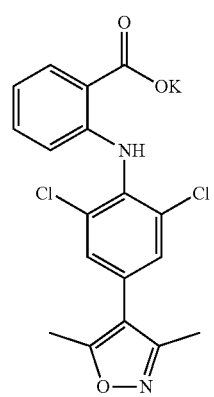
31
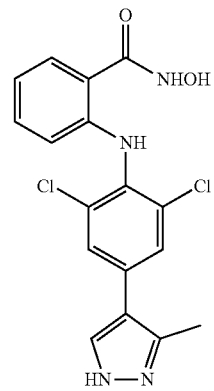
32
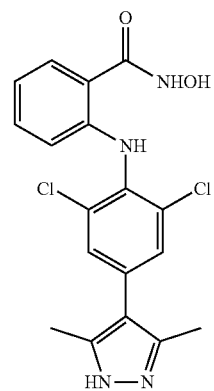
33
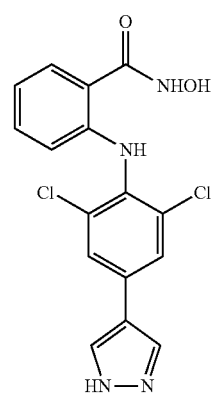
34
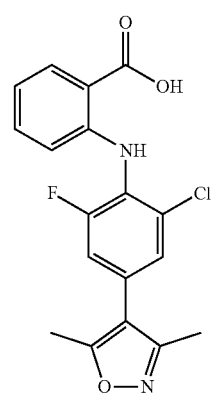

35
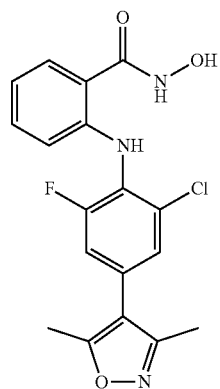
36
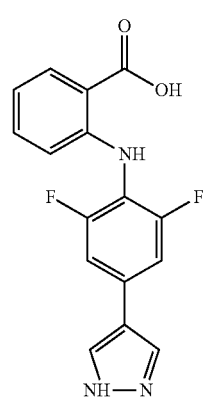
37
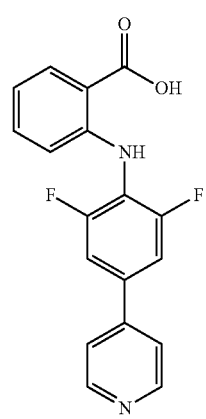
38
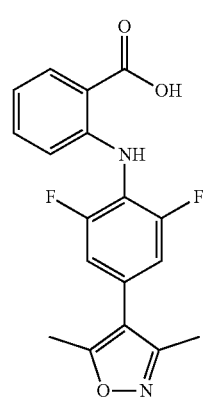
39
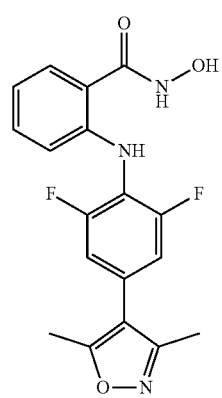
40
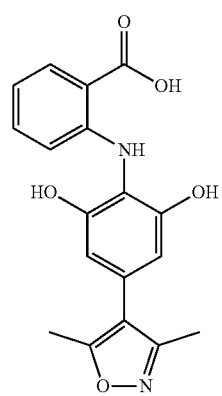
41
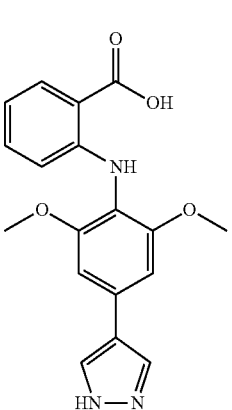
42
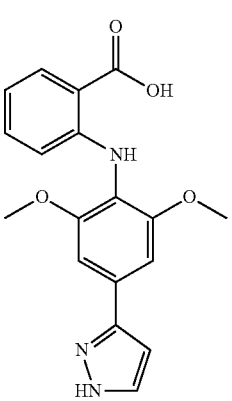

43
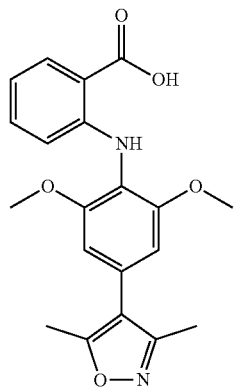
44
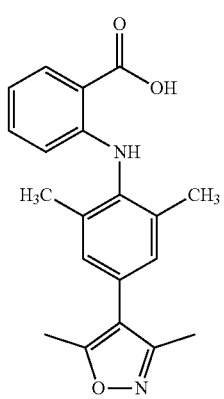
45
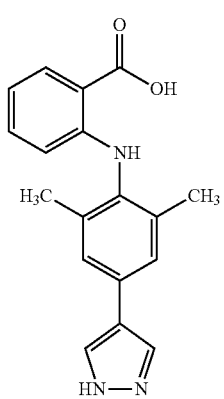
46
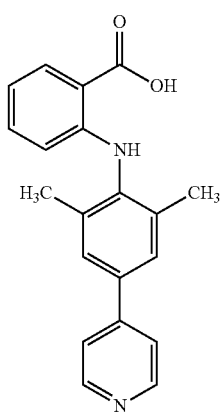
47
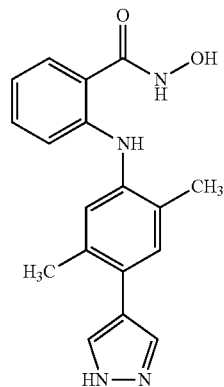
48
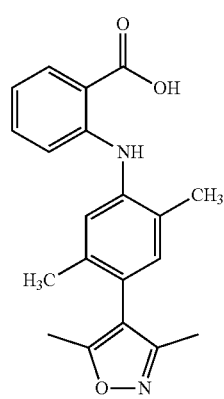
49
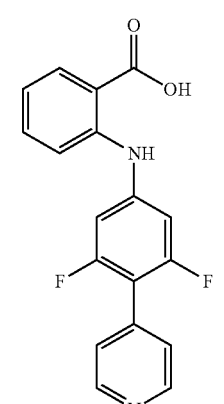
50
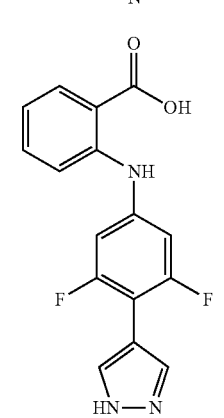

51 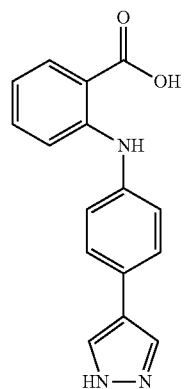
52 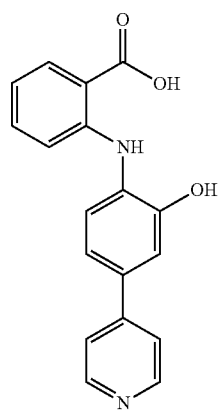
53 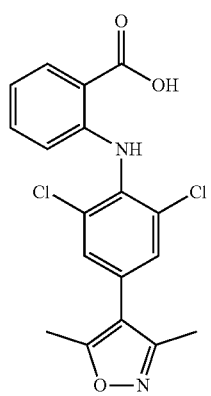
54 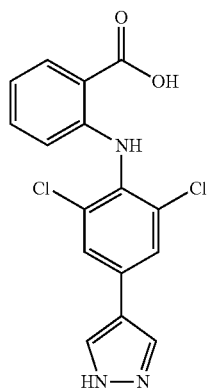
55 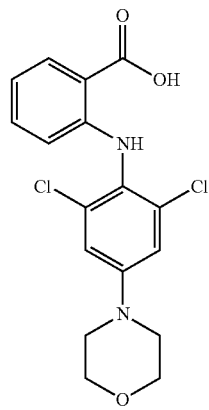
56 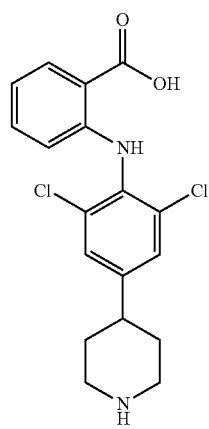
57 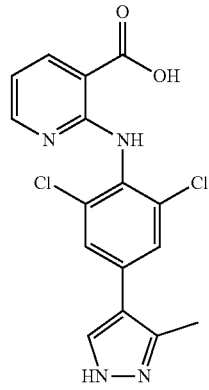
58 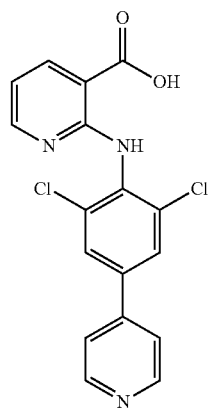

-continued
59
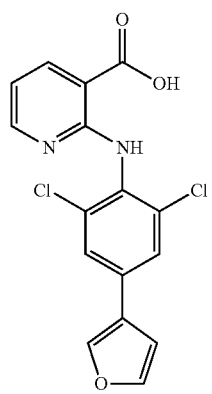
60
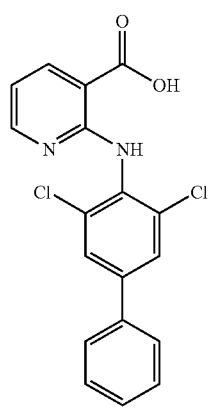
61
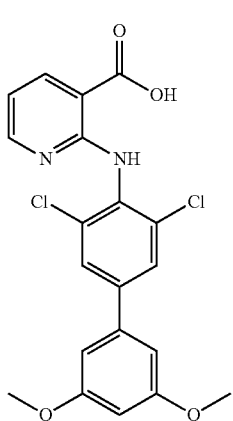
62
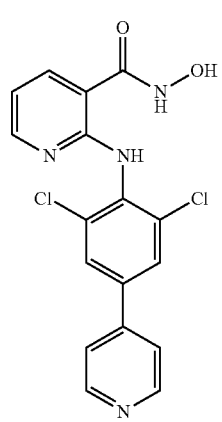
-continued
63
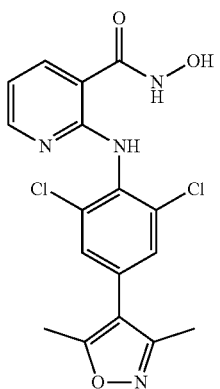
64
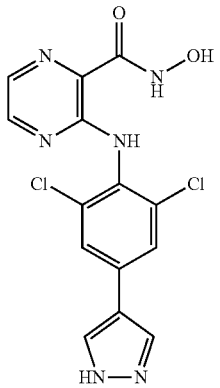
65
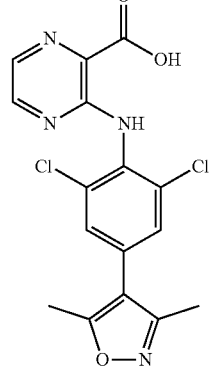
66
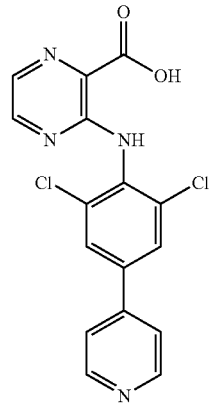

| | |
|---|---|
| 67 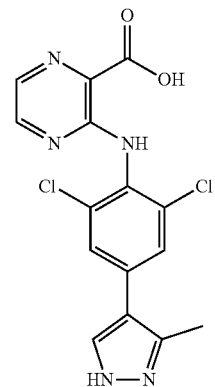 | 71 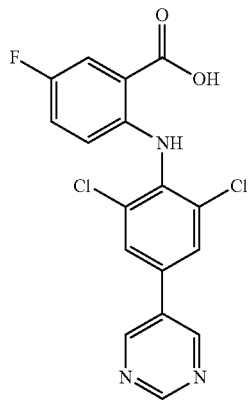 |
| 68 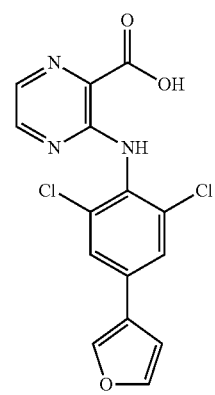 | 72 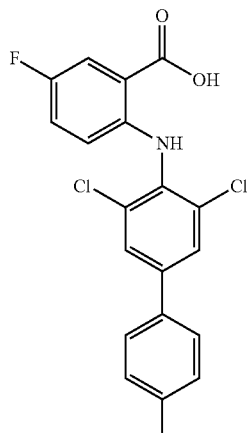 |
| 69 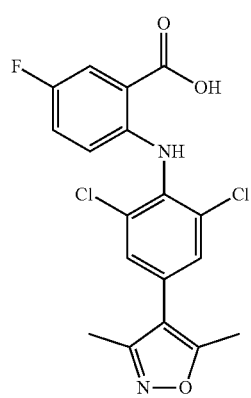 | 73 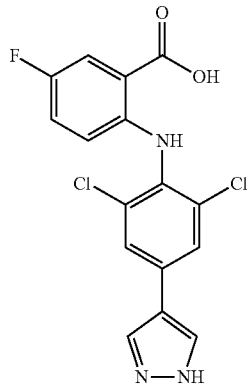 |
| 70 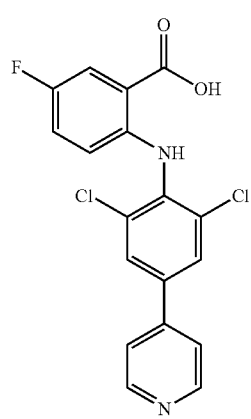 | 74 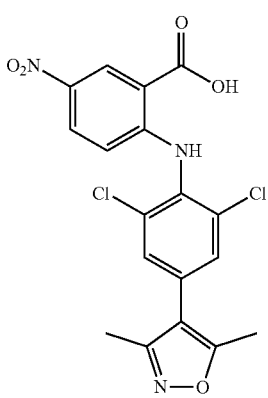 |

31
-continued
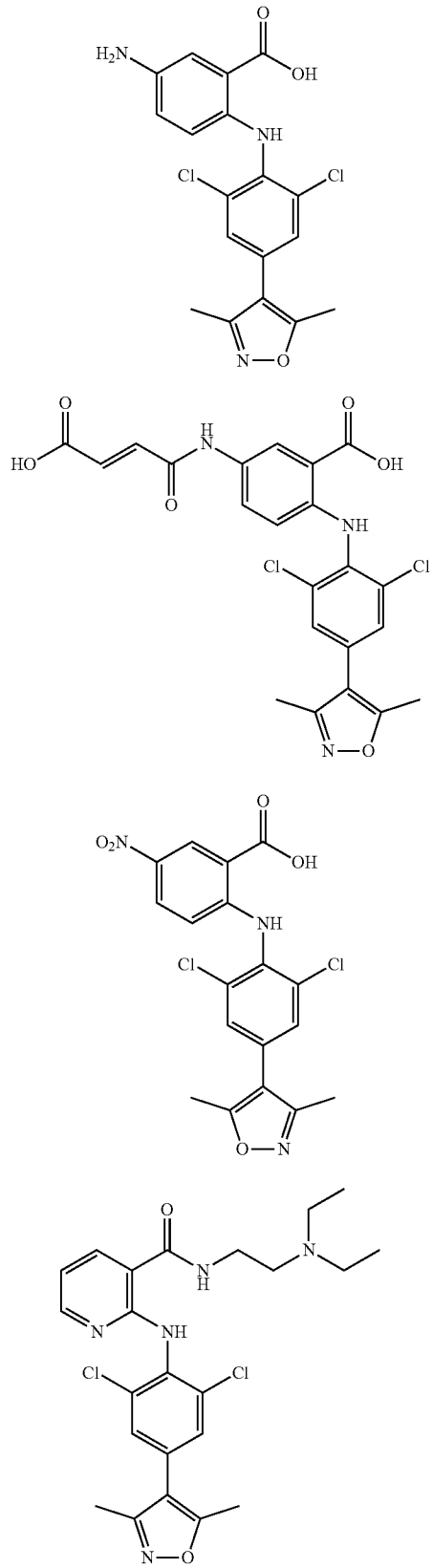
75
76
77
78
32
-continued
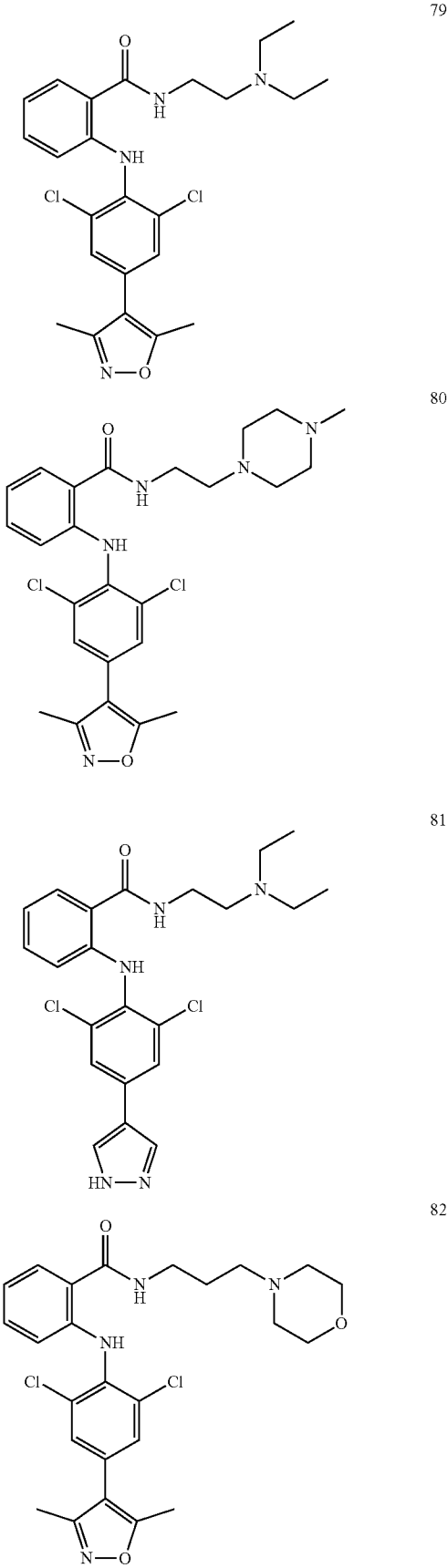
79
80
81
82

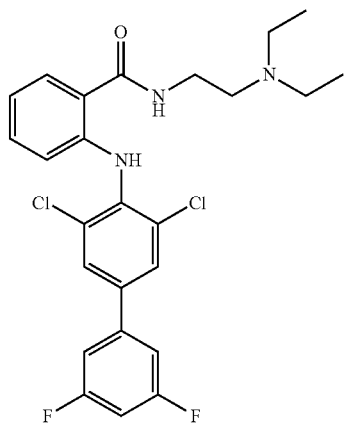

83

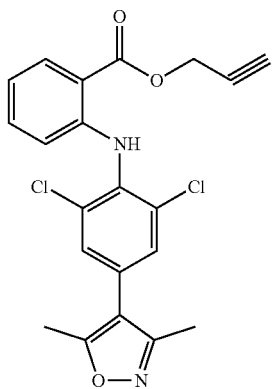

84

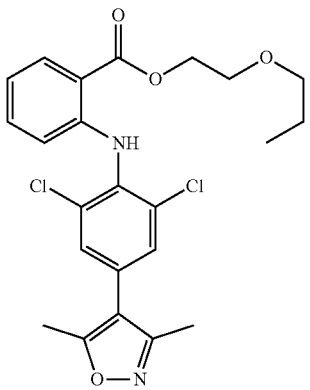

85

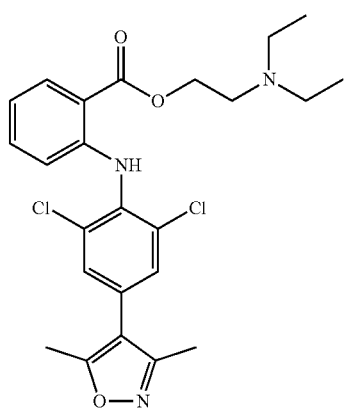

86

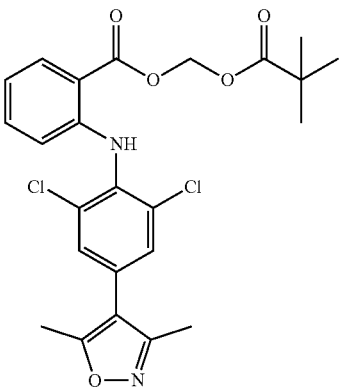

87

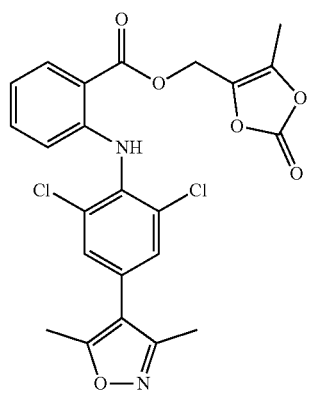

88

The pharmaceutically acceptable salt is preferably selected from inorganic acid salt or organic acid salt. The inorganic acid salt is selected from the group consisting of hydrochloride, hydrobromide, hydroiodide, sulfate, disulfate, nitrate, phosphate, and acid phosphate; the organic acid salt is selected from the group consisting of formate, acetate, trifluoroacetate, propionate, pyruvate, glycolate, oxalate, malonate, fumarate, maleate, lactate, malate, citrate, tartrate, methanesulfonate, ethanesulfonate, besylate, salicylate, picrate, glutamate, salicylate, ascorbate, camphorate, and camphor sulfonate.

Pharmaceutical Composition and Administration Thereof

The compounds of the present invention possess an outstanding activity of inhibiting FTO protein. Therefore, the compound of the present invention, and the crystal forms, pharmaceutically acceptable inorganic or organic salts, hydrates or solvates thereof, and the pharmaceutical composition comprising the compound of the present invention as a main active ingredient can be used for treating, preventing and alleviating diseases related to FTO activity or expression. Based on the prior art, the compounds of the present invention can be used in the treatment of diseases selected from obesity, metabolic syndrome (MS), type 2 diabetes (T2D), Alzheimer's disease, and cancers such as breast cancer, small cell lung cancer, human bone marrow rhabdomyosarcoma, pancreatic cancer, malignant glioblastoma.

The pharmaceutical composition of the invention comprises a safe and effective dosage of the compound of the present invention or the pharmaceutically acceptable salts thereof and pharmaceutically acceptable recipients or carriers. The term "safe and effective dosage" means that the amount of compound is sufficient to significantly ameliorate the condition without causing significant side effects. Generally, the pharmaceutical composition contains 1-2000 mg of a compound of the invention per dose, preferably, 5-200 mg of a compound of the invention per dose. Preferably, the "per dose" is one capsule or one tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation on administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or $CaHPO_4$, or mixed with any of the following components: (a) fillers or compatibilizer, for example, starch, lactose, sucrose, glucose, mannitol and silica acid; (b) binders, for example, hydroxymethyl cellulose, alginates, gelatin, polyvinylpyrrolidone, sucrose and Arabic gum; (c) humectants, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above recipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

In addition to these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or recipients include water, ethanol, polyols and any suitable mixtures thereof.

The dosage forms for topical administration of compounds of the invention include ointments, powders, patches, aerosol, and inhalants. The active ingredients are mixed under sterile conditions with physiologically acceptable carriers and any preservatives, buffers, or propellant, if necessary.

Compounds of the present invention can be administered alone, or in combination with any other pharmaceutically acceptable compounds.

When a pharmaceutical composition is used, a safe and effective amount of a compound of the present invention is applied to a mammal (such as human) in need of, wherein the dose of administration is a pharmaceutically effective dose. For a person weighed 60 kg, the daily dose is usually 1-2000 mg, preferably 5-500 mg. Of course, the particular dose should also depend on various factors, such as the route of administration, patient healthy status, which are well within the skills of an experienced physician.

The main advantages of the present invention include:

(1) The present invention provides a novel class of demethylase FTO inhibitors which inhibit FTO protein activity at very low concentration (typically $IC_{50}$ values is below 30 μM).

(2) The FTO inhibitor is of good safety.

(3) The FTO inhibitor has a high selectivity in inhibiting FTO demethylase, and does not show inhibitory effect on otherdioxygenase in the same family or superfamily.

(4) The FTO inhibitor has FTO targeting activity at the cellular level.

(5) The FTO inhibitor has good stability in plasma.

(6) The FTO protein activity inhibitor of the present invention exhibits a good pharmacokinetic effect in mouse in-vivo models.

The present invention will be further illustrated below with reference to the specific examples. It should be understood that these examples are only to illustrate the invention but not to limit the scope of the invention. The experimental methods with no specific conditions described in the following examples are generally performed under the conventional conditions such as J. Sambrook et al., Molecular Cloning: A Laboratory Manual (New York: Cold Spring Harbor Laboratory Press, 1989), or according to the manufacturer's instructions. Unless indicated otherwise, parts and percentage are weight parts and weight percentage.

The experimental reagents in the experiment were mainly purchased from China National Medicine Corporation, Sigma and Shanghai Shengong.
The compound numbers mentioned in the examples are shown as follows:
1
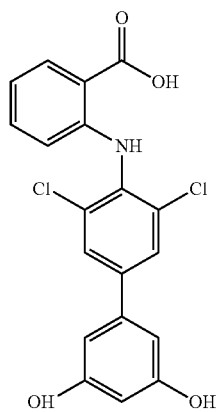
2
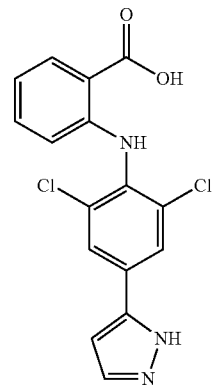
3
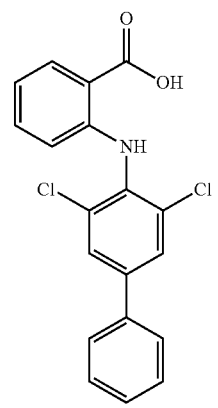
4
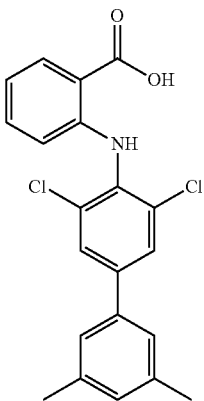
5
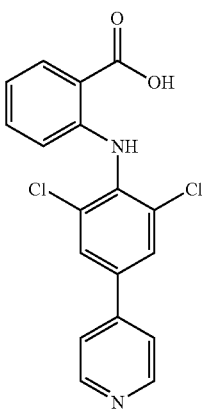
6
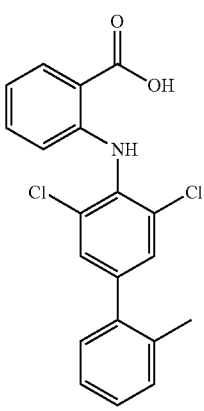
7
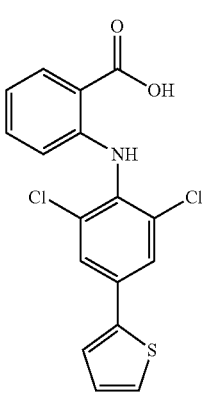

8
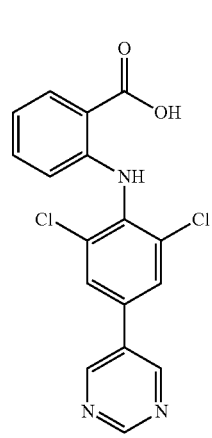
9
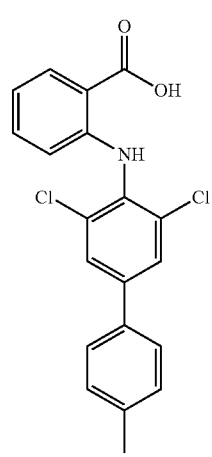
10
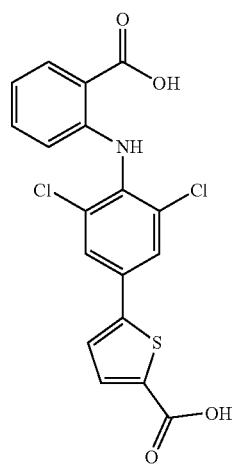
11
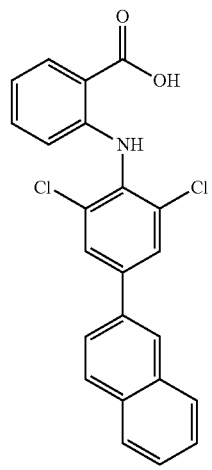
12
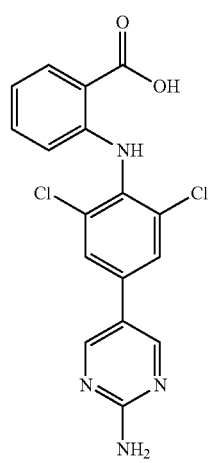
13
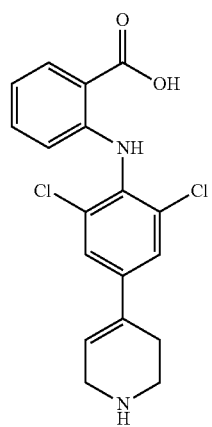

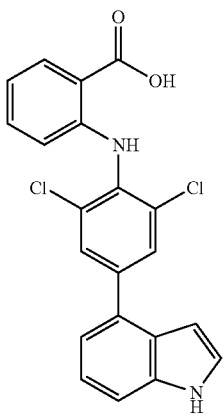
14
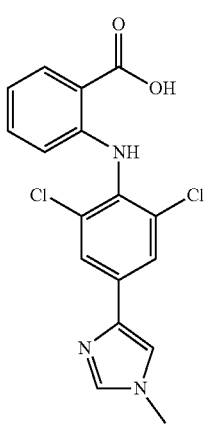
18
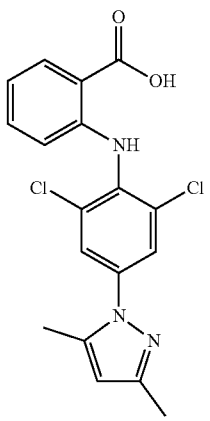
19
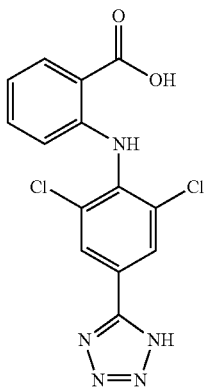
20
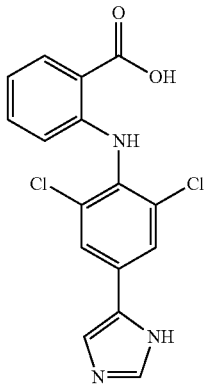
21

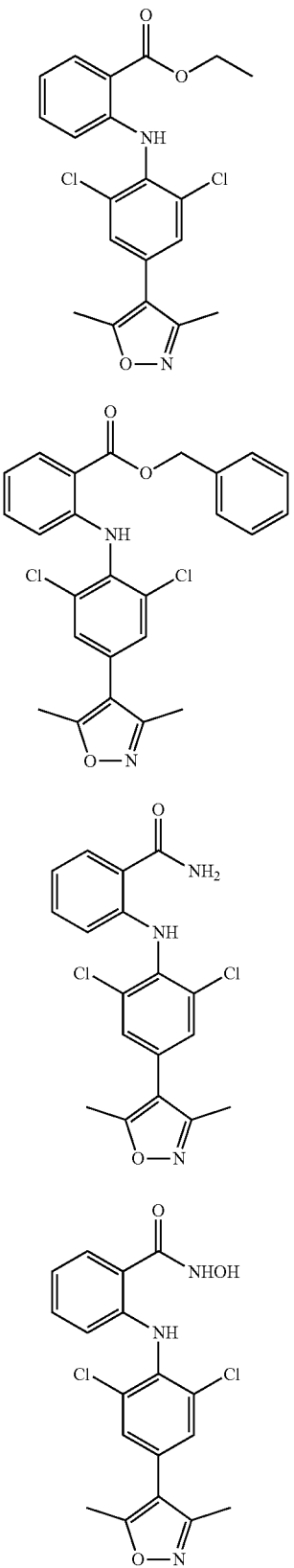
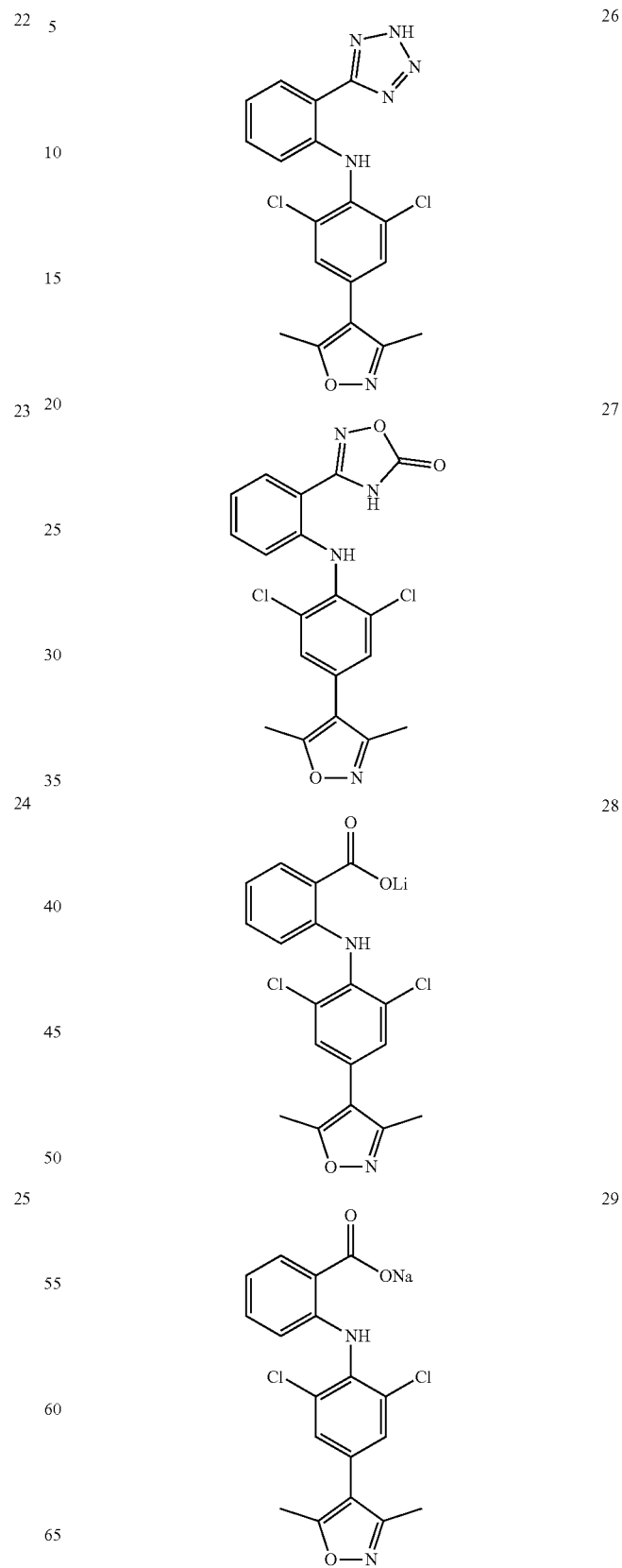

-continued
30
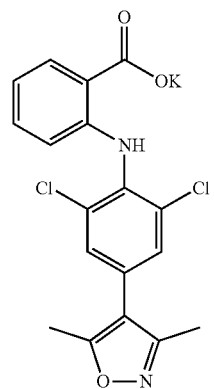
31
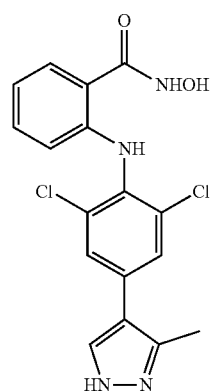
32
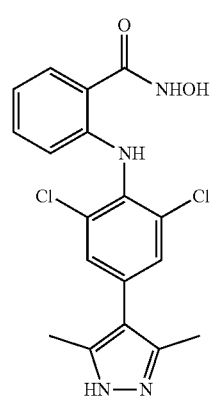
33
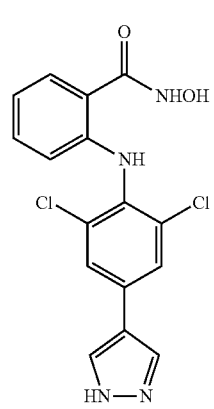
-continued
34
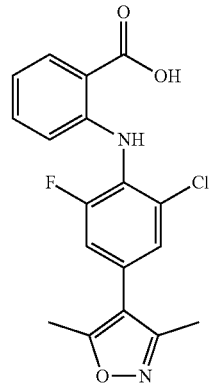
35
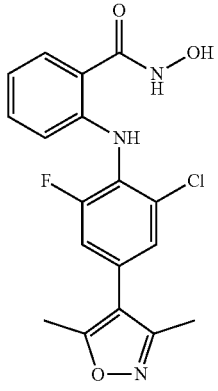
36
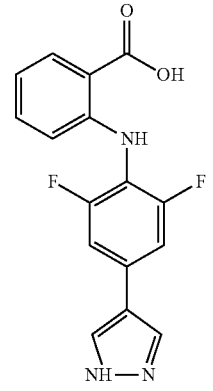
37
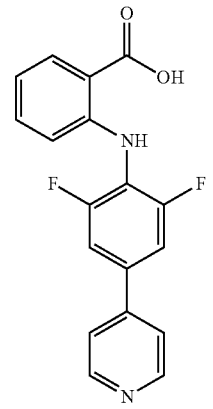

| 38 | 42 |
|---|---|
| 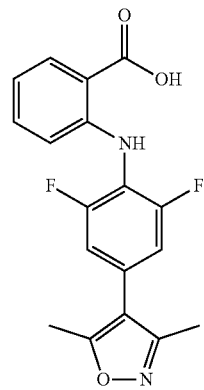 | 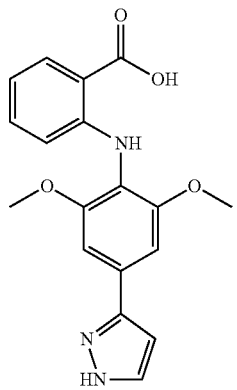 |
| 39 | 43 |
| 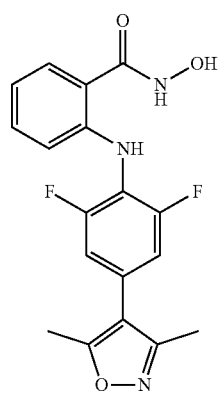 | 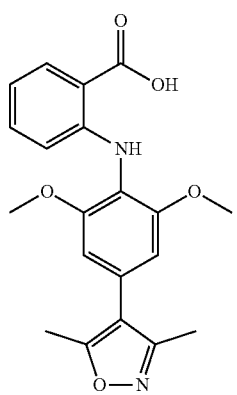 |
| 40 | 44 |
| 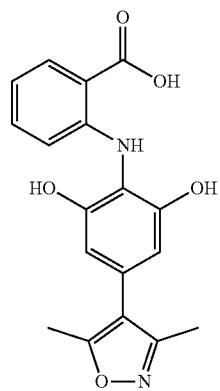 | 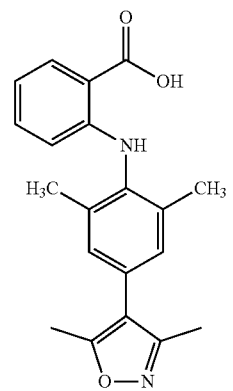 |
| 41 | 45 |
| 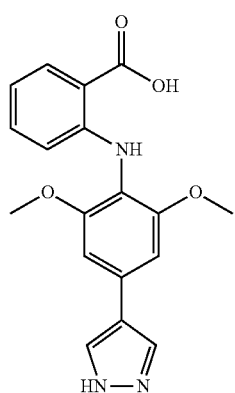 | 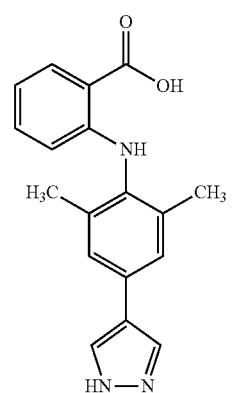 |

| 46 | 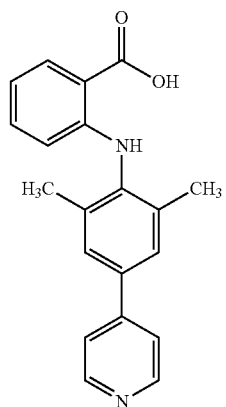 | 50 | 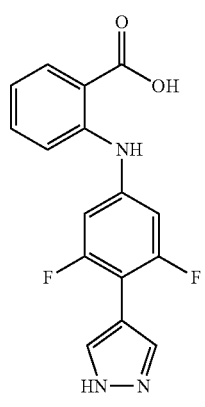 |
| --- | --- | --- | --- |
| 47 | 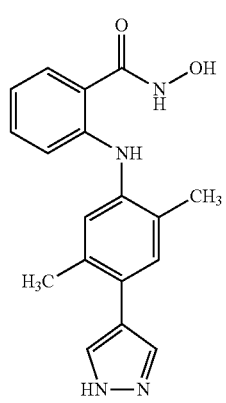 | 51 | 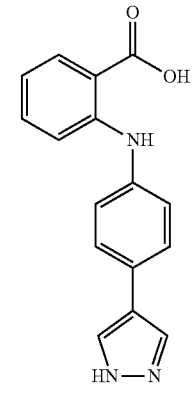 |
| 48 | 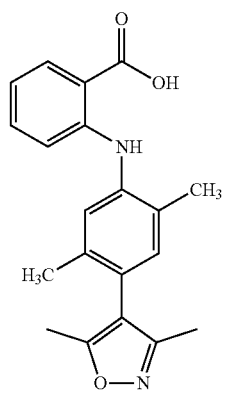 | 52 | 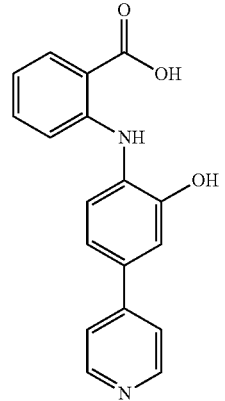 |
| 49 | 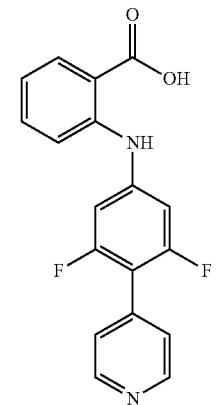 | 53 | 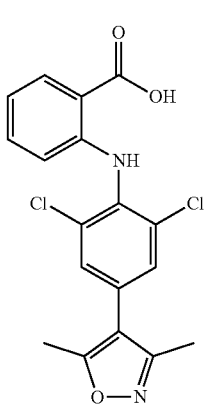 |

51
-continued
54
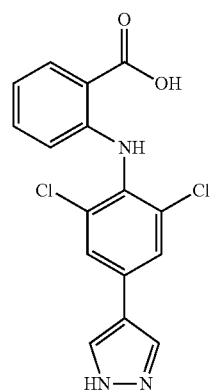
55
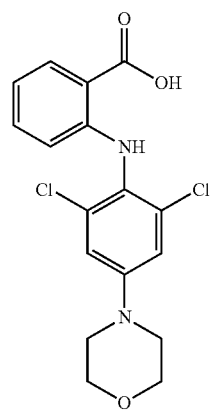
56
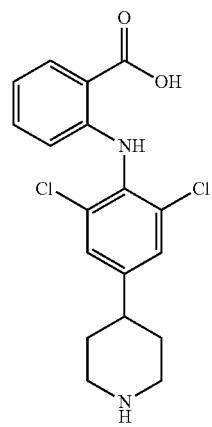
57
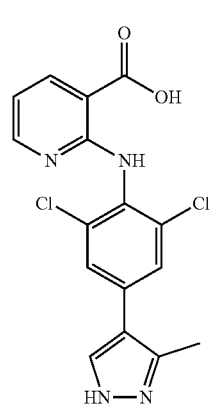
52
-continued
58
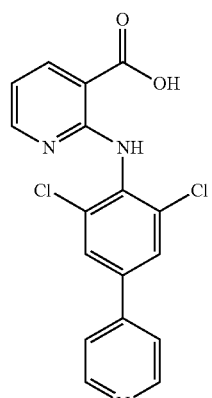
59
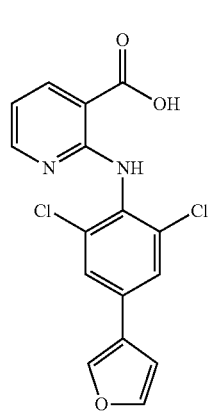
60
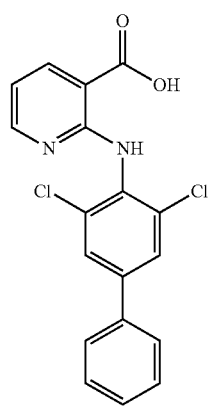
61
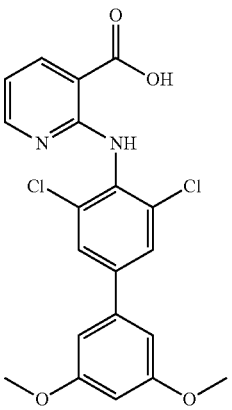

62 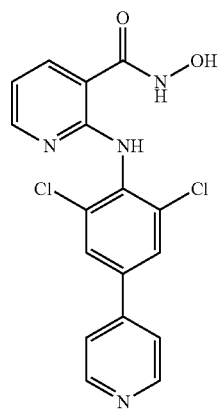
63 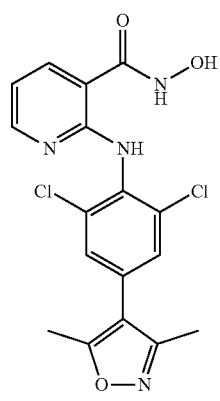
64 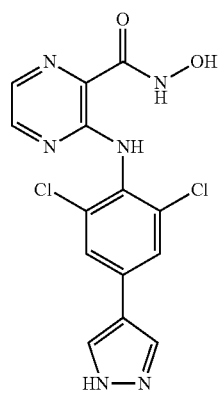
65 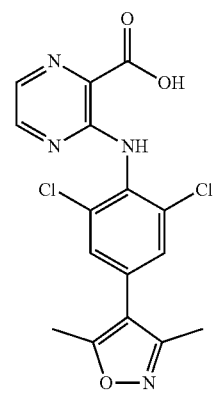
66 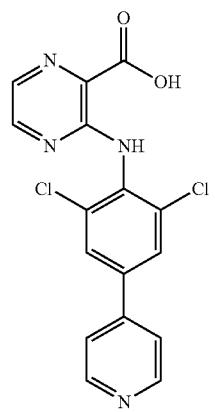
67 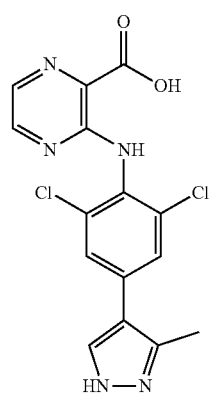
68 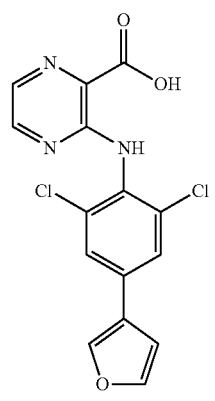
69 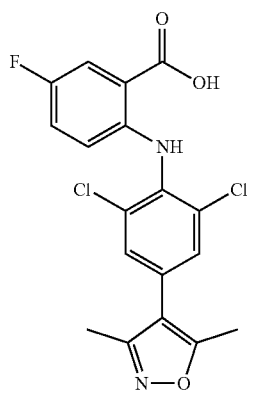

70
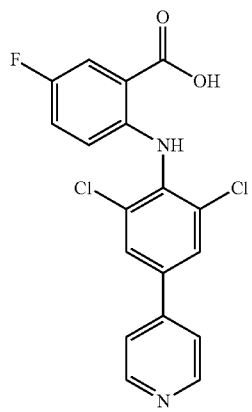
71
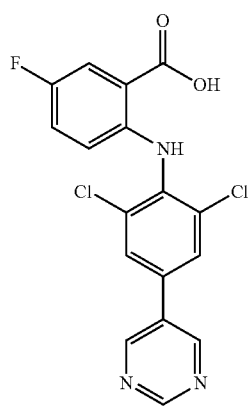
72
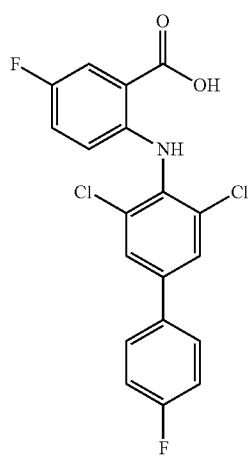
73
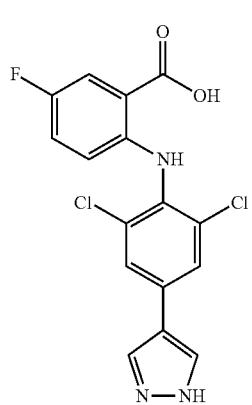
74
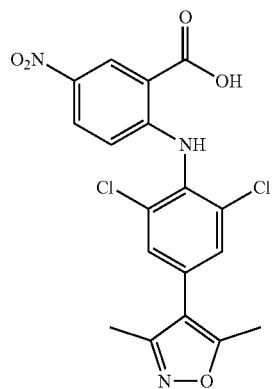
75
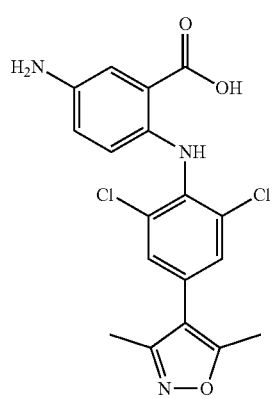
76
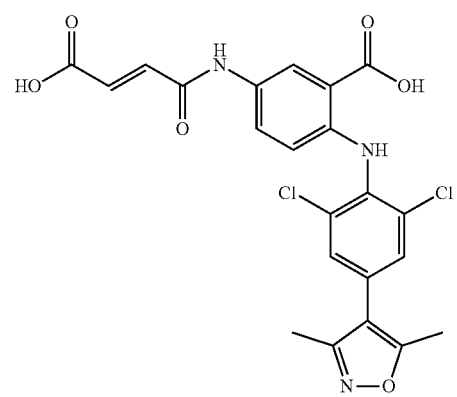
77
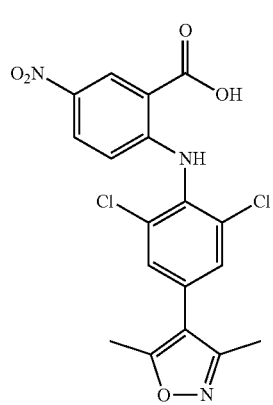

-continued
78
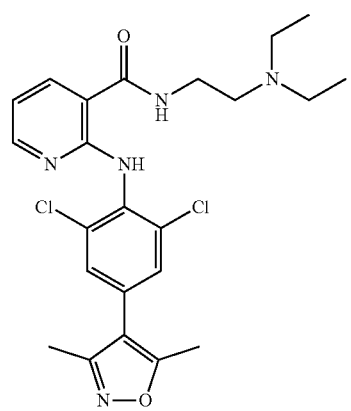
79
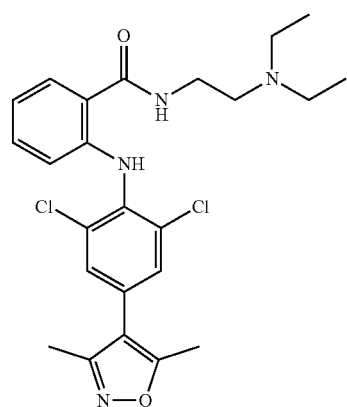
80
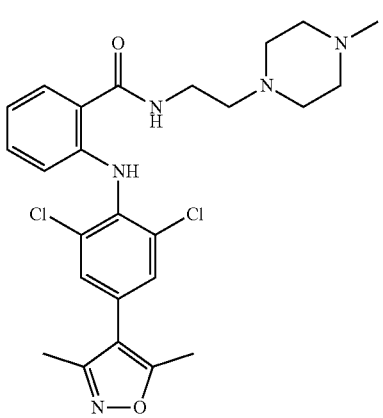
81
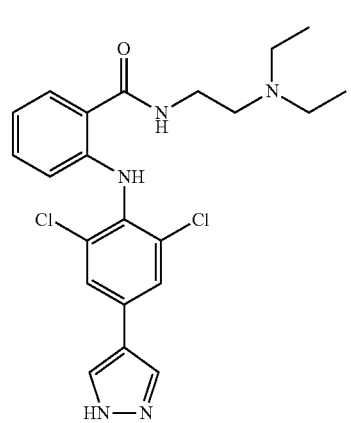
-continued
82
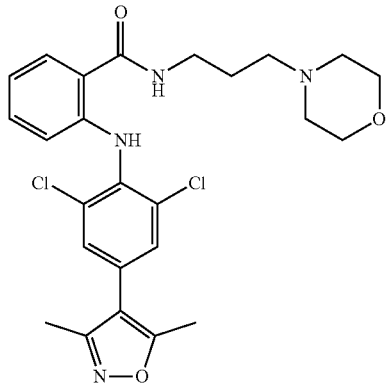
83
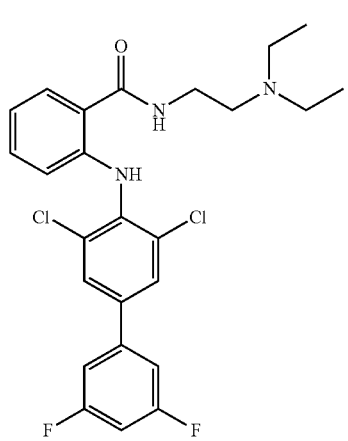
84
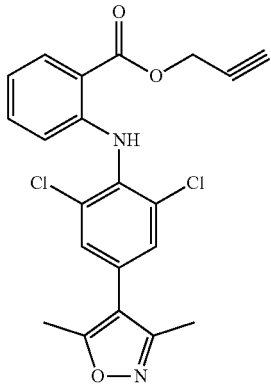
85
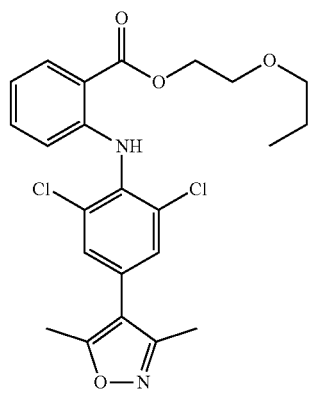

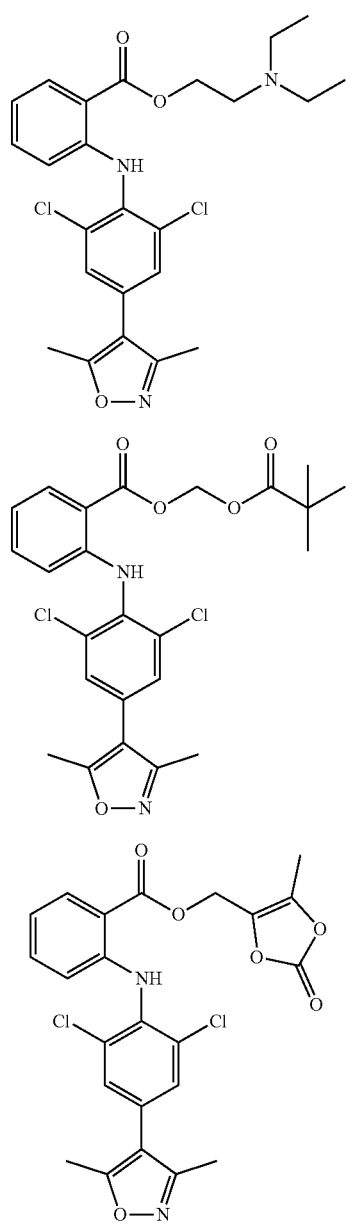

The following is an experiment for inhibiting FTO enzyme activity by 2-(substituted phenylhetero)aromatic formate compound represented by the formula (I).

EXAMPLE 1

Preparation of 2-(Substituted Phenylhetero) Aromatic Formate (Compound 15 and Compound 25)

Compound 25 was synthesized with o-iodobenzoic acid and 4-bromo-2,6-dichloroaniline as starting materials. Ullman coupling was processed under the action of anhydrous copper acetate and N-methylmorpholine, and the compound 15 was prepared by undergoing esterification, Suzuki coupling reaction, and hydrolysis. On this basis, the compound 25 was prepared by hydroxamic acidification, as shown in the following scheme:

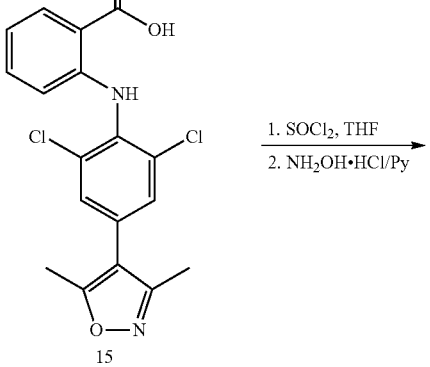

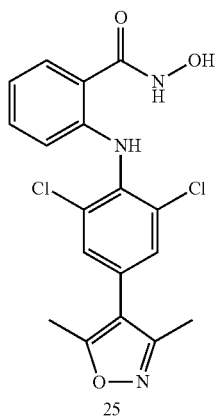

Step 1: o-iodobenzoic acid 30 g (120 mmol, 1.2 eq), 2,6-dichloro-4-bromoaniline 24 g (100 mmol, 1.0 eq), triethylamine (150 mmol, 1.5 eq) and anhydrous copper acetate 9 g (5.0 mmol, 0.5 eq) were dissolved in DMF (500 mL), heated under argon to 120° C. and reacted for 24 h. After the reaction was completed, the mixture was cooled to room temperature, and an equal volume of water was added. The mother liquor was extracted with DCM (300 mL, 3 times), and DMF was washed with water. The organic phase was spin dried, and the column ratio was transited from PE:EA=20:1 to PE:EA=1:1 so as to provide 9.8 g of yellow solid.

Step 2: 3.6 g of 2-((4-bromo-2,6-dichlorophenyl)amino)benzoic acid was dissolved in 200 mL of absolute ethanol. Under ice water bath cooling, 20 mL of concentrated sulfuric acid was added thereto, and heated to 100° C. to react under reflux for 12 hours. After the reaction was completed, the reaction system was cooled to room temperature, and concentrated by evaporation to remove ethanol, then 100 mL of water was added into the system, and neutralized with saturated sodium carbonate until no bubbles were generated. The organic phase was extracted with ethyl acetate (50 mL×3), and the organic phase was combined, and washed with saturated brine (10 mL×3). The organic phase was dried over anhydrous sodium sulfate, filtered, and the filtrate was concentrated and separated by silica gel column to give 3.1 g of white solid ethyl 2-((4-bromo-2,6-dichlorophenyl)amino)benzoate.

Step 3: Ethyl 2-((4-bromo-2,6-dichlorophenyl)amino)benzoate 3.0 g (8.0 mmol, 1.0 eq), 2,5-dimethylisoxazole-4-boronic acid 1.36 g (9.6 mmol, 1.2 eq), catalyst Pd(dppf)Cl$_2$ 584 mg (0.8 mmol, 0.1 eq), and potassium carbonate 1.68 g (12.0 mmol, 1.5 eq) were dissolved in 160 mL of solvent mixture of dioxane and water (4:1/v:v), and heated to 100° C. to react for 24 hours. The mixture was cooled to room temperature, rotary evaporated to remove ½ solvent, extracted with ethyl acetate (50 mL×3), and the organic phase was combined and washed with saturated brine (10 mL×3). The organic phase was dried over anhydrous sodium sulfate, filtered, and the filtrate was concentrated and separated by silica gel column (petroleum ether:ethyl acetate 20:1) to obtain ethyl 2-((2,6-dichloride-4-(3,5-dimethylisoxazole)phenyl)amino)benzoate, as a white solid, 1.98 g.

Step 4: Ethyl 2-((2,6-dichloro-4-(3,5-dimethylisoxazole) phenyl)amino)benzoate 1.98 g (4.4 mmol, 1.0 eq) was dissolved in a mixed solvent of 36 mL tetrahydrofuran and 72 mL absolute ethanol. In an ice water bath, sodium hydroxide 880 mg (22 mmol, 5.0 eq) in water (9 mL) was slowly added drop wise. The mixture was heated to 45° C. to react overnight. After the reaction was completed, the system was cooled to room temperature, and concentrated to remove the organic solvent. After 20 mL of water was added, it was placed in an ice water bath, and pH was adjusted with 2M diluted hydrochloric acid to pH=3, and the resulting suspension was continuously stirred at room temperature for 30 min. After vacuum filtration, the solid was washed with water to provide a white solid of 2-((2,6-dichloro-4-(3,5-dimethylisoxazole)phenyl)amino)benzoic acid, 1.6 g (compound 15).

Step 5: 2-((4-bromo-2,6-dichlorophenyl)amino)benzoic acid 844 mg (2.2 mmol, 1.0 eq) was dissolved in 22 mL of thionyl chloride, and the mixture was heated to 65° C. to react for 2 hours. The reaction solution was sampled and added into anhydrous methanol, TLC monitoring was conducted until the reaction was completed, and the reaction mixture was spin dried to provide yellow solid of acid chloride for further use. Hydroxylamine hydrochloride 152 mg (2.2 mmol, 1.0 eq) was weighted and dissolved in a mixture of ethyl acetate and water 33 mL (2:1/v:v), placed in an ice water bath, and potassium carbonate 608 mg (4.4 mmol, 2.0 eq) was added and reacted at room temperature for one hour. The freshly prepared hydroxylamine solution was placed in an ice water bath, and acyl chloride (2.2 mmol, 1.0 eq) in 10 mL of ethyl acetate was slowly added via a constant pressure dropping funnel, and reacted at room temperature for two hours. After rotary evaporation and concentration, the mixture was pulped to provide 623 mg of brown solid.

Other 2-(substituted phenylhetero) aromatic formate compounds having a core structure of pyridine or pyrazine were prepared in a similar manner to that of Example 1 by using the corresponding starting materials.

NMR hydrogen spectroscopy data for 2-(substituted phenylhetero)aromatic formate compounds:

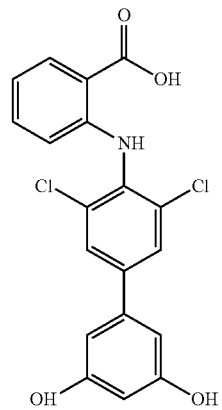

1

$^1$H NMR (300 MHz, d$^6$-DMSO) δ 13.12 (s, 1H), 9.52 (s, 1H), 9.42 (s, 1H), 7.91 (d, J=7.8 Hz, 1H), 7.73 (s, 2H), 7.35 (t, J=7.5 Hz, 1H), 6.80 (t, J=7.4 Hz, 1H), 6.53 (s, 2H), 6.31 (d, J=4.3 Hz, 2H).

| 63 | 64 |
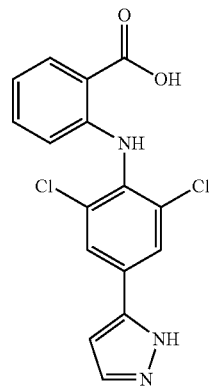
2
¹H NMR (300 MHz, d⁶-DMSO) δ 13.15 (s, 1H), 9.51 (s, 1H), 8.03 (s, 2H), 7.91 (d, J=7.8 Hz, 1H), 7.81 (s, 1H), 7.33 (d, J=7.2 Hz, 1H), 6.92 (d, J=2.2 Hz, 1H), 6.79 (t, J=7.5 Hz, 1H), 6.30 (d, J=8.3 Hz, 1H).
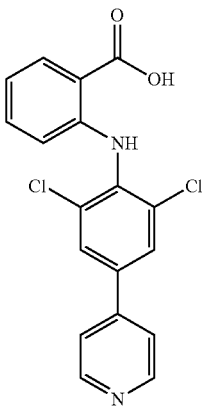
5
¹H NMR (300 MHz, d⁶-DMSO) δ 13.23 (s, 1H), 9.61 (s, 1H), 8.69 (s, 2H), 8.10 (s, 2H), 7.92 (d, J=7.7 Hz, 1H), 7.85 (d, J=5.3 Hz, 2H), 7.36 (t, J=7.6 Hz, 1H), 6.82 (t, J=7.6 Hz, 1H), 6.33 (d, J=8.5 Hz, 1H).
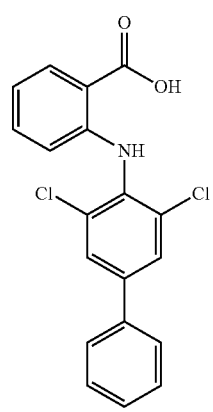
3
¹H NMR (300 MHz, d⁶-DMSO) δ 13.19 (s, 1H), 9.55 (s, 1H), 7.92 (d, J=7.1 Hz, 3H), 7.79 (d, J=7.5 Hz, 2H), 7.47 (dq, J=14.0, 7.0 Hz, 3H), 7.35 (t, J=7.8 Hz, 1H), 6.80 (t, J=7.6 Hz, 1H), 6.32 (d, J=8.3 Hz, 1H).
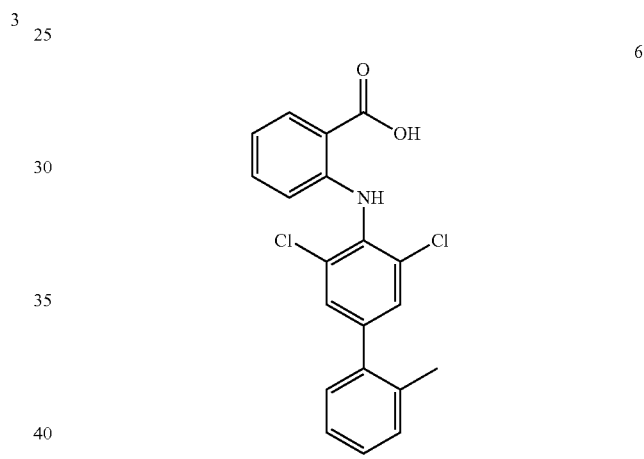
6
¹H NMR (300 MHz, d⁶-DMSO) δ 13.18 (s, 1H), 9.57 (s, 1H), 7.92 (d, J=7.7 Hz, 1H), 7.59 (s, 2H), 7.35 (dd, J=20.3, 8.8 Hz, 5H), 6.81 (t, J=7.5 Hz, 1H), 6.34 (d, J=8.4 Hz, 1H), 2.30 (s, 3H).
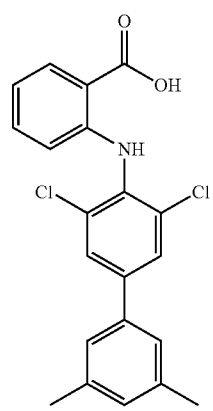
4
¹H NMR (300 MHz, d⁶-DMSO) δ 13.14 (s, 1H), 9.55 (s, 1H), 7.96-7.85 (m, 3H), 7.40 (s, 2H), 7.35 (t, J=7.9 Hz, 1H), 7.06 (s, 1H), 6.80 (t, J=7.7 Hz, 1H), 6.30 (d, J=8.4 Hz, 1H).
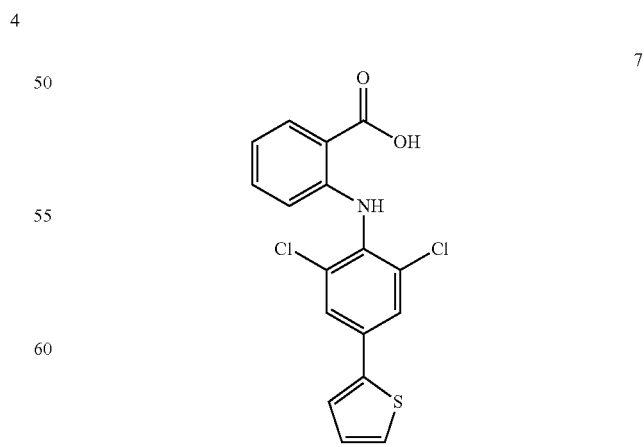
7
¹H NMR (300 MHz, d⁶-DMSO) δ 13.17 (s, 1H), 9.51 (s, 1H), 7.91 (d, J=8.1 Hz, 1H), 7.88 (s, 2H), 7.73 (d, J=2.8 Hz, 1H), 7.67 (d, J=5.0 Hz, 1H), 7.34 (t, J=7.8 Hz, 1H), 7.19 (dd, J=5.0, 3.7 Hz, 1H), 6.80 (t, J=7.4 Hz, 1H), 6.31 (d, J=8.3 Hz, 1H).
8
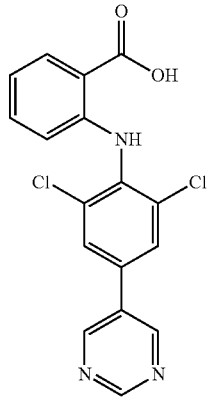
¹H NMR (300 MHz, d⁶-DMSO) δ 9.81 (s, 1H), 9.24 (d, J=8.3 Hz, 3H), 8.14 (s, 2H), 7.93 (d, J=7.7 Hz, 1H), 7.33 (t, J=7.5 Hz, 1H), 6.81 (t, J=7.3 Hz, 1H), 6.31 (d, J=8.3 Hz, 1H).
9
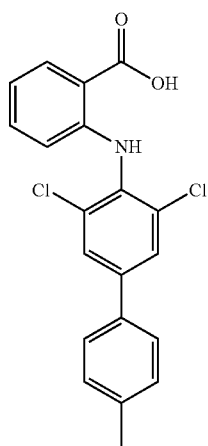
¹H NMR (300 MHz, d⁶-DMSO) δ 13.09 (s, 1H), 9.53 (s, 1H), 7.91 (d, J=9.0 Hz, 3H), 7.69 (d, J=8.0 Hz, 2H), 7.33 (dd, J=16.2, 7.9 Hz, 3H), 6.80 (t, J=7.5 Hz, 1H), 6.31 (d, J=8.3 Hz, 1H), 2.36 (s, 3H).
10
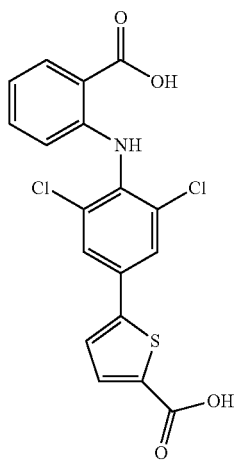
¹H NMR (300 MHz, d⁶-DMSO) δ 13.24 (s, 1H), 9.57 (s, 1H), 7.98 (s, 2H), 7.91 (d, J=8.0 Hz, 1H), 7.81-7.69 (m, 2H), 7.35 (t, J=7.5 Hz, 1H), 6.81 (t, J=7.5 Hz, 1H), 6.32 (d, J=8.5 Hz, 1H).
11
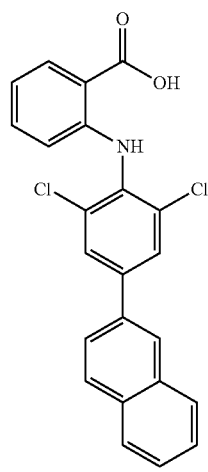
¹H NMR (300 MHz, d⁶-DMSO) δ 13.19 (s, 1H), 9.58 (s, 1H), 8.41 (s, 1H), 8.10 (s, 2H), 8.04 (d, J=8.0 Hz, 2H), 8.00-7.85 (m, 3H), 7.63-7.50 (m, 2H), 7.36 (t, J=7.7 Hz, 1H), 6.81 (t, J=7.6 Hz, 1H), 6.35 (d, J=8.5 Hz, 1H).
12
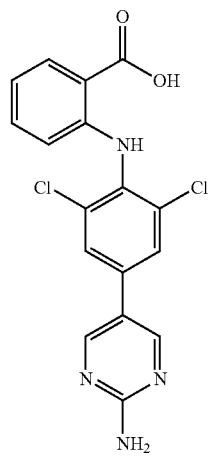
¹H NMR (300 MHz, d⁶-DMSO) δ 13.16 (s, 1H), 9.50 (s, 1H), 8.70 (s, 2H), 7.91 (d, J=11.1 Hz, 3H), 7.34 (t, J=7.7 Hz, 1H), 6.94 (s, 2H), 6.79 (t, J=7.3 Hz, 1H), 6.28 (d, J=8.4 Hz, 1H).
13
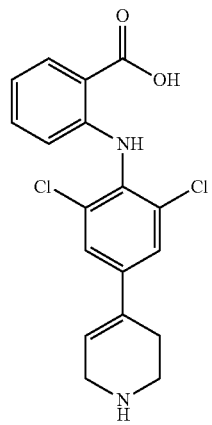

¹H NMR (300 MHz, d⁶-DMSO) δ 13.35 (s, 1H), 9.52 (s, 2H), 9.48-9.34 (m, 1H), 7.90 (d, J=7.7 Hz, 1H), 7.71 (s, 2H), 7.33 (t, J=7.7 Hz, 1H), 6.79 (t, J=7.6 Hz, 1H), 6.42 (s, 1H), 6.25 (d, J=8.4 Hz, 1H), 3.76 (s, 2H), 2.73 (s, 2H).
14
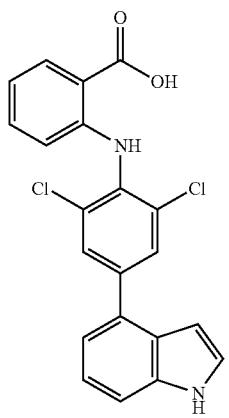
¹H NMR (300 MHz, d⁶-DMSO) δ 13.18 (s, 1H), 11.39 (s, 1H), 9.59 (s, 1H), 7.93 (d, J=7.9 Hz, 1H), 7.85 (s, 2H), 7.49 (s, 2H), 7.37 (t, J=7.7 Hz, 1H), 7.21 (d, J=6.2 Hz, 2H), 6.81 (t, J=7.4 Hz, 1H), 6.61 (s, 1H), 6.39 (d, J=8.4 Hz, 1H).
15
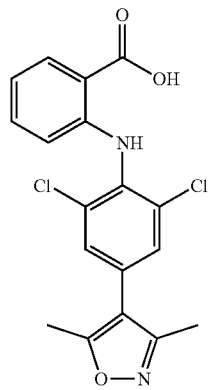
¹H NMR (400 MHz, DMSO) δ 13.21 (s, 1H), 9.62 (s, 1H), 7.92 (d, J=7.7 Hz, 1H), 7.68 (s, 2H), 7.37 (t, J=7.6 Hz, 1H), 6.82 (t, J=7.6 Hz, 1H), 6.35 (d, J=8.2 Hz, 1H), 2.47 (s, 3H), 2.29 (s, 3H).
16
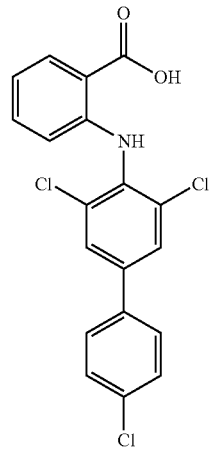
¹H NMR (300 MHz, d⁶-DMSO) δ 13.17 (s, 1H), 9.56 (s, 1H), 7.95 (s, 2H), 7.92 (d, J=7.9 Hz, 1H), 7.84 (d, J=8.6 Hz, 2H), 7.55 (d, J=8.6 Hz, 2H), 7.35 (t, J=7.8 Hz, 1H), 6.81 (t, J=7.5 Hz, 1H), 6.31 (d, J=8.4 Hz, 1H).
17
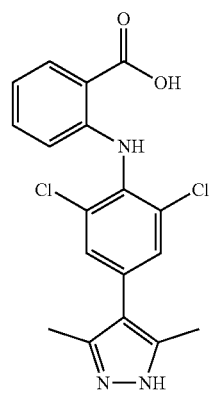
¹H NMR (500 MHz, d⁶-DMSO) δ 13.35 (s, 1H), δ 9.54 (s, 1H), 8.24-8.14 (m, 1H), 8.05-7.99 (m, 1H), 7.82-7.77 (m, 2H), 7.70-7.64 (m, 1H), 7.24 (dt, J=7.0, 3.8 Hz, 1H), 2.13-2.00 (m, 3H), 1.82-1.65 (m, 3H).
18
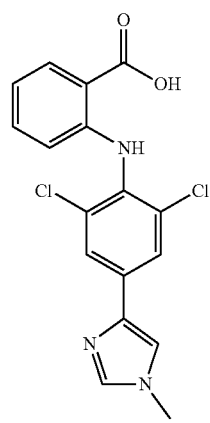

¹H NMR (500 MHz, d⁶-DMSO) δ 13.17 (s, 1H), δ 9.58 (s, 1H), 8.09-8.04 (m, 1H), 7.96-7.91 (m, 1H), 7.82-7.77 (m, 2H), 7.67-7.59 (m, 2H), 7.59-7.55 (m, 1H), 7.26-7.19 (m, 1H), 3.86-3.67 (m, 3H).
19
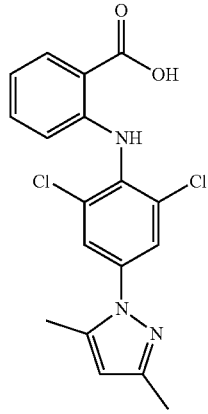
¹H NMR (500 MHz, d⁶-DMSO) δ 13.20 (s, 1H), δ 9.52 (s, 1H), 8.15-8.08 (m, 1H), 8.00 (dd, J=5.3, 2.2 Hz, 1H), 7.98-7.93 (m, 2H), 7.69-7.61 (m, 1H), 7.28-7.19 (m, 1H), 6.26-6.18 (m, 1H), 2.25-2.05 (m, 3H), 2.05-1.91 (m, 3H).
20
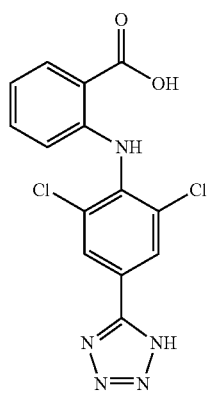
¹H NMR (500 MHz, d⁶-DMSO) δ 13.19 (s, 1H), δ 9.57 (s, 1H), 8.11-8.04 (m, 1H), 8.03-7.97 (m, 1H), 7.83-7.76 (m, 2H), 7.68-7.58 (m, 1H), 7.25-7.17 (m, 1H).
21
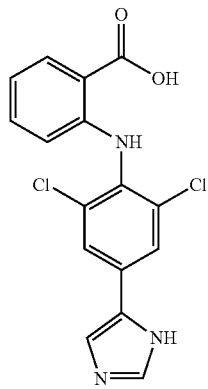
¹H NMR (500 MHz, d⁶-DMSO) δ 13.25 (s, 1H), δ 9.57 (s, 1H), 8.19-8.07 (m, 1H), 7.99-7.92 (m, 1H), 7.72-7.67 (m, 2H), 7.66-7.60 (m, 1H), 7.32-7.19 (m, 1H), 7.13-7.04 (m, 1H), 7.05-6.96 (m, 1H), 5.62-5.54 (m, 1H).
26
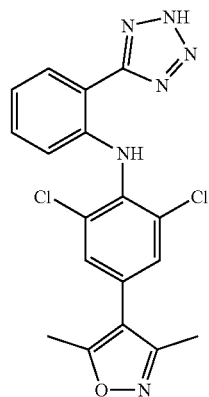
¹H NMR (400 MHz, d⁶-DMSO) δ 9.90 (s, 1H), 8.04 (d, J=7.2 Hz, 1H), 7.66 (s, 2H), 7.21 (t, J=7.2 Hz, 1H), 6.91 (t, J=7.2 Hz, 1H), 6.42 (d, J=7.6 Hz, 1H), 2.47 (s, 3H), 2.29 (s, 3H).
27
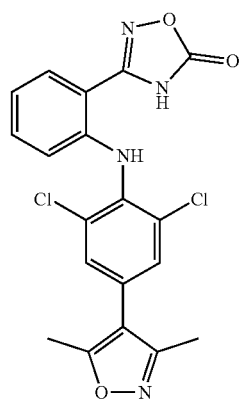
¹H NMR (500 MHz, d⁶-DMSO) δ 13.35 (s, 1H), δ 9.54 (s, 1H), 8.24-8.14 (m, 1H), 8.05-7.99 (m, 1H), 7.82-7.77 (m, 2H), 7.70-7.64 (m, 1H), 7.24 (dt, J=7.0, 3.8 Hz, 1H), 2.13-2.00 (m, 3H), 1.82-1.65 (m, 3H).
34
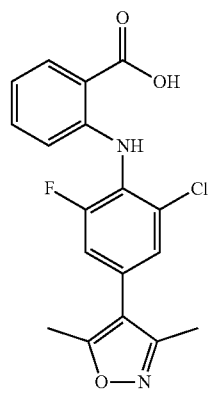
¹H NMR (400 MHz, DMSO) δ 13.28 (s, 1H), 9.54 (s, 1H), 7.92 (dd, J=7.9, 1.5 Hz, 1H), 7.54 (s, 1H), 7.48 (dd, J=11.0, 1.8 Hz, 1H), 7.44-7.36 (m, 1H), 6.84 (t, J=7.5 Hz, 1H), 6.53 (dd, J=8.3, 3.9 Hz, 1H), 2.47 (s, 3H), 2.29 (s, 3H).
¹H NMR (500 MHz, Chloroform) δ 8.38 (s, 1H), 8.08 (s, 1H), 7.92 (s, 1H), 7.62 (s, 1H), 7.22 (s, 1H), 6.75-6.67 (m, 2H), 6.20 (s, 2H), 2.30 (s, 6H).
37
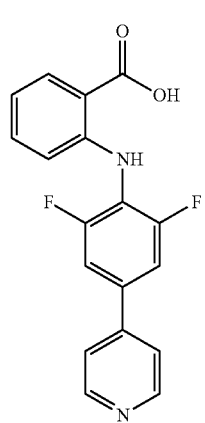
¹H NMR (400 MHz, DMSO) δ 13.32 (s, 1H), 9.53 (s, 1H), 8.69 (s, 2H), 7.88 (dd, J=37.0, 8.4 Hz, 5H), 7.42 (t, J=7.8 Hz, 1H), 6.86 (t, J=7.7 Hz, 1H), 6.62 (d, J=7.7 Hz, 1H).
41
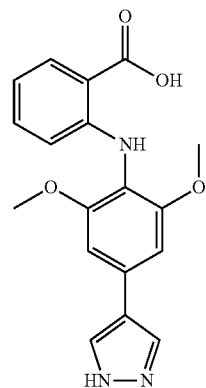
¹H NMR (400 MHz, DMSO) δ 13.32 (s, 1H), 9.53 (s, 1H), 8.69 (s, 2H), 7.88 (dd, J=37.0, 8.4 Hz, 5H), 7.42 (t, J=7.8 Hz, 1H), 6.86 (t, J=7.7 Hz, 1H), 6.62 (d, J=7.7 Hz, 1H).
38
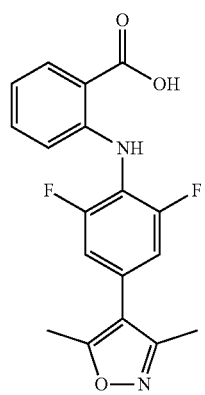
¹H NMR (400 MHz, DMSO) δ 13.32 (s, 1H), 9.53 (s, 1H), 8.69 (s, 2H), 7.88 (dd, J=37.0, 8.4 Hz, 5H), 7.42 (t, J=7.8 Hz, 1H), 6.86 (t, J=7.7 Hz, 1H), 6.62 (d, J=7.7 Hz, 1H).
43
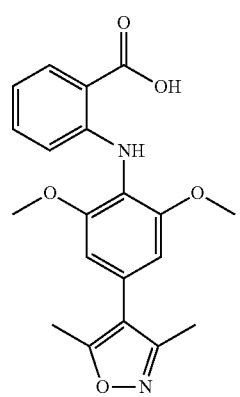
¹H NMR (400 MHz, DMSO) δ 13.32 (s, 1H), 9.53 (s, 1H), 8.69 (s, 2H), 7.88 (dd, J=37.0, 8.4 Hz, 5H), 7.42 (t, J=7.8 Hz, 1H), 6.86 (t, J=7.7 Hz, 1H), 6.62 (d, J=7.7 Hz, 1H).
40
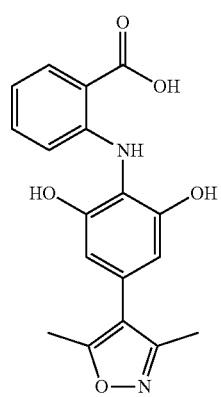
44
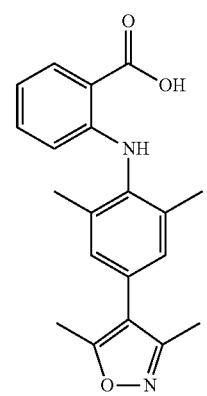

¹H NMR (400 MHz, DMSO) δ 13.32 (s, 1H), 9.53 (s, 1H), 8.69 (s, 2H), 7.88 (dd, J=37.0, 8.4 Hz, 5H), 7.42 (t, J=7.8 Hz, 1H), 6.86 (t, J=7.7 Hz, 1H), 6.62 (d, J=7.7 Hz, 1H).
¹H NMR (400 MHz, DMSO) δ 13.32 (s, 1H), 9.53 (s, 1H), 8.69 (s, 2H), 7.88 (dd, J=37.0, 8.4 Hz, 5H), 7.42 (t, J=7.8 Hz, 1H), 6.86 (t, J=7.7 Hz, 1H), 6.62 (d, J=7.7 Hz, 1H).
47
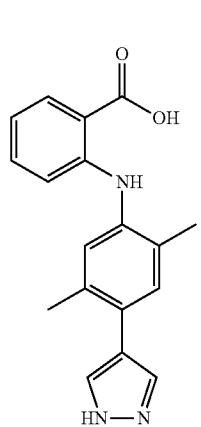
51
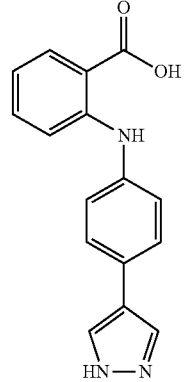
¹H NMR (400 MHz, DMSO) δ 13.34-12.95 (m, 1H), 9.63 (s, 1H), 8.63 (s, 2H), 7.93 (d, J=7.9 Hz, 1H), 7.41 (d, J=7.2 Hz, 4H), 7.32 (s, 1H), 7.22 (s, 1H), 7.07 (d, J=8.3 Hz, 1H), 6.79 (t, J=7.6 Hz, 1H), 2.24 (d, J=7.0 Hz, 7H).
¹H NMR (400 MHz, DMSO) δ 13.32 (s, 1H), 9.53 (s, 1H), 8.69 (s, 2H), 7.88 (dd, J=37.0, 8.4 Hz, 5H), 7.42 (t, J=7.8 Hz, 1H), 6.86 (t, J=7.7 Hz, 1H), 6.62 (d, J=7.7 Hz, 1H).
49
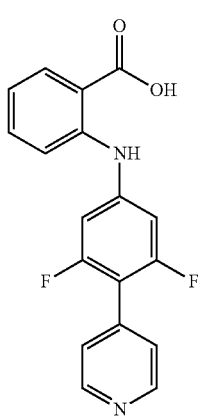
53
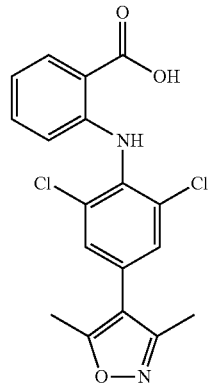
¹H NMR (400 MHz, DMSO) δ 13.32 (s, 1H), 9.53 (s, 1H), 8.69 (s, 2H), 7.88 (dd, J=37.0, 8.4 Hz, 5H), 7.42 (t, J=7.8 Hz, 1H), 6.86 (t, J=7.7 Hz, 1H), 6.62 (d, J=7.7 Hz, 1H).
¹H NMR (400 MHz, DMSO) δ 13.02 (s, 1H), 7.86 (dd, J=7.7, 1.7 Hz, 1H), 7.71 (s, 2H), 7.51-7.42 (m, 1H), 7.18 (t, J=7.1 Hz, 1H), 6.59 (d, J=7.8 Hz, 1H), 2.46 (s, 3H), 2.28 (s, 3H).
50
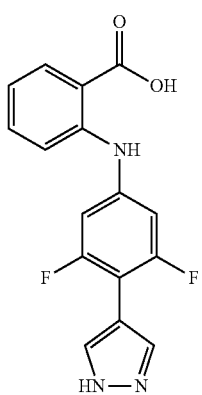
54
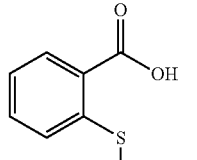

¹H NMR (300 MHz, DMSO) δ 13.34-13.01 (m, 1H), 8.06-7.96 (m, 2H), 0.00 (s, 1H), 0.00 (t, J=5.8, 5.8 Hz, 1H), 0.00 (t, J=7.5, 7.5 Hz, 1H), 0.00 (t, J=7.8, 7.8 Hz, 1H).
¹H NMR (400 MHz, DMSO) δ 13.59 (s, 1H), 9.63 (s, 1H), 8.39 (s, 1H), 8.22 (dt, J=6.8, 1.9 Hz, 2H), 7.85 (s, 2H), 7.79 (t, J=1.7 Hz, 1H), 7.13 (d, J=1.1 Hz, 1H), 6.84 (dd, J=7.6, 4.9 Hz, 1H).
57
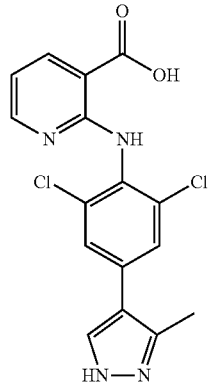
65
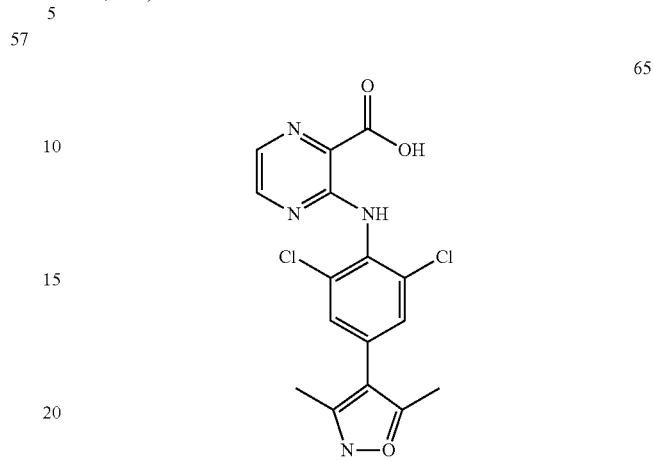
¹H NMR (400 MHz, DMSO) δ 13.06 (s, 1H), 9.87 (s, 1H), 8.25-8.12 (m, 2H), 7.97 (s, 1H), 7.60 (s, 2H), 6.82 (dd, J=7.6, 4.8 Hz, 1H), 2.42 (s, 3H).
¹H NMR (400 MHz, DMSO) δ 11.85 (s, 1H), 8.07 (s, 1H), 7.93 (s, 1H), 7.60 (s, 2H), 2.46 (s, 4H), 2.28 (s, 3H).
58
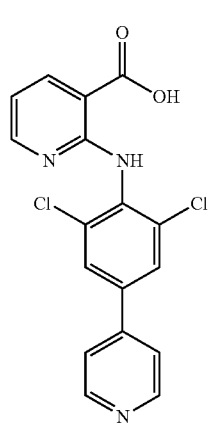
66
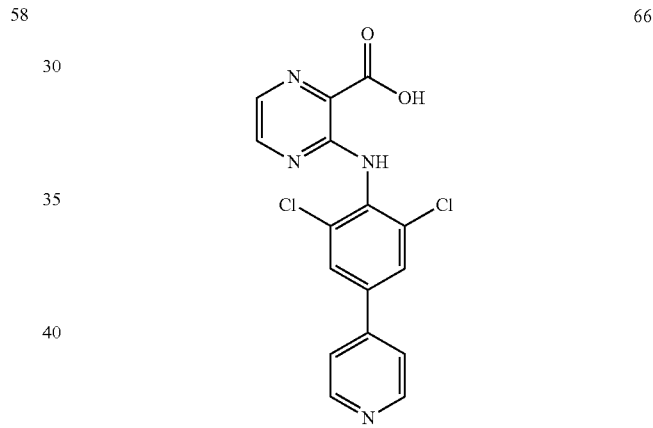
¹H NMR (400 MHz, DMSO) δ 10.02 (s, 1H), 8.69 (s, 2H), 8.21 (dd, J=13.1, 6.2 Hz, 2H), 8.03 (s, 2H), 7.86 (s, 2H), 6.85 (dd, J=7.6, 4.8 Hz, 1H).
¹H NMR (400 MHz, DMSO) δ 9.79 (s, 1H), 8.70 (d, J=6.1 Hz, 2H), 8.32 (d, J=2.2 Hz, 1H), 8.15 (d, J=2.3 Hz, 1H), 8.06 (s, 2H), 7.86 (d, J=6.1 Hz, 2H).
59
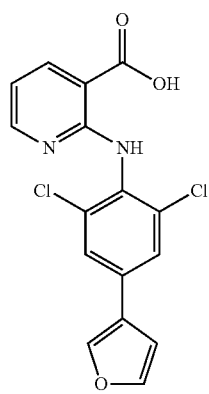
67
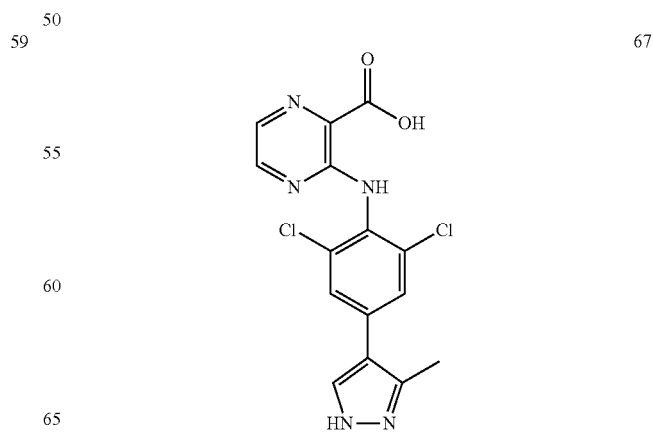

77
¹H NMR (400 MHz, DMSO) δ 9.66 (s, 1H), 8.32 (d, J=2.3 Hz, 1H), 8.13 (d, J=2.3 Hz, 1H), 7.99 (s, 1H), 7.63 (s, 2H), 2.42 (s, 1H).
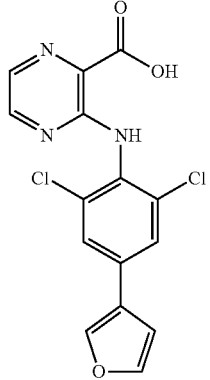
68
¹H NMR (400 MHz, DMSO) δ 10.36 (s, 1H), 8.40 (s, 1H), 8.21 (s, 1H), 8.05 (s, 1H), 7.86 (s, 2H), 7.79 (s, 1H), 7.13 (s, 1H).
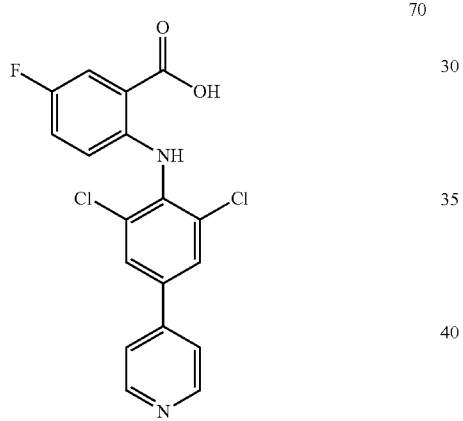
70
¹H NMR (400 MHz, DMSO) δ 9.87 (s, 1H), 8.69 (s, 2H), 8.09 (s, 2H), 7.86 (s, 2H), 7.64 (dd, J=9.5, 3.0 Hz, 1H), 7.22 (td, J=8.8, 3.1 Hz, 1H), 6.34 (dd, J=9.0, 4.5 Hz, 1H).
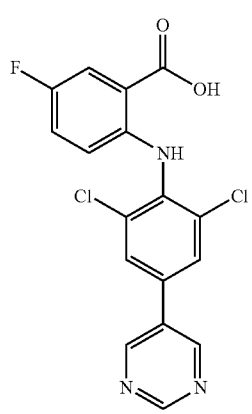
71
78
¹H NMR (400 MHz, DMSO) δ 13.58 (s, 1H), 9.44 (s, 1H), 9.27 (s, 2H), 9.24 (s, 1H), 8.17 (s, 2H), 7.65 (dd, J=9.4, 3.1 Hz, 1H), 7.35-7.21 (m, 1H), 6.35 (dd, J=9.2, 4.5 Hz, 1H).
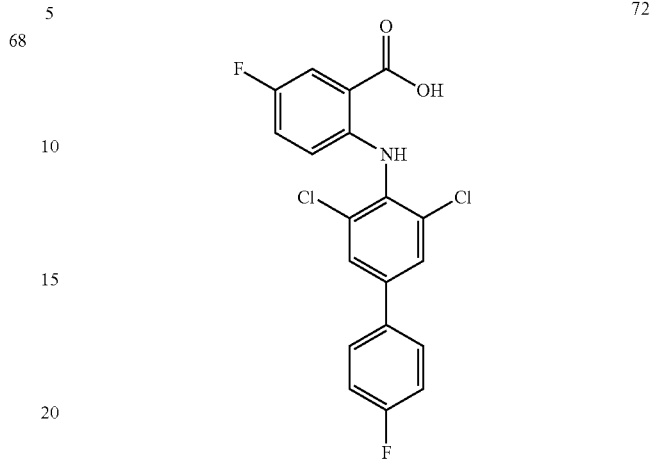
72
¹H NMR (400 MHz, DMSO) δ 13.60 (s, 1H), 9.37 (s, 1H), 9.28 (s, OH), 7.93 (s, 2H), 7.89-7.78 (m, 2H), 7.64 (d, J=6.7 Hz, 1H), 7.42-7.16 (m, 3H), 6.39-6.23 (m, 1H).
73
¹H NMR (400 MHz, DMSO) δ 13.26 (s, 1H), 9.33 (s, 1H), 8.26 (s, 2H), 7.91 (s, 2H), 7.62 (dd, J=9.5, 3.2 Hz, 1H), 7.32-7.17 (m, 1H), 6.30 (dd, J=9.2, 4.5 Hz, 1H).
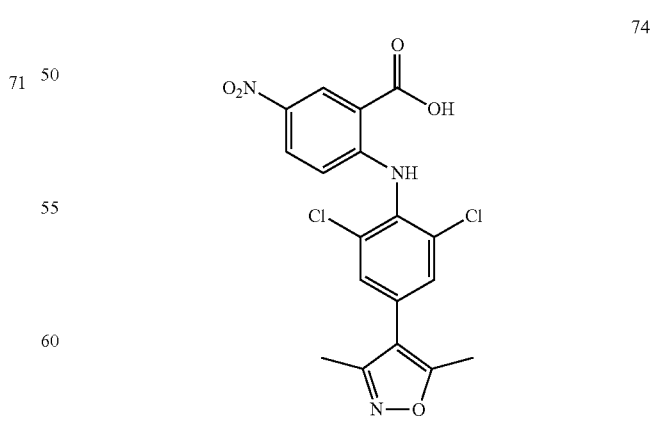
74
¹H NMR (400 MHz, DMSO) δ 10.75 (s, 1H), 8.76 (d, J=2.8 Hz, 1H), 8.17 (dd, J=9.3, 2.8 Hz, 1H), 7.74 (s, 2H), 6.45 (d, J=9.3 Hz, 1H), 2.48 (s, 3H), 2.30 (s, 3H).

79

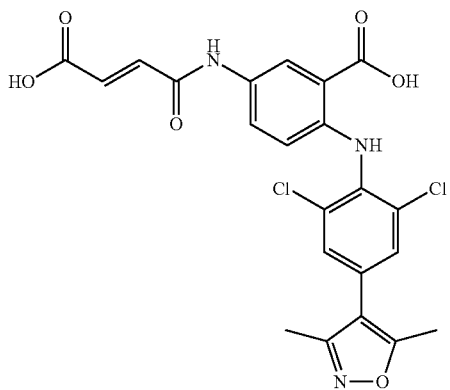

76

¹H NMR (400 MHz, DMSO) δ 13.49-12.92 (m, 1H), 10.48 (s, 1H), 9.51 (s, 1H), 8.35 (d, J=2.6 Hz, 1H), 7.68 (s, 2H), 7.64 (dd, J=9.0, 2.6 Hz, 1H), 7.10 (d, J=15.4 Hz, 1H), 6.64 (d, J=15.4 Hz, 1H), 6.38 (d, J=9.0 Hz, 1H), 2.47 (s, 3H), 2.29 (s, 3H).

NMR hydrogen spectroscopy data for 2-(substituted phenylhetero)aromatic hydroxamic acid compounds:

25

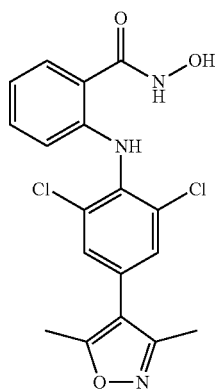

¹H NMR (400 MHz, DMSO) δ 11.33 (s, 1H), 9.52 (s, 1H), 9.17 (s, 1H), 7.62 (s, 2H), 7.50 (d, J=7.6 Hz, 1H), 7.26 (t, J=7.8 Hz, 1H), 6.79 (t, J=7.5 Hz, 1H), 6.34 (d, J=8.2 Hz, 1H), 2.44 (s, 3H), 2.26 (s, 3H).

31

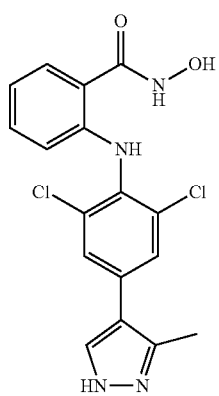

80

¹H NMR (400 MHz, DMSO) δ 11.32 (s, 1H), 9.43 (s, 1H), 7.98 (s, 1H), 7.66 (s, 2H), 7.52 (d, J=7.7 Hz, 1H), 7.26 (t, J=7.8 Hz, 1H), 6.78 (t, J=7.2 Hz, 1H), 6.31 (d, J=8.2 Hz, 1H), 2.42 (s, 3H).

32

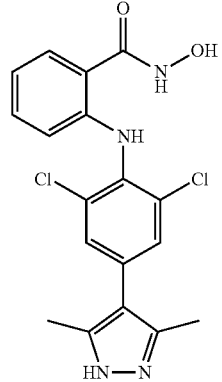

¹H NMR (400 MHz, DMSO) δ 11.33 (s, 1H), 9.49 (s, 1H), 7.53 (d, J=7.6 Hz, 1H), 7.49 (s, 2H), 7.32-7.22 (m, 1H), 6.79 (t, J=7.5 Hz, 1H), 6.34 (d, J=8.3 Hz, 1H), 2.26 (s, 6H).

35

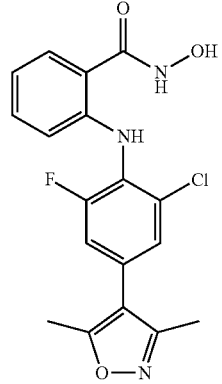

¹H NMR (400 MHz, DMSO) δ 11.38 (s, 1H), 9.47 (s, 1H), 9.22 (s, 1H), 7.52 (d, J=9.3 Hz, 2H), 7.44 (d, J=11.4 Hz, 1H), 7.32 (t, J=7.5 Hz, 1H), 6.84 (t, J=7.3 Hz, 1H), 6.57 (dd, J=8.1, 4.7 Hz, 1H), 2.46 (s, 3H), 2.29 (s, 3H).

62

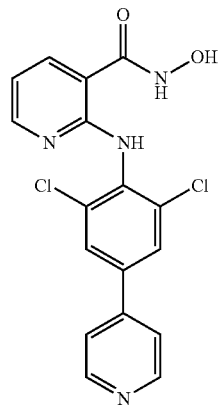

¹H NMR (400 MHz, DMSO) δ 11.57 (s, 1H), 10.06 (s, 1H), 8.86 (s, 2H), 8.19 (s, 2H), 8.15 (s, 3H), 7.95 (d, J=7.6 Hz, 1H), 6.87 (dd, J=7.4, 5.0 Hz, 1H).

Synthesis Step and NMR Hydrogen Spectroscopy Data for 2-(Substituted Phenylhetero)aryl Amide Compounds

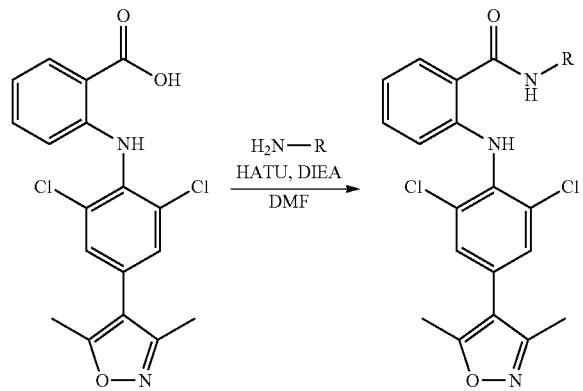

In a 10 mL round bottom flask, acid (0.2 mmoL, 1.0 eq), HATU (0.3 mmoL, 1.5 eq) were dissolved in anhydrous DMF (2 mL) and stirred at room temperature for 5 min. Then DIEA (0.6 mmoL, 3.0 eq) and amine (0.4 mmoL, 2.0 eq) were successively added. After the mixture was reacted at room temperature overnight, water was added into the reaction system, and white turbidity was generated, and the amide target product was obtained by suction filtration and water washing.

24

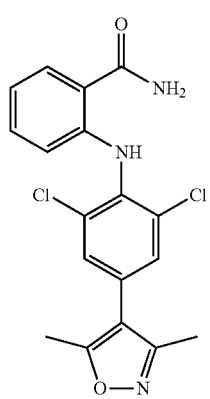

$^1$H NMR (400 MHz, d$^6$-DMSO) δ 10.18 (s, 1H), 8.12 (s, 1H), 7.74 (d, J=7.6 Hz, 1H), 7.63 (s, 2H), 7.51 (s, 1H), 7.27 (t, J=7.6 Hz, 1H), 6.79 (t, J=7.6 Hz, 1H), 6.33 (d, J=8.4 Hz, 1H), 2.45 (s, 3H), 2.27 (s, 3H).

78

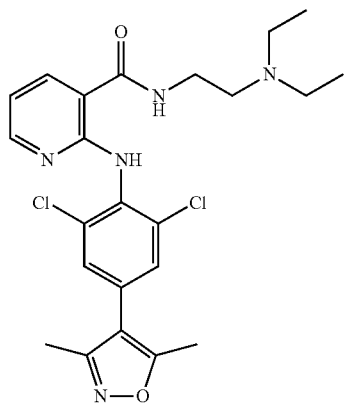

$^1$H NMR (400 MHz, DMSO) δ 8.72 (s, 1H), 8.14 (d, J=4.7 Hz, 1H), 8.06 (d, J=7.7 Hz, 1H), 7.59 (s, 2H), 6.86 (dd, J=7.7, 4.8 Hz, 1H), 2.65-2.53 (m, 5H), 2.45 (s, 4H), 2.28 (s, 3H), 0.98 (t, J=7.1 Hz, 6H).

79

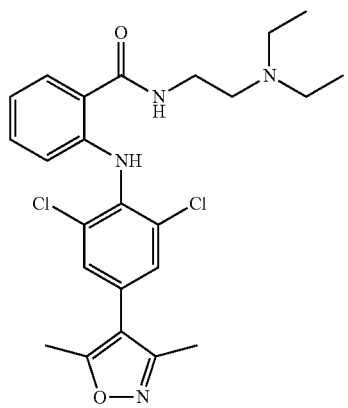

$^1$H NMR (400 MHz, DMSO) δ 9.85 (s, 1H), 8.53 (s, 1H), 7.65 (d, J=9.0 Hz, 3H), 7.28 (t, J=7.8 Hz, 1H), 6.84 (t, J=7.5 Hz, 1H), 6.36 (d, J=8.2 Hz, 1H), 3.35 (d, J=10.2 Hz, 4H), 2.58 (d, J=22.3 Hz, 5H), 2.46 (s, 3H), 2.28 (s, 3H), 0.99 (t, J=7.1 Hz, 6H).

80

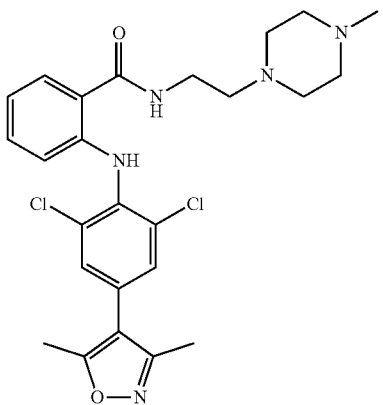

¹H NMR (400 MHz, DMSO) δ 9.72 (s, 1H), 8.53 (t, J=5.5 Hz, 1H), 7.63 (d, J=5.6 Hz, 3H), 7.28 (t, J=7.7 Hz, 1H), 6.84 (t, J=7.4 Hz, 1H), 6.36 (d, J=8.3 Hz, 1H), 2.46 (s, 4H), 2.28 (s, 4H), 2.11 (s, 3H).

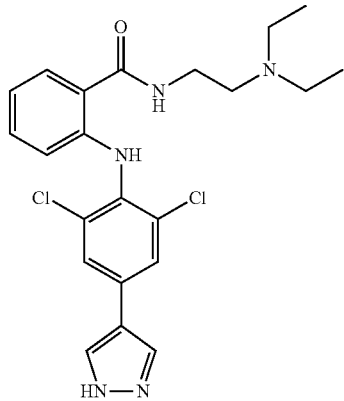

81

¹H NMR (400 MHz, DMSO) δ 13.08 (s, 1H), 9.71 (s, 1H), 8.49 (d, J=5.7 Hz, 1H), 8.39 (s, 1H), 8.09 (s, 1H), 7.88 (s, 2H), 7.64 (d, J=7.8 Hz, 1H), 7.24 (t, J=7.8 Hz, 1H), 6.79 (t, J=7.2 Hz, 1H), 6.28 (d, J=8.3 Hz, 1H), 2.62-2.53 (m, 4H), 0.99 (t, J=7.1 Hz, 6H).

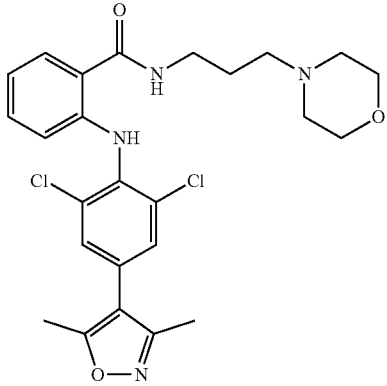

¹H NMR (400 MHz, DMSO) δ 9.88 (s, 1H), 8.67 (d, J=5.3 Hz, 1H), 7.67 (d, J=6.8 Hz, 1H), 7.64 (s, 2H), 6.84 (t, J=7.2 Hz, 1H), 6.36 (d, J=8.1 Hz, 1H), 3.58 (t, J=4.5 Hz, 4H), 3.35-3.27 (m, 2H), 2.46 (s, 3H), 2.36 (t, J=7.0 Hz, 6H), 2.28 (s, 3H), 1.77-1.66 (m, 2H).

83

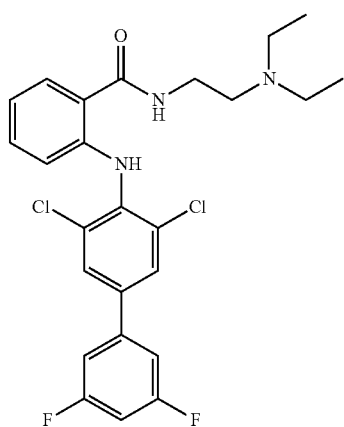

¹H NMR (400 MHz, DMSO) δ 10.14 (s, 1H), 9.89 (s, 1H), 9.00 (s, 1H), 8.05 (s, 2H), 7.81 (d, J=8.1 Hz, 1H), 7.64 (d, J=7.0 Hz, 2H), 7.31 (t, J=8.3 Hz, 2H), 6.87 (t, J=7.5 Hz, 1H), 6.35 (d, J=8.3 Hz, 1H), 3.67 (s, 2H), 3.24 (d, J=26.4 Hz, 6H), 1.26 (d, J=6.7 Hz, 6H).

Synthesis Step and NMR Hydrogen Spectroscopy Data for 2-(Substituted Phenylhetero)aryl Ester Compounds

82

In a 10 mL round bottom flask, acid (0.2 mmoL, 1.0 eq), K₂CO₃ (0.3 mmoL, 1.5 eq) and anhydrous DMF (2 mL) were added, and the corresponding brominated hydrocarbon was added. The mixture was heated to 40° C. and stirred overnight. Water was added into the reaction system, and the reaction mixture was extracted with ethyl acetate. The organic phase was combined and washed sequentially with water and saturated brine, and the organic phase was dried over anhydrous sodium sulfate, concentrated and separated with silica gel column to provide the target product as an ester.

22

¹H NMR (500 MHz, CDCl₃) δ 9.49 (s, 1H), 8.05 (dd, J=8.0, 1.5 Hz, 1H), 7.37-7.33 (m, 1H), 7.32 (s, 2H), 6.86-6.81 (m, 1H), 6.44 (d, J=7.7 Hz, 1H), 4.43 (q, J=7.1 Hz, 2H), 2.49 (s, 3H), 2.34 (s, 3H), 1.46 (t, J=7.1 Hz, 3H).

83
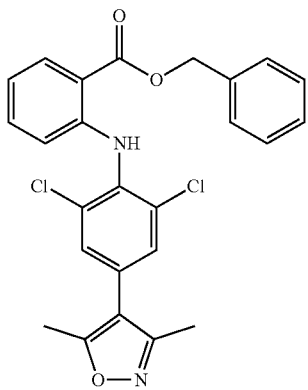
¹H NMR (400 MHz, d⁶-DMSO) δ 9.29 (s, 1H), 7.96 (d, J=6.4 Hz, 1H), 7.68 (s, 2H), 7.51 (d, J=7.8 Hz, 2H), 7.41-7.45 (m, 4H), 6.84 (t, J=7.6 Hz, 1H), 6.36 (d, J=8.0 Hz, 1H), 5.40 (s, 2H), 2.49 (s, 3H), 2.28 (s, 3H).
84
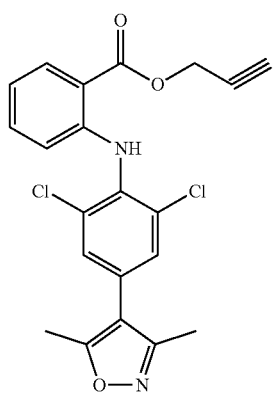
¹H NMR (400 MHz, CDCl₃) δ 9.34 (s, 1H), 8.08 (dd, J=8.1, 1.5 Hz, 1H), 7.42-7.31 (m, 3H), 6.89-6.81 (m, 1H), 6.45 (d, J=8.5 Hz, 1H), 4.98 (d, J=2.5 Hz, 2H), 2.57 (t, J=2.5 Hz, 1H), 2.49 (s, 3H), 2.35 (s, 3H).
85
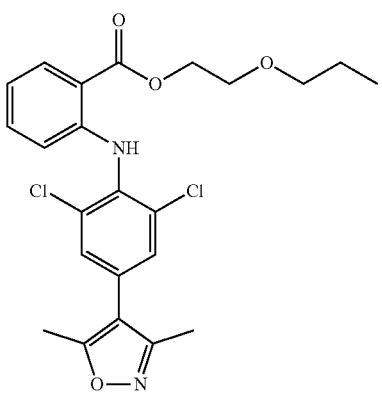
¹H NMR (400 MHz, CDCl₃) δ 9.34 (s, 1H), 8.08 (dd, J=8.1, 1.5 Hz, 1H), 7.42-7.31 (m, 3H), 6.89-6.81 (m, 1H), 6.45 (d, J=8.5 Hz, 1H), 4.98 (d, J=2.5 Hz, 2H), 2.57 (t, J=2.5 Hz, 1H), 2.49 (s, 3H), 2.35 (s, 3H).
86
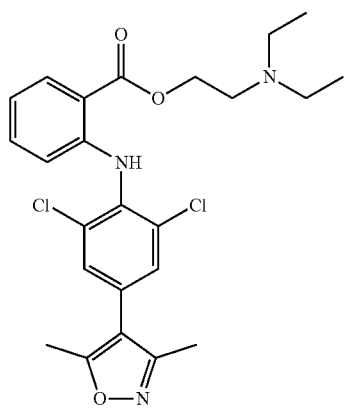
¹H NMR (400 MHz, CDCl₃) δ 9.34 (s, 1H), 8.08 (dd, J=8.1, 1.5 Hz, 1H), 7.42-7.31 (m, 3H), 6.89-6.81 (m, 1H), 6.45 (d, J=8.5 Hz, 1H), 4.98 (d, J=2.5 Hz, 2H), 2.57 (t, J=2.5 Hz, 1H), 2.49 (s, 3H), 2.35 (s, 3H).
87
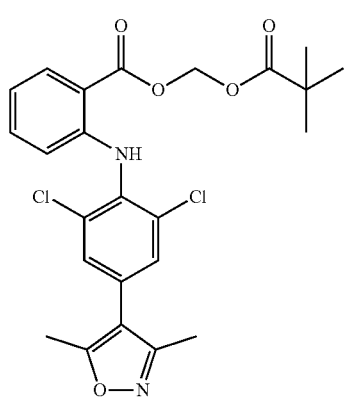
¹H NMR (400 MHz, CDCl₃) δ 9.34 (s, 1H), 8.08 (dd, J=8.1, 1.5 Hz, 1H), 7.42-7.31 (m, 3H), 6.89-6.81 (m, 1H), 6.45 (d, J=8.5 Hz, 1H), 4.98 (d, J=2.5 Hz, 2H), 2.57 (t, J=2.5 Hz, 1H), 2.49 (s, 3H), 2.35 (s, 3H).
88
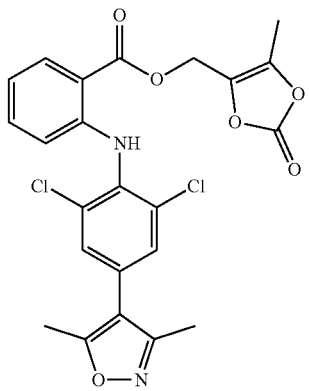
¹H NMR (400 MHz, CDCl₃) δ 9.34 (s, 1H), 8.08 (dd, J=8.1, 1.5 Hz, 1H), 7.42-7.31 (m, 3H), 6.89-6.81 (m, 1H), 6.45 (d, J=8.5 Hz, 1H), 4.98 (d, J=2.5 Hz, 2H), 2.57 (t, J=2.5 Hz, 1H), 2.49 (s, 3H), 2.35 (s, 3H).

Biological Example 1 Determination of FTO Inhibitory Activity

High purity FTO protein was obtained by nickel column affinity chromatography purification.

The reaction system for FTO enzyme inhibition was as follows: 50 mM Tris.HCl, pH 7.5, 0.3 µM FTO, 1 µM 39 nt-m$^6$A modified double-stranded DNA, 300 µM 2 OG, 280 µM (NH$_4$)$_2$Fe(SO$_4$)$_2$, 2 mM L-ascorbic acid and different concentrations of compounds. After incubation at room temperature for 2 hrs, the reaction system was then slowly heated to 65° C. to inactivate, and 1 µM 39 nt of antisense strand DNA was added to anneal, thereby forming double strands. 8 ul of reaction solution was taken, and the double-stranded substrate was digested with methylation-sensitive enzyme DpnII, and the digested sample was detected by 15% non-denaturing polyacrylamide electrophoresis. After Gel-Red dyeing, photos were taken with gel imaging system. The obtained band was subjected to gray scale reading to obtain inhibition rate.

The following were the inhibition rate on FTO enzyme activity by 2-(substituted phenylhetero)aromatic acid compounds represented by the formula (I) and the derivatives thereof at 50 µM concentration.

In vitro inhibition rate on FTO by the compounds (50 µM):

| Compound | Inhibition rate |
| --- | --- |
| 1 | 85% |
| 2 | 80% |
| 4 | 88% |
| 6 | 88% |
| 8 | 90% |
| 11 | 100% |
| 12 | 100% |
| 14 | 100% |
| 25 | 46% |
| 28 | 100% |
| 29 | 100% |
| 30 | 100% |
| 31 | 70% |
| 32 | 62% |
| 33 | 63% |
| 36 | 28% |
| 37 | 31% |
| 38 | 100% |
| 39 | 90% |
| 40 | 100% |
| 42 | 79% |
| 44 | 100% |
| 45 | 100% |
| 46 | 100% |
| 47 | 48% |
| 49 | 100% |
| 52 | 90% |
| 55 | 100% |
| 56 | 45% |
| 57 | 100% |
| 59 | 100% |
| 62 | 28% |
| 63 | 35% |
| 64 | 68% |
| 65 | 88% |
| 70 | 81% |
| 71 | 70% |
| 73 | 84% |
| 74 | 75% |
| 75 | 58% |
| 80 | 29% |
| 81 | 67% |
| 82 | 29% |
| 22 | 32% |
| 23 | 36% |
| 84 | 34% |
| 85 | 30% |
| 86 | 31% |
| 87 | 31% |
| 88 | 34% |

The IC$_{50}$ value of 2-(substituted phenylhetero)aromatic formic acid and the derivatives thereof as FTO Inhibitors for inhibition of enzyme activity:

| Compound | IC$_{50}$ (µM) |
| --- | --- |
| 1 | 0.7 |
| 2 | <5 |
| 5 | <5 |
| 10 | <1 |
| 15 | 0.06 |
| 17 | <1 |
| 25 | <1 |
| 26 | 0.4 |
| 27 | <1 |
| 28 | <1 |
| 29 | <1 |
| 30 | <1 |
| 31 | <5 |
| 32 | <1 |
| 33 | <1 |
| 38 | <1 |
| 39 | <1 |
| 45 | <5 |
| 55 | <5 |

The inhibitory activity of the compounds of the present application is significantly improved over the existing FTO inhibitory compounds, and the FTO inhibitory activity of some compounds can even reach up to nmol level.

Biological Example 2

The following was a study of the cytotoxicity study of compound of 2-(substituted phenylhetero)aromatic formic acid of formula (I) and its derivatives as FTO inhibitors on solid tumors including human small cell lung cancer cell lines (SCLC-21H), human bone marrow rhabdomyosarcoma cell line (RH30) and pancreatic cancer cell Line (KP3):

SCLC-21H, RH30 and KP3 solid tumor cell lines were cultivated separately, and seeded at 5000 cells per well in 96 well plates. The cells were cultured until the cells were adherent, and different compounds were added and the cultivation was continued for 72 hours. 10 uL of MTS solution was directly added and the mixture was incubated for 4 h, and the absorbance was measured at 490 nm. The inhibition rate was calculated by using the DMSO group as a control.

The following were the cell cytotoxicity (i.e., inhibition rate) of 2-(substituted phenylhetero)aromatic formic acid compounds as FTO inhibitor shown in general formula (I) on SCLC-21H, RH30, and KP3 at a concentration of 50 µM and at 72 h time point.

Summary of activity of compounds (cell inhibition rate at a concentration of 50 µM):

| Compound | Inhibition rate (human small cell lung cancer SCLC-21H) | Inhibition rate (human bone marrow rhabdomyosarcoma cell RH30) |
|---|---|---|
| 5 | 55% | 29% |
| 15 | 43% | 49% |
| 17 | 25% | 39% |
| 25 | 78% | 75% |
| 26 | 17% | 36% |
| 27 | 14% | 50% |
| 28 | 32% | 21% |
| 29 | 46% | 47% |
| 30 | 33% | 32% |
| 31 | 75% | 70% |
| 32 | 70% | 63% |
| 33 | 83% | 86% |
| 37 | 60% | 21% |
| 41 | 35% | 28% |
| 42 | 33% | 33% |
| 43 | 44% | 25% |
| 44 | 47% | 24% |
| 46 | 66% | 41% |
| 47 | 63% | 55% |
| 48 | 63% | 51% |
| 49 | 20% | 51% |
| 57 | 47% | 40% |
| 59 | 28% | 57% |
| 60 | 71% | 72% |
| 61 | 44% | 52% |
| 62 | 84% | 87% |
| 63 | 70% | 68% |
| 64 | 24% | 30% |
| 65 | 52% | 42% |
| 66 | 48% | 53% |
| 67 | 33% | 41% |
| 68 | 68% | 56% |
| 69 | 50% | 29% |
| 70 | 46% | 42% |
| 72 | 64% | 37% |
| 74 | 38% | 32% |
| 75 | 60% | 51% |
| 79 | 80% | 79% |
| 80 | 86% | 82% |
| 81 | 83% | 80% |
| 87 | 26% | 28% |

Cytotoxicity of the compounds on cell line KP3 ($IC_{50}$):

| Compound | $IC_{50}$ (µM) |
|---|---|
| 25 | 2.9 |
| 31 | 6.2 |
| 32 | 5.6 |
| 33 | 2.2 |
| 38 | <1 |
| 39 | 2.6 |
| 78 | 8.7 |
| 79 | 2.6 |
| 80 | 2.0 |
| 81 | <1 |
| 82 | <1 |
| 83 | 4.7 |

Cytotoxicity of the compounds on cell line SCLC ($IC_{50}$):

| Compound | $IC_{50}$ (µM) |
|---|---|
| 25 | 2.4 |
| 31 | 7.2 |
| 32 | 2.1 |
| 33 | 7.1 |
| 38 | 4.2 |
| 39 | 7.3 |
| 78 | 5.1 |
| 80 | <1 |
| 79 | <1 |
| 81 | 9.2 |
| 82 | 9.9 |

Cytotoxicity of the compounds on cell line RH30 ($IC_{50}$):

| Compound | $IC_{50}$ (µM) |
|---|---|
| 25 | 2.9 |
| 31 | 3.6 |
| 32 | 5.3 |
| 33 | 4.1 |
| 38 | 9.2 |
| 39 | 3.2 |
| 78 | 14.7 |
| 79 | 2.6 |
| 80 | 2.0 |
| 81 | 1.3 |
| 82 | 1.6 |
| 83 | 4.7 |

The results show that the compounds of the present application have a fairly good inhibitory effect on various solid tumor cells.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of formula (I), or a pharmaceutically acceptable salt, hydrate or solvate thereof,

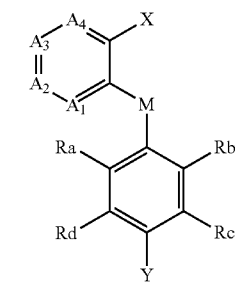

(I)

wherein,
each of $A_2$ and $A_3$ is CR', and $A_1$ and $A_4$ are independently CR' or N; or each of $A_1$ and $A_3$ is CR', and $A_2$ and $A_4$ are independently CR' or N;

M is selected from the group consisting of CR'$_2$, NH, O and S;

R' is selected from the group consisting of H, halogen atom, carbonyl (=O), carboxyl, and hydroxy;

X has a structure selected from the group consisting of: carboxyl, hydroxamic acid group, substituted or unsubstituted $C_2$-$C_{12}$ ester group, substituted or unsubstituted amide group, and substituted or unsubstituted 3-12 membered heterocyclic group;

Y is selected from the group consisting of substituted or unsubstituted $C_6$-$C_{12}$ aryl, and substituted or unsubstituted 3-12 membered heterocyclic group, wherein the substituted $C_6$-$C_{12}$ aryl is substituted with a substituent selected from the group consisting of hydroxy, carboxyl, and substituted or unsubstituted $C_1$-$C_{10}$ alkyl; and $R_a$ and $R_b$ are independently selected from the group consisting of halogen, —OH, $NH_2$, and substituted or unsubstituted $C_1$-$C_6$ alkyl;

$R_c$ and $R_d$ are independently selected from the group consisting of H, halogen, —OH, CN, $NO_2$, $NH_2$, substituted or unsubstituted $C_1$-$C_6$ alkyl, and substituted or unsubstituted $C_1$-$C_6$ alkoxy.

2. The compound of claim 1, or a pharmaceutically acceptable salt, hydrate or solvate thereof, wherein the compound of formula (I) is a compound of the following formula:

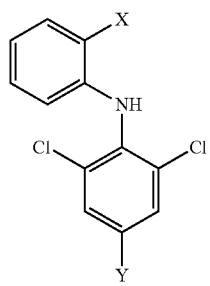

(I)

wherein,

X has a structure selected from the group consisting of: carboxyl, substituted or unsubstituted $C_2$-$C_{12}$ ester group, substituted or unsubstituted amide group, and substituted or unsubstituted 5-9 membered heterocyclic group; and Y is selected from the group consisting of substituted or unsubstituted $C_6$-$C_{12}$ aryl, and substituted or unsubstituted 3-12 membered heterocyclic group, wherein the substituted $C_6$-$C_{12}$ aryl is substituted with a substituent selected from the group consisting of hydroxy, carboxyl, substituted or unsubstituted $C_1$-$C_{10}$ alkyl.

3. The compound of claim 1, or a pharmaceutically acceptable salt, hydrate or solvate thereof, wherein X has a structure represented by the following formula:

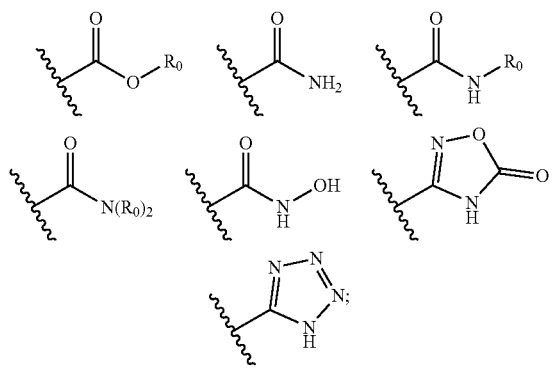

wherein each $R_0$ is independently selected from the group consisting of hydrogen, substituted or unsubstituted $C_1$-$C_6$ alkyl, substituted or unsubstituted $C_6$-$C_{10}$ aryl, substituted or unsubstituted $C_3$-$C_{10}$ cycloalkyl (including monocyclic, polycyclic, bridged ring structures), substituted or unsubstituted $C_2$-$C_6$ alkenyl, substituted or unsubstituted $C_2$-$C_6$ alkynyl, —OR", R" is selected from the group consisting of halogen atom, carboxy, hydroxy, amino, nitro, cyano, $C_1$-$C_6$ alkyl, $C_1$-$C_6$ alkoxy, $C_1$-$C_6$ alkylamino, $C_1$-$C_6$ alkoxycarbonyl, $C_1$-$C_6$ acylamino, $C_2$-$C_{12}$ ester group, substituted or unsubstituted $C_1$-$C_4$ alkyl-($C_6$-$C_{10}$ aryl), substituted or unsubstituted $C_1$-$C_4$ alkyl-(5-9 membered heterocyclyl), and substituted or unsubstituted five-membered or six-membered heteroaryl; and Y is substituted or unsubstituted benzene, substituted or unsubstituted pyridine, substituted or unsubstituted pyrimidine, substituted or unsubstituted pyridazine, substituted or unsubstituted tetrazine, substituted or unsubstituted triazine, substituted or unsubstituted pyrrole, substituted or unsubstituted thiophene, substituted or unsubstituted furan, substituted or unsubstituted tetrazole, substituted or unsubstituted triazole, substituted or unsubstituted imidazole, substituted or unsubstituted thiazole, substituted or unsubstituted oxazole, substituted or unsubstituted pyrazole, substituted or unsubstituted isothiazole, substituted or unsubstituted isoxazole, substituted or unsubstituted oxadiazole, substituted or unsubstituted thiadiazole, substituted or unsubstituted naphthalene, substituted or unsubstituted indole, substituted or unsubstituted indazole, substituted or unsubstituted quinoline, substituted or unsubstituted isoquinoline, substituted or unsubstituted benzofuran, substituted or unsubstituted benzothiophene, substituted or unsubstituted benzoimidazole, substituted or unsubstituted benzoxazole, substituted or unsubstituted benzothiazole, substituted or unsubstituted benzisothiazole, substituted or unsubstituted benzoisoxazole, substituted or unsubstituted benzotriazole, substituted or unsubstituted morpholine, substituted or unsubstituted dihydropiperidine, substituted or unsubstituted thiomorpholine, substituted or unsubstituted piperidine, substituted or unsubstituted piperazine, substituted or unsubstituted tetrahydropyran, substituted or unsubstituted dihydropyran, substituted or unsubstituted pyrroline, substituted or unsubstituted tetrahydrothiophene, substituted or unsubstituted tetrahydrofuran, substituted or unsubstituted oxetane, substituted or unsubstituted thietane, or substituted or unsubstituted azetidine.

4. The compound of claim 1, or a pharmaceutically acceptable salt, hydrate or solvate thereof, wherein Y is selected from the group consisting of

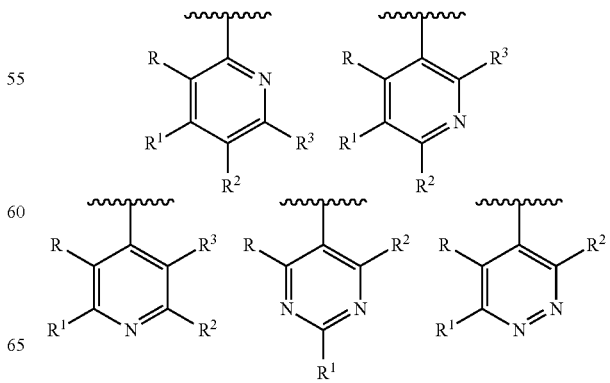

-continued
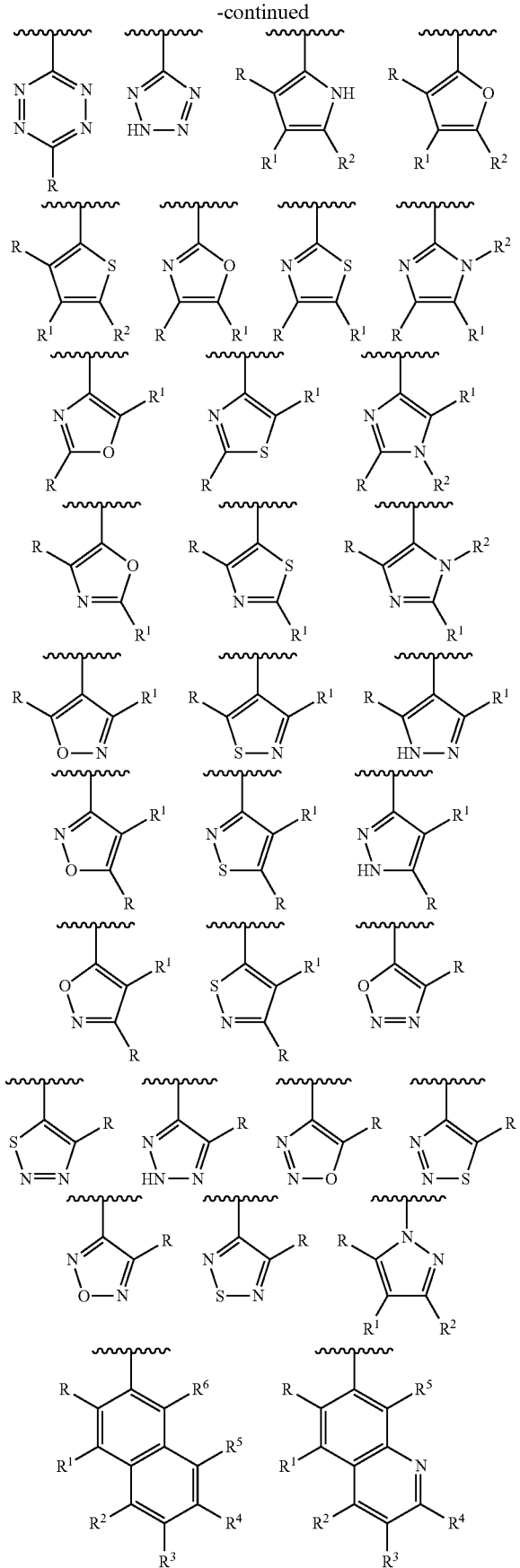
-continued
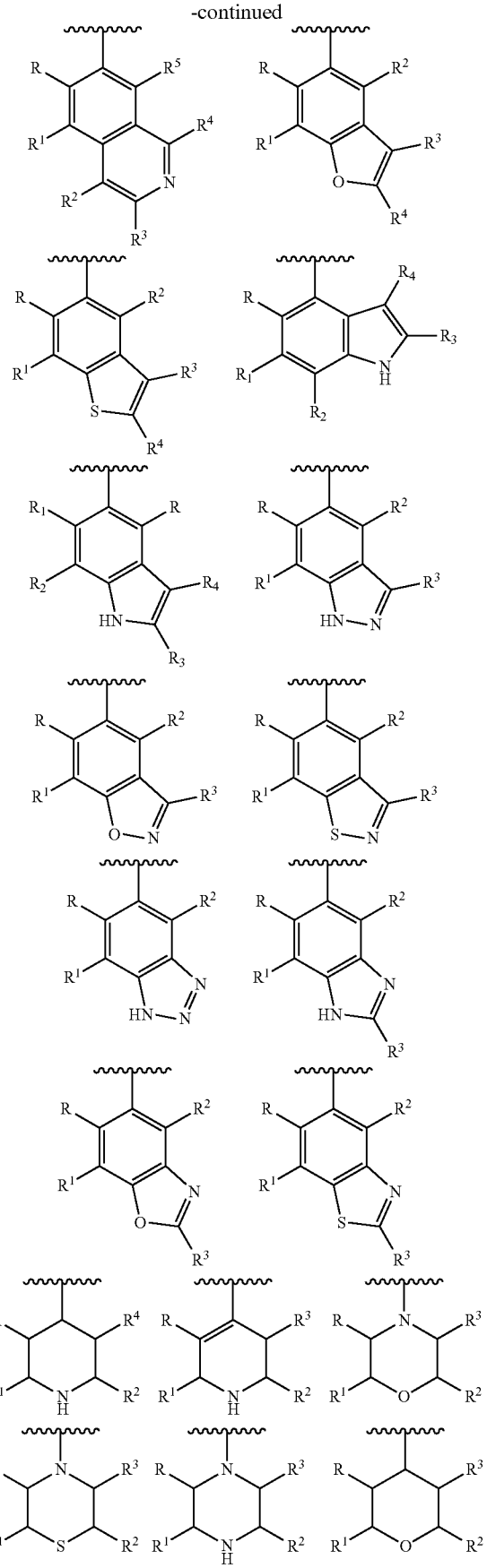

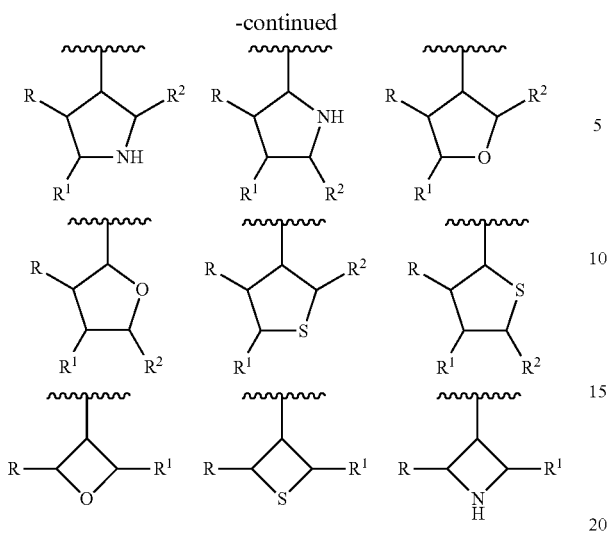

wherein each of R, R$^1$, R$^2$, R$^3$, R$^4$, R$^5$ and R$^6$ is independently hydrogen, carbonyl (=O), C$_1$-C$_6$ alkoxy, C$_1$-C$_6$ alkylamino, C$_1$-C$_6$ alkoxycarbonyl, C$_1$-C$_6$ acylamino, substituted or unsubstituted C$_1$-C$_{10}$ alkyl, substituted or unsubstituted C$_6$-C$_{10}$ aryl and five-membered or six-membered heteroaryl; and wherein the substituent is selected from the group consisting of halogen atom, carbonyl (=O), carboxyl, hydroxyl, amino, nitro, cyano, C$_1$-C$_6$ alkoxycarbonyl, C$_1$-C$_6$ acylamino, C$_1$-C$_6$ alkyl, haloC$_1$-C$_6$ alkyl, C$_1$-C$_6$ alkoxy, C$_1$-C$_6$ alkylamino, C$_6$-C$_{10}$ aryl and five-membered or six-membered heteroaryl.

5. The compound of claim 1, or a pharmaceutically acceptable salt, hydrate or solvate thereof, wherein each of R$_a$ and R$_b$ is independently selected from the group consisting of F, Cl, OH, and methyl, and wherein each of R$_c$, and R$_d$ is independently selected from the group consisting of H, F, Cl, OH, methyl and methoxy.

6. The compound of claim 1, or a pharmaceutically acceptable salt, hydrate or solvate thereof, wherein each of A$_2$ and A$_3$ is independently CR'.

7. A compound or a pharmaceutically acceptable salt, hydrate or solvate thereof, wherein the compound is selected from the group consisting of:

1

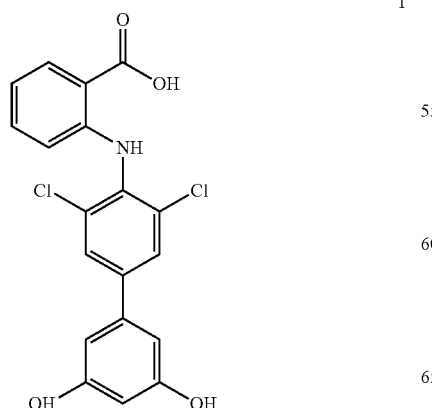

2

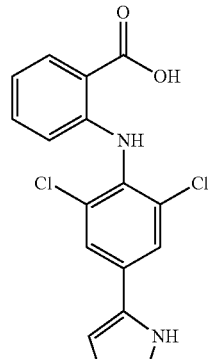

3

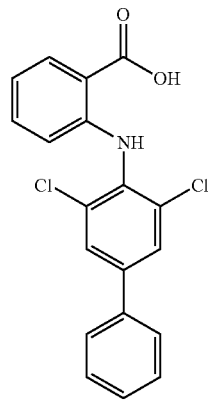

4

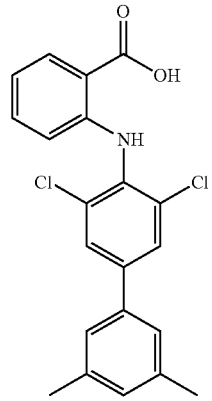

5

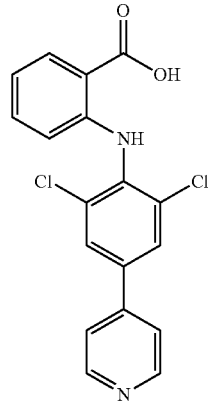

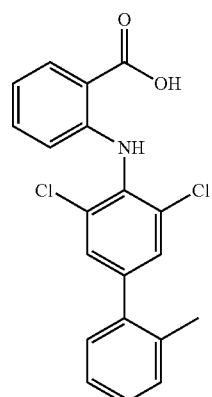
6
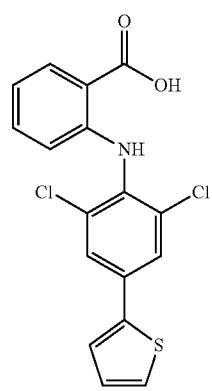
7
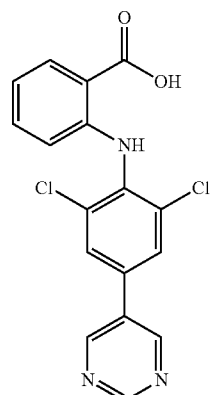
8
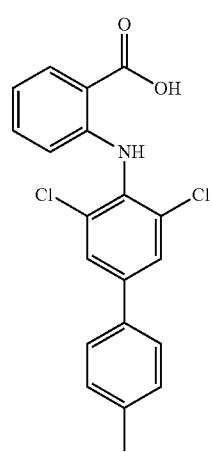
9
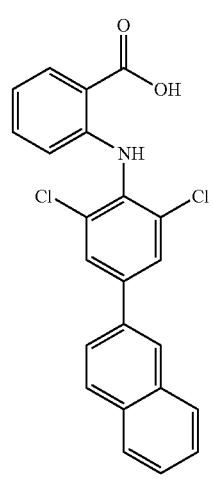
10
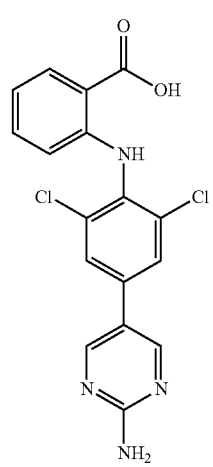
11
12

13
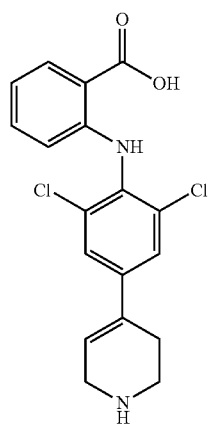
14
15
17
18
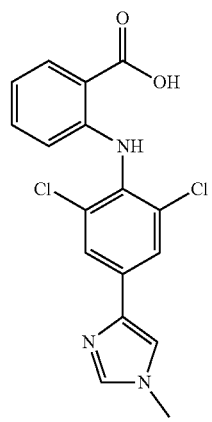
19
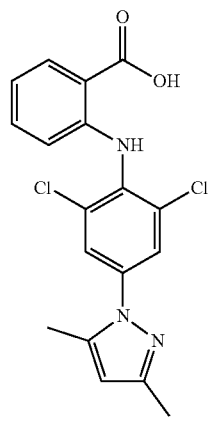
20
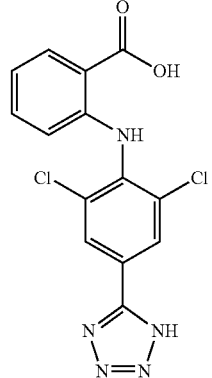
21
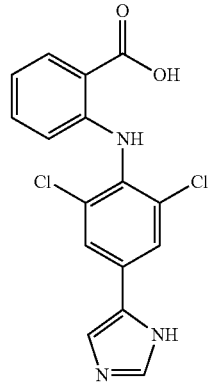

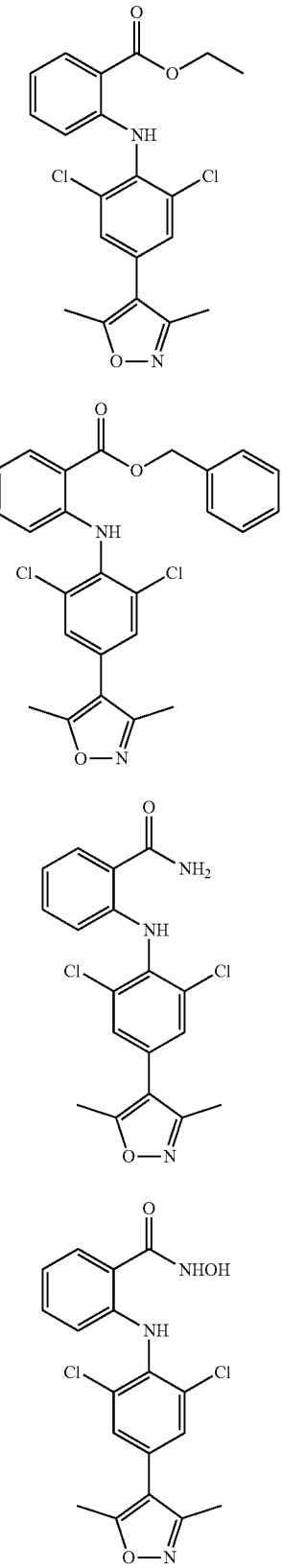
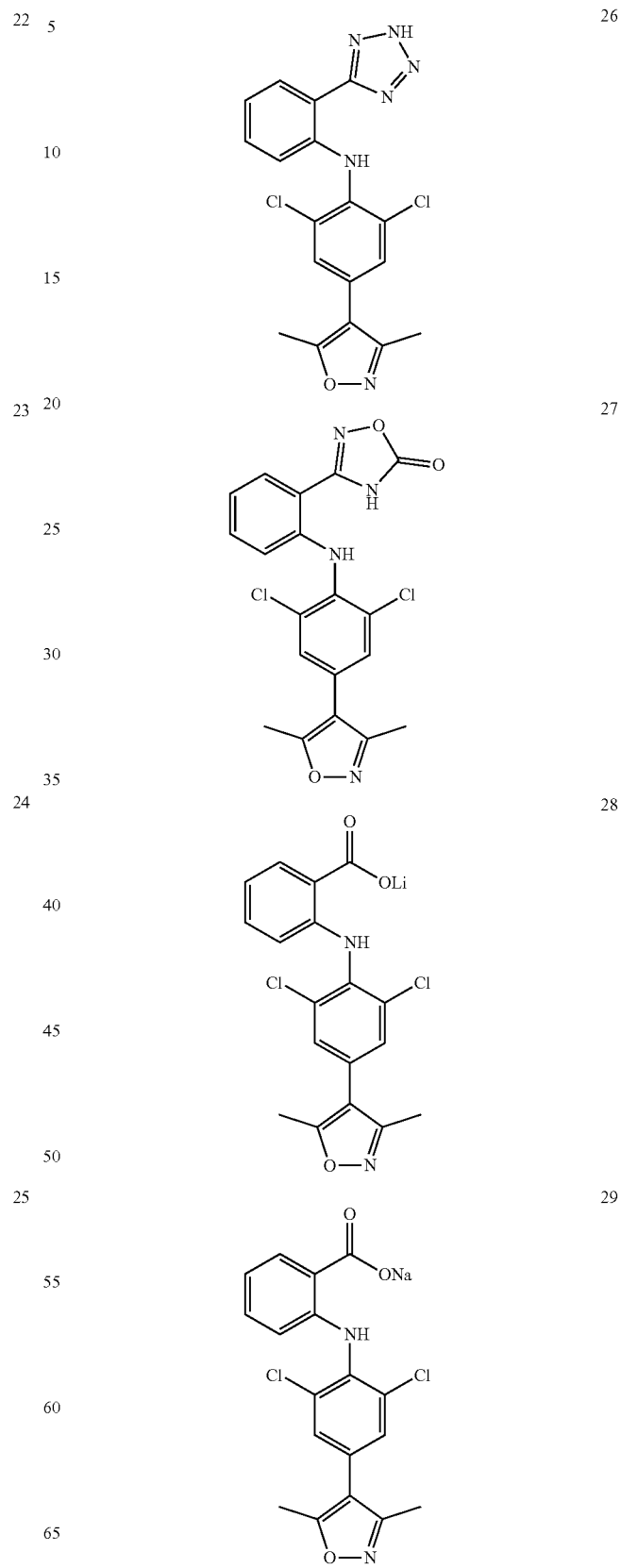

| 30 | 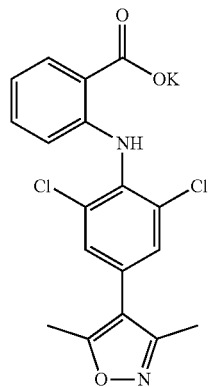 | 34 | 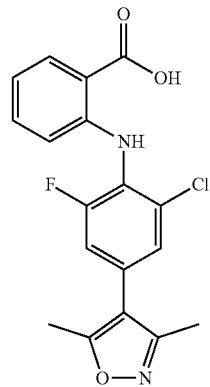 |
| 31 | 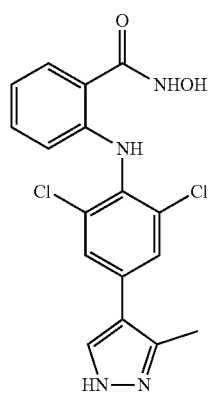 | 35 | 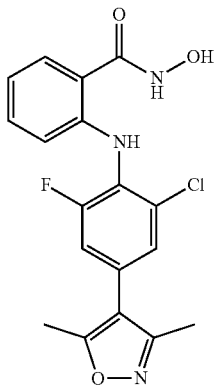 |
| 32 | 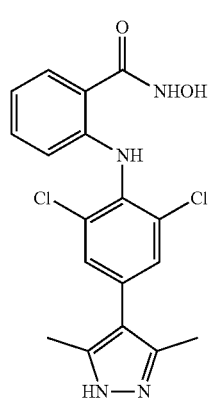 | 36 | 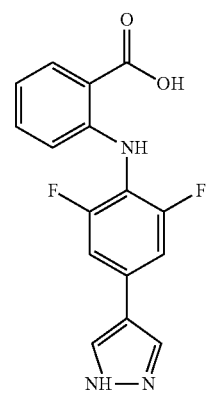 |
| 33 | 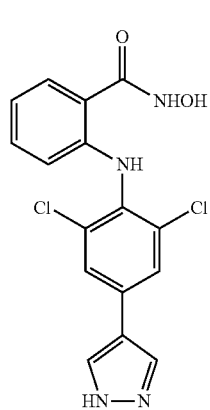 | 37 | 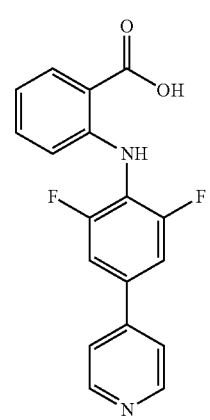 |

| 38 | 42 |
|---|---|
| 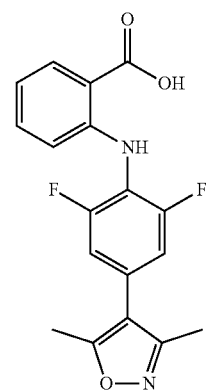 | 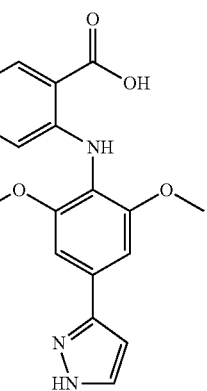 |
| 39 | 43 |
| 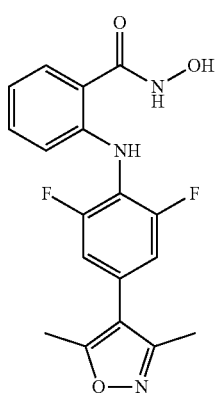 | 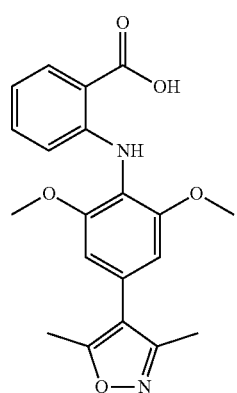 |
| 40 | 44 |
| 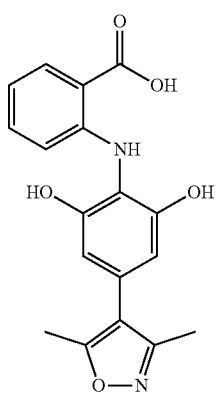 | 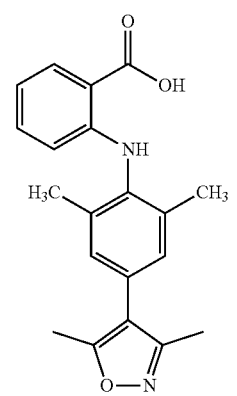 |
| 41 | 45 |
| 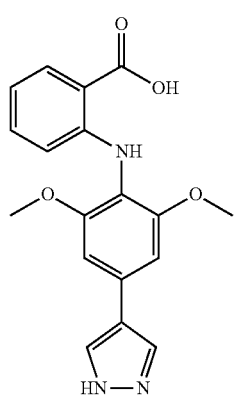 | 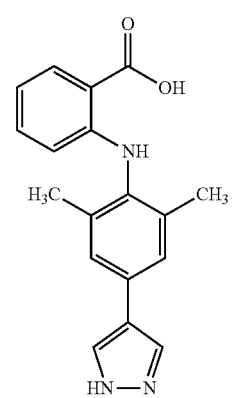 |

46
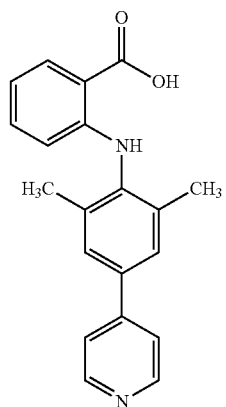
53
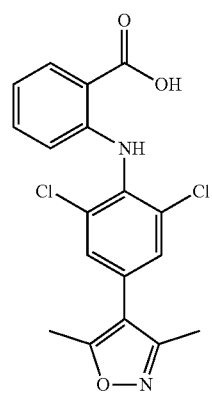
54
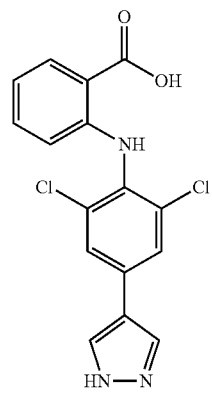
55
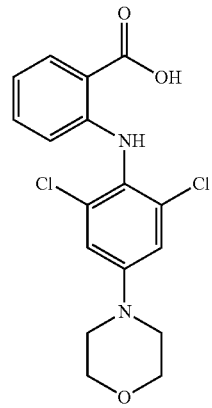
56
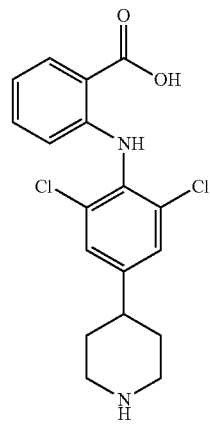
57
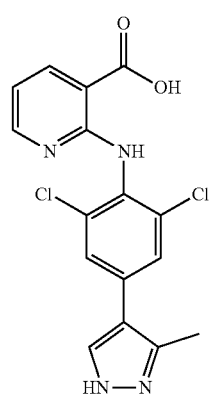
58
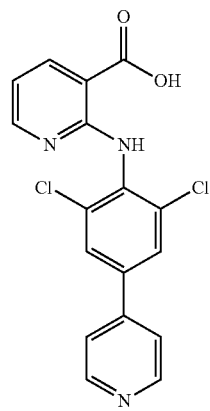
59
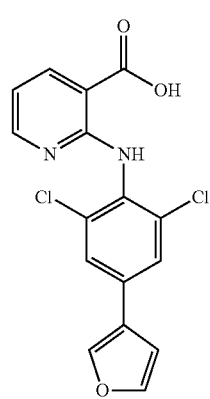

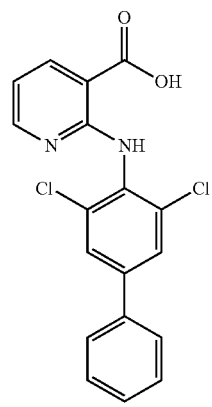
60
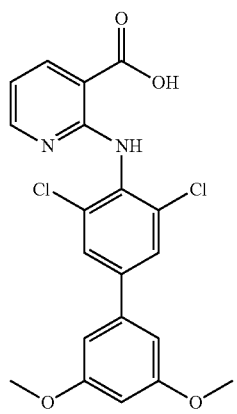
61
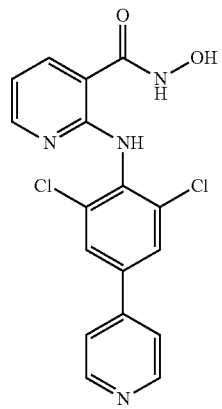
62
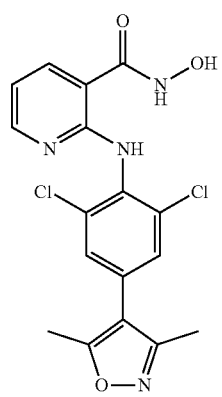
63
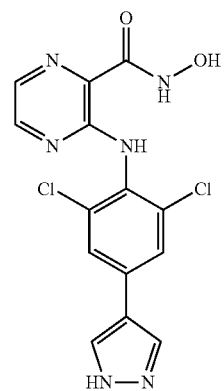
64
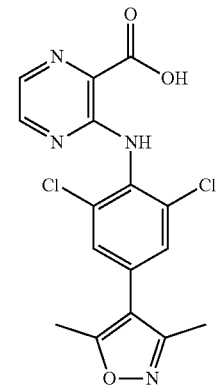
65
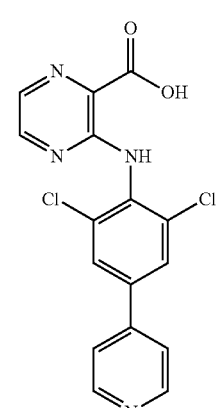
66
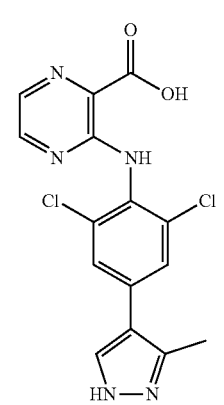
67

68
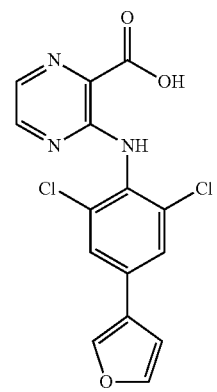
69
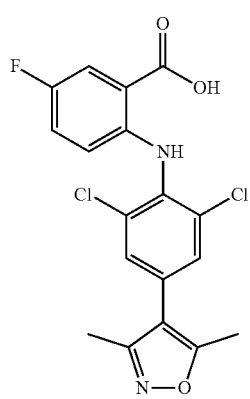
70
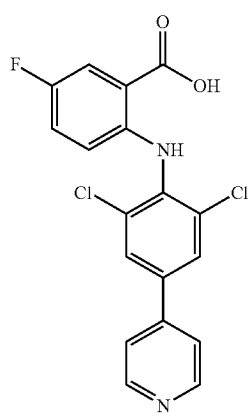
71
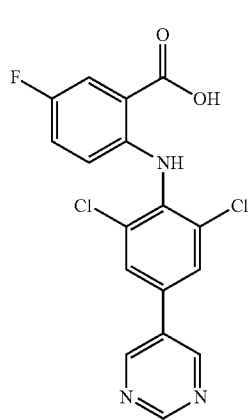
72
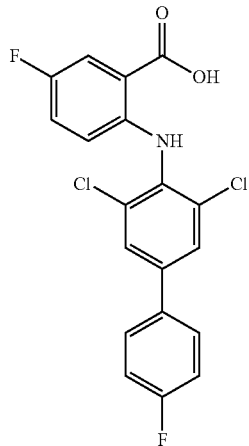
73
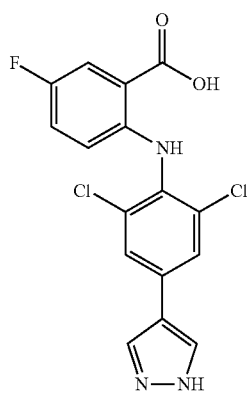
74
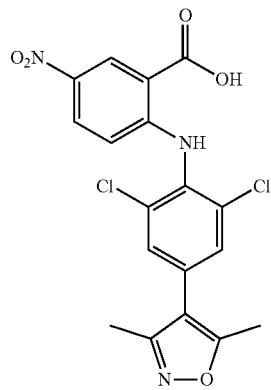
75
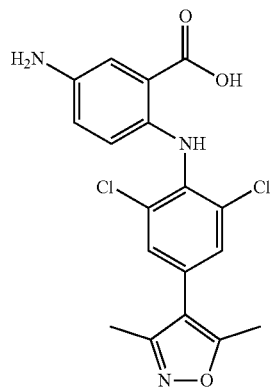

76
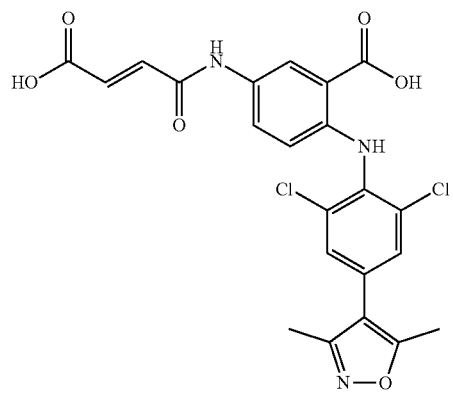
77
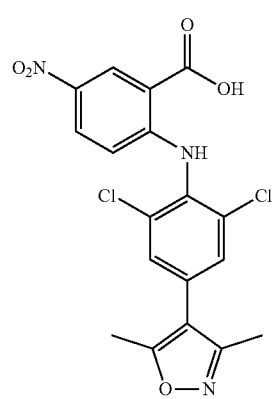
78
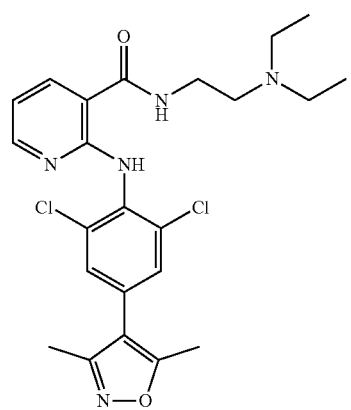
79
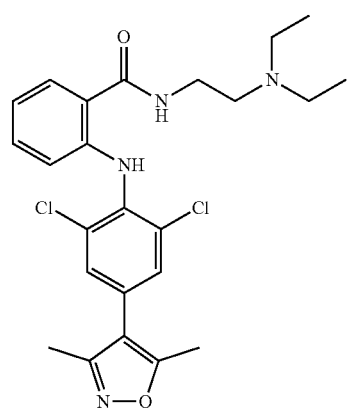
80
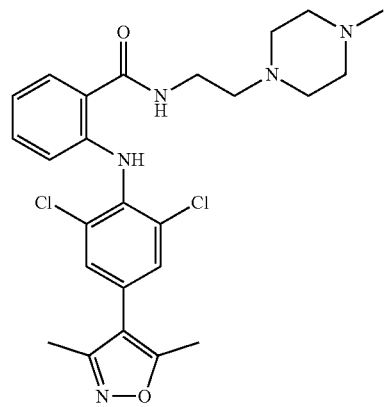
81
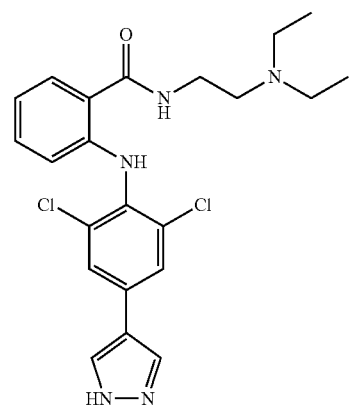
82
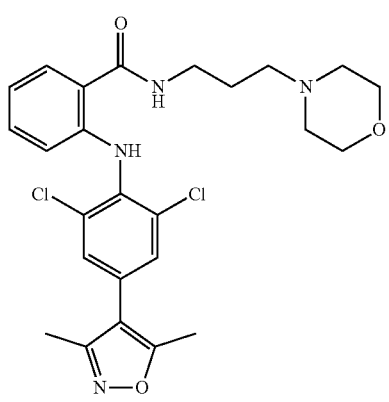
83
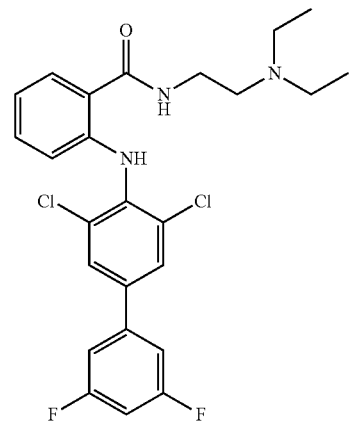

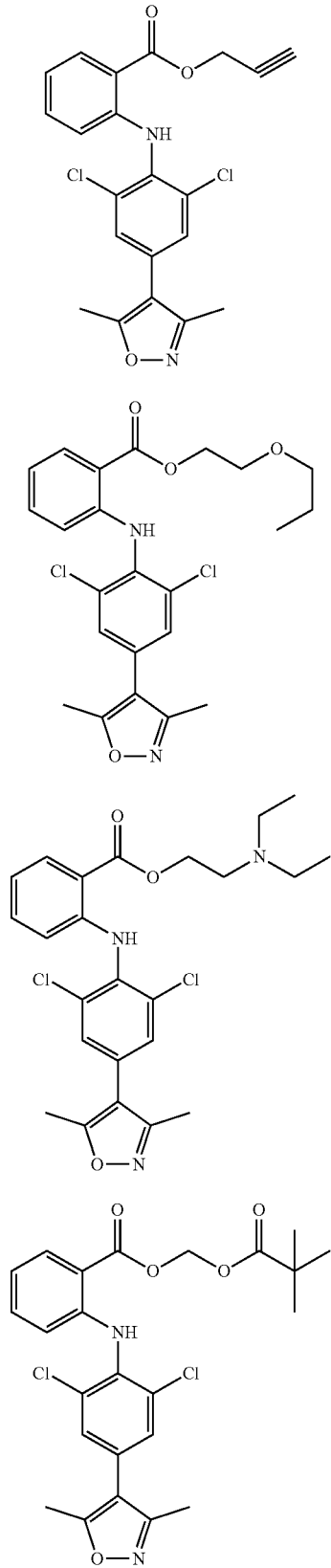

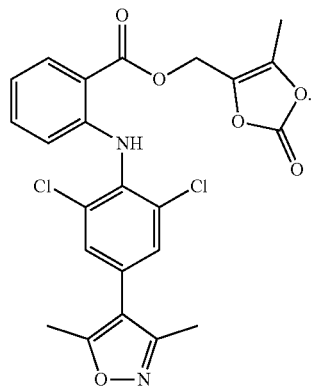

8. The pharmaceutically acceptable salt of the compound of claim 1, wherein the pharmaceutically acceptable salt is selected from the group consisting of inorganic acid salts, organic acid salts, inorganic alkali salts, and organic base salts.

9. The pharmaceutically acceptable salt of the compound of claim 1, wherein the pharmaceutically acceptable salt is alkali metal salts.

10. A pharmaceutical composition, which comprises: (i) a therapeutically effective amount of the compound of formula (I) of claim 1, or the pharmaceutically acceptable salt, hydrate or solvate thereof, and (ii) a pharmaceutically acceptable carrier.

11. The pharmaceutical composition of claim 10, which further comprises a second therapeutic agent.

12. A method of inhibiting FTO protein activity, the method comprising a step of administering an inhibitory effective amount of a compound of claim 1, or the pharmaceutically acceptable salt, hydrate or solvate thereof, or a pharmaceutical composition thereof to a subject in need thereof.

13. A method of preparing a compound of formula (I) according to claim 1:

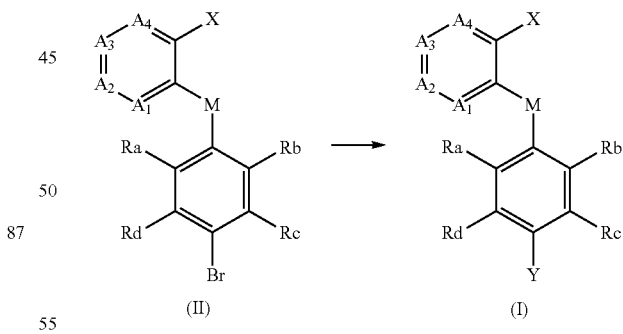

wherein the method comprises a step of reacting a compound of formula II with a coupling reagent in an inert solvent, thereby obtaining the compound of formula (I), wherein, each of $A_2$ and $A_3$ is CR', and $A_1$ and $A_4$ are independently CR' or N; or each of $A_1$ and $A_3$ is CR', and $A_2$ and $A_4$ are independently CR' or N;

M is selected from the group consisting of CR'$_2$, NH, O and S;

R' is selected from the group consisting of H, halogen atom, carbonyl (=O), carboxyl, and hydroxy;

X has a structure selected from the group consisting of: carboxyl, hydroxamic acid group, substituted or unsubstituted $C_2$-$C_{12}$ ester group, substituted or unsubstituted amide group, and substituted or unsubstituted 3-12 membered heterocyclic group;

Y is selected from the group consisting of substituted or unsubstituted $C_6$-$C_{12}$ aryl, and substituted or unsubstituted 3-12 membered heterocyclic group, wherein the substituted $C_6$-$C_{12}$ aryl is substituted with a substituent selected from the group consisting of hydroxy, carboxyl, and substituted or unsubstituted $C_1$-$C_{10}$ alkyl; and $R_a$ and $R_b$ are independently selected from the group consisting of halogen, —OH, $NH_2$, and substituted or unsubstituted $C_1$-$C_6$ alkyl;

$R_c$ and $R_d$ are independently selected from the group consisting of H, halogen, —OH, CN, $NO_2$, $NH_2$, substituted or unsubstituted $C_1$-$C_6$ alkyl, and substituted or unsubstituted $C_1$-$C_6$ alkoxy.

14. A method of treating a disease associated with FTO activity or expression amount in a subject in need thereof, comprising administering to the subject a therapeutically effective amount of the pharmaceutical composition of claim 10, wherein the disease is selected from the group consisting of obesity, metabolic syndrome, type 2 diabetes (T2D), breast cancer, small cell lung cancer, human bone marrow rhabdomyosarcoma, pancreatic cancer, and malignant glioblastoma.

15. A pharmaceutical composition, comprising the compound of claim 7, or the pharmaceutically acceptable salt, hydrate or solvate thereof, and a pharmaceutically acceptable carrier.

16. A method of treating a disease associated with FTO activity or expression amount in a subject in need thereof, comprising administering to the subject a therapeutically effective amount of the pharmaceutical composition of claim 15, wherein the disease is selected from the group consisting of obesity, metabolic syndrome, type 2 diabetes (T2D), breast cancer, small cell lung cancer, human bone marrow rhabdomyosarcoma, pancreatic cancer, and malignant glioblastoma.

* * * * *